(12) United States Patent
Rybak et al.

(10) Patent No.: US 7,811,798 B2
(45) Date of Patent: Oct. 12, 2010

(54) METHOD FOR PRODUCING AN L-AMINO ACID BY FERMENTATION USING A BACTERIUM HAVING AN ENHANCED ABILITY TO UTILIZE GLYCEROL

(75) Inventors: Konstantin Vyacheslavovich Rybak, Moscow (RU); Ekaterina Aleksandrovna Slivinskaya, Moscow (RU); Marina Evgenievna Sheremet'eva, Moscow (RU); Yulia Aleksandrovna Ovodova, Moscow (RU); Yury Ivanovich Kozlov, Moscow (RU); Vitaly Grigorievich Paraskevov, legal representative, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/488,626

(22) Filed: Jun. 22, 2009

(65) Prior Publication Data
US 2009/0317876 A1 Dec. 24, 2009

Related U.S. Application Data

(63) Continuation of application No. PCT/JP2007/075348, filed on Dec. 21, 2007.

(30) Foreign Application Priority Data
Dec. 22, 2006 (RU) .............................. 2006145712

(51) Int. Cl.
*C12P 13/24* (2006.01)
*C12P 13/22* (2006.01)
*C12N 9/02* (2006.01)
*C12N 1/20* (2006.01)

(52) U.S. Cl. ................. 435/107; 435/106; 435/108; 435/109; 435/110; 435/114; 435/115; 435/116; 435/189; 435/252.3; 435/253.33

(58) Field of Classification Search ................ 435/107, 435/106, 108, 109, 110, 114, 115, 116, 189, 435/252.3, 252.33
See application file for complete search history.

(56) References Cited

U.S. PATENT DOCUMENTS

| | | | |
|---|---|---|---|
| 5,175,107 A | 12/1992 | Debabov et al. | |
| 5,661,012 A | 8/1997 | Sano et al. | |
| 5,688,671 A | 11/1997 | Sugimoto et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 6,960,455 B2 | 11/2005 | Livshits et al. | |
| 7,138,266 B2 | 11/2006 | Debabov et al. | |
| 7,179,623 B2 | 2/2007 | Livshits et al. | |
| 7,186,531 B2 | 3/2007 | Akhverdian et al. | |
| 7,300,786 B2 | 11/2007 | Klyachko et al. | |
| 7,306,933 B2 | 12/2007 | Dien et al. | |
| 7,381,548 B2 | 6/2008 | Sheremet'eva et al. | |
| 7,399,618 B2 | 7/2008 | Klyachko et al. | |
| 7,422,880 B2 | 9/2008 | Rybak et al. | |
| 7,470,524 B2 | 12/2008 | Rybak et al. | |
| 7,476,531 B2 | 1/2009 | Tabolina et al. | |
| 2002/0110876 A1 | 8/2002 | Miyata et al. | |
| 2002/0160461 A1 | 10/2002 | Nakai et al. | |
| 2004/0132165 A1 | 7/2004 | Akhverdian et al. | |
| 2005/0048631 A1 | 3/2005 | Klyachko et al. | |
| 2005/0214911 A1 | 9/2005 | Marchenko et al. | |
| 2005/0239177 A1 | 10/2005 | Livshits et al. | |
| 2006/0019355 A1 | 1/2006 | Ueda et al. | |
| 2006/0040365 A1 | 2/2006 | Kozlov et al. | |
| 2006/0088919 A1 | 4/2006 | Rybak et al. | |
| 2006/0216796 A1 | 9/2006 | Hashiguchi et al. | |
| 2007/0004014 A1 | 1/2007 | Tsuji et al. | |
| 2007/0212764 A1 | 9/2007 | Ptitsyn et al. | |
| 2008/0113416 A1 | 5/2008 | Filippov et al. | |
| 2008/0241888 A1 | 10/2008 | Zakataeva et al. | |
| 2008/0261278 A1 | 10/2008 | Tabolina et al. | |
| 2008/0261279 A1 | 10/2008 | Tabolina et al. | |
| 2009/0081738 A1 | 3/2009 | Filippov et al. | |
| 2009/0093029 A1 | 4/2009 | Usuda et al. | |
| 2009/0098621 A1 | 4/2009 | Rybak et al. | |
| 2009/0117623 A1 | 5/2009 | Marchenko et al. | |

FOREIGN PATENT DOCUMENTS

| | | |
|---|---|---|
| EP | 1 253 195 | 10/2002 |
| EP | 1 715 055 | 10/2006 |
| EP | 1 715 056 | 10/2006 |
| WO | WO2008/002053 | 1/2008 |
| WO | WO2008/081959 | 7/2008 |
| WO | WO2008/107277 | 9/2008 |

OTHER PUBLICATIONS

Booth, I.R., "Glycerol and Methylglyoxal Metabolism, Module 3.4.3," *Escherichia coli* and *Salmonella*, 2$^{nd}$ Edition, ASM Press, Washington, DC, (2005).

Huang, H-S, et al., "Thermostable glycerol kinase from *Thermus flavus*: cloning, sequencing, and expression of the enzyme gene," Biochimica et Biophysica Acta 1998;1382:186-190.

Ito, T., et al., "Hydrogen and Ethanol Production from Glycerol-Containing Wastes Discharged after Biodiesel Manufacturing Process," J. Biosci. Bioeng. 2005;100(3):260-265.

(Continued)

*Primary Examiner*—Tekchand Saidha
(74) *Attorney, Agent, or Firm*—Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to have glycerol kinase in which feedback inhibition by fructose-1,6-bisphosphate is desensitized, thereby having enhanced ability to utilize glycerol.

12 Claims, 3 Drawing Sheets

OTHER PUBLICATIONS

Liu, W. Z., et al., "*Escherichia coli* Glycerol Kinase: Role of a Tetramer Interface in Regulation by Fructose 1,6-Bisphosphate and Phosphotransferase System Regulatory Protein III," Biochem. 1994;22:10120-10126.

Voegele, R. T., et al., "Glycerol Kinase of *Escherichia coli* Is Activated by Interaction with the Glycerol Facilitator," J. Bacteriol. 1993;175(4):1987-1094.

International Report on Patentability for PCT Patent App. No. PCT/JP2007/075348 (Jul. 2, 2009).

Herring, C. D., et al., "Comparative genome sequencing of *Escherichia coli* allows observation of bacterial evolution on a laboratory timescale," Nature Genetics 2006;38(12):1406-1412.

Holtman, C. K., et al., "Reverse Genetics of *Escherichia coli* Glycerol Kinase Allosteric Regulation and Glucose Control of Glycerol Utilization in Vivo," J. Bacteriol. 2001;183(11):3336-3344.

Honisch, C., et al., "High-throughput mutation detection underlying adaptive evolution of *Escherichia coli*-K12," Genome Research 2004;14(12):2495-2502.

Ormö, M., et al., "Crystal Structure of a Complex *Escherichia coli* Glycerol Kinase and an Allosteric Effector Fructose 1,6-Bisphosphate," Biochem. 1998;37:16565-16572.

Pettigrew, D., et al., "A Single Amino Acid Change in *Escherichia coli* Glycerol Kinase Abolishes Glucose Control of Glycerol Utilization in Vivo," J. Bacteriol. 1996;178(10):2846-2852.

International Search Report and Written Opinion of the International Searching Authority for PCT Patent App. No. PCT/JP2007/075348 (Apr. 3, 2008).

Fig. 1

```
P0A6F3      --------TEKKYIVALDQGTTSSRAVVMDHDANIISVSQREFEQIYPKPGWVEHDPMEI
Q3YV52      MTTGQLNMTEKKYIVALDQGTTSSRAVVMDHDANIISVSQREFEQIYPKPGWVEHDPMEI
Q8D1T6      MTT--ENTTQKKYIVALDQGTTSSRAVVLDHNANIVSVSQREFTQIYPKAGWVEHDPMEI
Q51390      ----MTDKHNKKYVVALDQGTTSSRAIVFDRDANVVSQAQREFAQFYPQAGWVEHDPMEI
P18157      ---------METYILSLDQGTTSSRAILFNKEGKIVHSAQKEFTQYFPHPGWVEHNANEI
                    :..*:::*********:::::..::  :*:** * :*:.*****:. **

P0A6F3      WATQSSTLVEVLAKADISSDQIAAIGITNQRETTIVWEKETGKPIYNAIVWQCRRTAEIC
Q3YV52      WATQSSTLVEVLAKADISSDQIAAIGITNQRETTIVWEKETGKPIYNAIVWQCRRTAEIC
Q8D1T6      WATQSSTLIEVLAKAGINSDEIAGIGITNQRETTIVWDKVTGKPVYNAIVWQCRRTADIC
Q51390      WATQSSTLVEALAQASIEHDQVAAIGITNQRETTVVWDRHSGRPIHNAIVWQCRRSAAIC
P18157      WGSVLAVIASVISESGISASQIAGIGITNQRETTVVWDKDTGSPVYNAIVWQSRQTSGIC
            *.:   :..: ..::::.*. .::*.**********:**:: :* *::*****.*:::**

P0A6F3      EHLKRDGLEDYIRSNTGLVIDPYFSGTKVKWILDHVEGSRERARRGELLFGTVDTWLIWK
Q3YV52      EHLKRDGLEDYIRSNTGLVIDPYFSGTKVKWILDHVEGSRERARRGELLFGTVDTWLIWK
Q8D1T6      EKLKKEGLEEYIRHNTGLVVDPYFSGTKVKWILDNVEGARERAERGELLFGTVDTWLVWN
Q51390      AQLKRDGLEDYIRETTGLVTDPYFSGTKLKWILDNVEGARERARNGDLLFGTIDTWLIWK
P18157      EELREKGYNDKFREKTGLLIDPYFSGTKVKWILDNVEGAREKAEKGELLFGTIDTWLIWK
            .*:..*  :: :* .***. ********:*****:****:***.**:..*:*****:****:*:

P0A6F3      MTQGRVHVTDYTNASRTMLFNIHTLDWDDKMLEVLDIPREMLPEVRRSSEVYGQTNIGGK
Q3YV52      MTQGRVHVTDYTNASRTMLFNIHTLDWDDKMLEVLDIPREMLPEVRRSSEVYGQTNIGGK
Q8D1T6      MTQGRVHVTDYTNASRTMMFNIRTKEWDDRMLKALNIPRAMLPEVRPSSEIYGKTNIGGK
Q51390      LTEGKVHVTDYTNASRTMLFNIHSRDWDARMLEVLDIPRSMLPEVRNSSEVYGNARIGGV
P18157      MSGGKAHVTDYSNASRTLMFNIYDLKWDDQLLDILGVPKSMLPEVKPSSHVYAETVDYHF
            ::   *:.*****:*****::***   .** ::*. *.:*: *****:  **.:*.::

P0A6F3      GGTRIPISGIAGDQQAALFGQLCVKEGMAKNTYGTGCFMLMNTGEKAVKSENGLLTTIAC
Q3YV52      GGTRIPISGIAGDQQAALFGQLCVKEGMAKNTYGTGCFMLMNTGEKAVKSENGLLTTIAC
Q8D1T6      GGTRIPIAGIAGDQQAALFGQLCVQPGMAKNTYGTGCFLLMNTGEEAVQSTHGLLTTIAC
Q51390      GGGELPIAGIAGDQQAALFGQMCVEPGQAKNTYGTGCFLLMHTGDKAVKSTHGLLTTIAC
P18157      FGKNIPIAGAAGDQQSALFGQACFEEGMGKNTYGTGCFMLMNTGEKAIKSEHGLLTTIAW
            *  .:**:*  *****:*****  *.:   * .**********:**:**::*:* :*******

P0A6F3      GPTGEVNYALEGAVFMAGASIQWLRDEMKLINDAYDSEYFATKVQNTNGVYVVPAFTGLG
Q3YV52      GPTGEVNYALEGAVFMAGASIQWLRDEMKLINDAYDSEYFATKVQNTNGVYVVPAFTGLG
Q8D1T6      GPRGEVNYALEGAVFIGGASIQWLRDELKLIGDATDSEYFATKVKNSNGVYVVPAFTGLG
Q51390      GPRGEVGYALEGAVFNGGSTVQWLRDELKVINDSFDSEYFATKVKDSNGVYLVPAFTGLG
P18157      GIDGKVNYALEGSIFVAGSAIQWLRDGLRMFQDSSLSESYAEKVDSTDGVYVVPAFVGLG
            *  *:*.*****::*  .*:::****** :::: **  :* * **..::**.****.***

P0A6F3      APYWDPYARGAIFGLTRGVNANHIIRATLESIAYQTRDVLEAMQADSGIRLHALRVDGGA
Q3YV52      APYWDPYARGAIFGLTRGVNANHIIRATLESIAYQTRDVLEAMQADSGIRLHALRVDGGA
Q8D1T6      APYWDPYARGAIFGLTRGVNSNHIIRATLESIAYQTRDVLDAMQADSGARLKSLRVDGGA
Q51390      APYWDPYARGAVFGLTRGVKADHLIRATLESIAYQTRDVLDAMQRDAGERLRALRVDGGA
P18157      TPYWDSDVRGSVFGLTRGTTKEHFIRATLESLAYQTKDVLDAMEADSNISLKTLRVDGGA
            :****. .**::******.. :*:********.****:***:**: *:.  *::*******

P0A6F3      VANNFLMQFQSDILGTRVERPEVREVTALGAAYLAGLAVGFWQNLDELQEKAVIEREFRP
Q3YV52      VANNFLMQFQSDILGTRVERPEVREVTALGAAYLAGLAVGFWQNLDELQEKAVIEREFRP
Q8D1T6      VANNFLMQFQADILGTRVERPAIRESTALGAAFLAGLATGFWDDLDEVKSKAVIEREFRP
Q51390      VANNFLMQFQADILGTRVERPVMRETTALGAAYLAGLACGFWSSLDELKSKAVIERVFEP
P18157      VKNNFLMQFQGDLLNVPVERPEINETTALGAAYLAGIAVGFWKDRSEIANQWNLDKRFEP
            * ********.*:*.. **** :.* ******:***:* ***.. .*: .: ::: *.*

P0A6F3      GIETTERNYRYAGWKKAVKRAMAWEEHDE-
Q3YV52      GIETTERNYRYAGWKKAVKRAMAWEEHDVM
Q8D1T6      GIETTERDIRYKGWKKAVARARDWEEHDE-
Q51390      ECDEPRREKLYAGWKKAVERTRGWDDGEL-
P18157      ELEEEKRNELYKGWQKAVKAAMAFK-----
            :  .*: * **:***   :   :.
```

Obtained PCR product (1699 bp)

METHOD FOR PRODUCING AN L-AMINO ACID BY FERMENTATION USING A BACTERIUM HAVING AN ENHANCED ABILITY TO UTILIZE GLYCEROL

The present application is a continuation of PCT Patent Application No. PCT/JP2007/075348, filed on Dec. 21, 2007, which claims priority under 35 U.S.C. §119 to Russian Patent Application No. 2006145712, filed on Dec. 22, 2006, the entireties of which are incorporated by reference. Also, the Sequence Listing filed electronically herewith is hereby incorporated by reference (File name: US-310_Seq_List; File size: 95 KB; Date recorded: Jun. 19, 2009).

BACKGROUND OF THE INVENTION

1. Technical Field

The present invention relates to biotechnology, specifically to a method for producing L-amino acids by fermentation using glycerol, and more specifically to a method for producing L-amino acids using bacteria having enhanced ability to utilize glycerol. An inexpensive carbon source including glycerol could be utilized for commercial production of L-amino acids.

2. Background Art

Conventionally, L-amino acids have been industrially produced by a process of fermentation using strains of different microorganisms. The fermentation media for the process should contain sufficient amounts of different sources of carbon and nitrogen.

Traditionally various carbohydrates such as hexoses, pentoses, trioses; various organic acids and alcohols are used as a carbon source. Hexoses include glucose, fructose, mannose, sorbose, galactose and the like. Pentoses include arabinose, xylose, ribose and the like. But abovementioned carbohydrates and other traditional carbon sources, such as molasses, corn, sugarcane, starch, its hydrolysate, etc., used in the industry are still relatively expensive and a reduction in price of L-amino acid produced is desired.

Glycerol, especially glycerol obtained as by-product of biodiesel production, is a favorable feedstock for L-amino acid production because it is both readily available and less expensive than carbohydrates, corn, sugarcane or other sources of carbon. It is known also that bacteria can use glycerol as a carbon source for growth. (Ito T. et al, J Biosci Bioeng., 100, 3, 260-5 (2005)).

Two proteins, the glycerol facilitator and glycerol kinase, are involved in the entry of external glycerol into cellular metabolism. Glycerol kinase (EC2.7.1.30) encoded by the glpK gene is a component of regulatory network in *E. coli* by which glucose and other carbon sources control the utilization of glycerol and the gene expression that is needed for glycerol metabolism. (*Escherichia coli* and *Salmonella*. $2^{nd}$ edition ASM Press Washington, D.C.). The proteins involved in glycerol metabolism are encoded by the glp regulon, which contains five operons located at three different chromosomal loci. Glucose modulation of glycerol utilization involves both regulation of transcription and posttranslational control of glycerol kinase catalytic activity. Transcription of the regulon is negatively controlled by a specific repressor encoded by the glpR gene.

It is known that cytoplasmic glycerol is immediately phosphorylated by the ATP-dependent glycerol kinase, which is present in its enzymatically active form associated with the glycerol facilitator GlpF (Voegele, R. T. et al, J. Bacteriol 175, 4, 1087-1094 (1993))). Furthermore, the glycerol kinase is subject to feedback inhibition by fructose-1,6-bisphosphate (fructose-1,6 diphosphate, FBP). Accordingly, the activity of glycerol kinase is rate-limiting in the metabolism of glycerol by cells of *Escherichia coli*.

The glycerol facilitator is thought to act as a carrier or to form a selective pore in the cytoplasmic membrane, whereas the kinase traps the glycerol inside the cell as sn-glycerol-3-phosphate. It was found that the kinetics of glycerol uptake in a facilitator-minus strain are significantly different from the kinetics of glycerol uptake in the wild type. Free glycerol was not observed inside wild-type cells transporting glycerol, and diffusion of glycerol across the cytoplasmic membrane was not the rate-limiting step for phosphorylation in facilitator-minus mutants. Therefore, the kinetics of glycerol phosphorylation is different, depending on the presence or absence of the facilitator protein. It was concluded that there is an interaction between the glycerol facilitator protein and glycerol kinase that stimulates kinase activity, analogous to the hexokinase- and glycerol kinase-porin interactions in mitochondria (Voegele, R. T. et al, J. Bacteriol., 175, 4, 1087-1094 (1993)).

A mutant strain which produces a glycerol kinase resistant to inhibition by fructose-1,6-bisphosphate grows faster than its wild-type parent on glycerol as the sole source of carbon. Pittigrew et al. identified the *Escherichia coli* glycerol kinase mutation G304S which lost sensitivity to inhibition by FBP (Pettigrew, D. W., Liu, W. Z., Holmes, C., Meadow, N. D., and Roseman, S., J. Bacteriol. 178, 10, 2846-52 (1996)). Honisch et. al. identified the mutation G231D in glycerol kinase of an adaptively evolved strain, and kinetically characterized wild type glycerol kinase and G231D mutant. Kinetic studies for G231D variant show a 12-fold increase in glycerol kinase activity and simultaneous increase in tolerance toward the allosteric inhibitor fructose-1,6-bisphosphate (Honisch, C. et. al., Genome Research, 14: 2495-2502 (2004)).

Furthermore, adaptation of *E. coli* to glycerol media was tested, and some mutations which allowed for growth in the glycerol medium were determined (Herring C. D. et al, Nat. Genet., 38 (12): 1406-1412 (2006). Epub 2006 Nov. 5).

It is known also that attenuation of glpR is effective for producing L-amino acid production by fermentation in a glycerol containing medium. (EP1715056A1)

However, such known mutants are not sufficient for L-amino acid production from glycerol.

Furthermore, at present, there are no reports describing bacteria having a synergetic effect by combination of a mutation in glycerol kinase and attenuation of glpR on L-amino acid production from glycerol.

SUMMARY OF THE INVENTION

The present invention provides an L-amino acid producing bacterium which has an enhanced ability to utilize glycerol, and a method for producing L-amino acids by fermentation of glycerol using the bacterium. A fermentation feedstock containing glycerol obtained, for example, as by-product of biodiesel production, can be used as a carbon source for the culture medium.

This aspect was achieved by finding that a bacterium which comprises glycerol kinase in which feedback inhibition by fructose-1,6 bisphosphate is desensitized shows increased production of L-amino acid in the medium containing glycerol.

It is an aspect of the present invention to provide a method for producing an L-amino acid including;

a) culturing in a culture medium containing glycerol an L-amino acid producing bacterium of the Enterobacteriaceae family, and b) collecting L-amino acid from the culture, wherein said bacterium comprises glycerol kinase in which feedback inhibition by fructose-1,6-bisphosphate is desensitized, and said glycerol kinase comprises mutation to replace at least one amino acid with another amino acid in the region corresponding to the positions from 233 to 235 of the amino acid sequence of a wild type glycerol kinase shown in SEQ ID NO: 4.

It is a further aspect of the present invention to provide the method as described above, where the glycerol kinase further comprises mutation to replace at least one amino acid with another amino acid in the region corresponding to the positions from 231 to 232.

It is a further aspect of the present invention to provide the method as described above, wherein the glycerol kinase comprises mutation selected from the group consisting of replacing Gly residue at position 234 with Asp residue at position 234 with Asp residue, replacing Lys-Gly-Gly at positions from 233 to 235 with Arg-Ile-Pro, and replacing Gly-Gly-Lys-Gly-Gly at positions from 231 to 235 with Arg-Ala-His-Leu-Ala.

It is a further aspect of the present invention to provide the method as described above, wherein the bacterium is further modified so that activity of glycerol facilitator and/or glycerol 3-phosphate dehydrogenase is enhanced.

It is a further aspect of the present invention to provide the method as described above, wherein the expression of the protein is increased by increasing the copy number of the gene or modifying an expression control sequence of the gene so that the expression of the gene is enhanced.

It is a further aspect of the present invention to provide the method as described above, wherein the bacterium is further modified so that activity of triose phosphate isomerase is enhanced.

It is a further aspect of the present invention to provide the method as described above, wherein the expression of the protein is increased by increasing the copy number of the gene or modifying an expression control sequence of the gene so that the expression of the gene is enhanced.

It is a further object of the present invention to provide the method as described above, wherein the L-amino acid is selected from the group consisting of an aromatic L-amino acid and a non-aromatic L-amino acid.

It is a further object of the present invention to provide the method as described above, wherein the aromatic L-amino acid is selected from the group consisting of L-phenylalanine, L-tyrosine, and L-tryptophan.

It is a further object of the present invention to provide the method as described above, wherein the non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further object of the present invention to provide the method as described above, wherein the bacterium belongs to the genus *Escheriahia* or *Pantoea*.

It is a further object of the present invention to provide the method as described above, wherein the glycerol is obtained as a by-product of biodiesel production.

BRIEF DESCRIPTION OF THE DRAWINGS

FIG. 1 shows the alignment of the primary sequences of glycerol kinase from *Escherichia coli* (P0A6F3, SEQ ID NO: 4), *Shigella sonnei* (Q3YV52, SEQ ID NO: 43), *Yersinia pestis* (Q8D1T6, SEQ ID NO: 44), *Pseudomonas aeruginosa* (Q51390, SEQ ID NO: 45), and *Bacillus subtilis* (P18157, SEQ ID NO: 46). The alignment was done by using the PIR Multiple Alignment program (http://pir.georgetown.edu). The identical amino acids are indicated by an asterisk (*), similar amino acids are indicated by a colon (:).

DETAILED DESCRIPTION OF THE PREFERRED EMBODIMENTS

1. Bacterium

Figure 2:
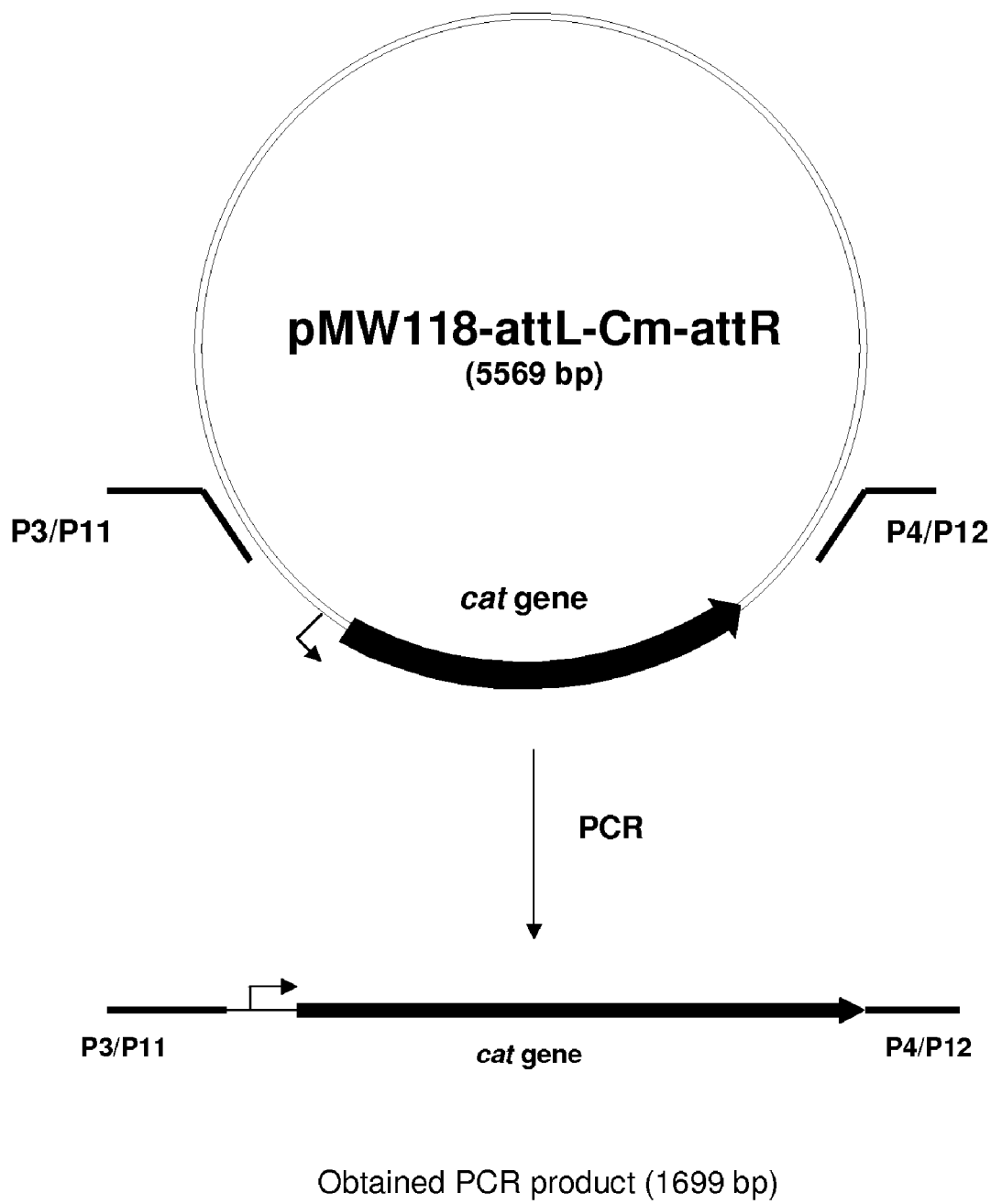
FIG. 2 shows the relative positions of primers P3 and P4, and P11 and P12 on plasmid pMW118-attL-Cm-attR which is used as a template for PCR amplification of the cat gene.

Exemplary bacteria of the present invention can include an L-amino acid-producing bacterium of the Enterobacteriaceae family which has been modified to contain glycerol kinase in which feedback inhibition by fructose-1,6-bisphosphate is desensitized, and in which at least one amino acid is replaced with another amino acid in the region corresponding to the positions from 233 to 235 of the amino acid sequence of a wild type glycerol kinase shown in SEQ ID NO: 4, thereby having an enhanced ability to utilize glycerol. The glycerol kinase which has the mutation as described above is referred to as "mutant glycerol kinase".

The phrase "to utilize glycerol" means that bacterium grows on a medium containing glycerol, and wherein glycerol is a carbon source. The phrase "enhanced ability to utilize glycerol" means that the modified bacterium can utilize glycerol more effectively as compared with an unmodified bacterium, or can grow faster than an unmodified bacterium on the culture medium containing glycerol.

A culture medium can contain glycerol as the sole carbon source, or can be in a mixture with other carbon sources By way of example, the other carbon sources can be different carbohydrates, such as glucose, sucrose, xylose, arabinose, etc., alcohols, such as ethanol, methanol, etc.

"L-amino acid-producing bacterium" means a bacterium which can have an ability to produce and excrete an L-amino acid into a medium, when the bacterium is cultured in the medium.

The term "L-amino acid-producing bacterium" also means a bacterium which can produce and can cause accumulation of an L-amino acid in a culture medium in an amount larger than a wild-type or parental strain of the bacterium, for example, *E. coli*, such as *E. coli* K-12. "L-amino acid producing bacterium" also can mean that the bacterium can cause accumulation in a medium of an amount not less than 0.5 g/L, or, alternatively, not less than 1.0 g/L, of the target L-amino acid.

The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan.

The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, and L-tryptophan.

The Enterobacteriaceae family can include bacteria belonging to the genera *Escherichia, Enterobacter, Raoultella, Erwinia, Klebsiella, Pantoea, Photorhabdus, Providen-*

*cia, Salmonella, Serratia, Shigella, Morganella, Yersinia,* etc. Specifically, those classified into the Enterobacteriaceae according to the taxonomy used by the NCBI (National Center for Biotechnology Information) database (http://www.ncbi.nlm.nih.gov/Taxonomy/Browser/wwwtax-.cgi?id=91347) can be used. In an exemplary embodiment in accordance with the presently disclosed subject matter, the bacterium can belong to the genus *Escherichia* or *Pantoea*.

The phrase "a bacterium belonging to the genus *Escherichia*" means that the bacterium can be classified into the genus *Escherichia* according to the classification known to a person skilled in the art of microbiology. Examples of a bacterium belonging to the genus *Escherichia* as used in the present invention can include, but are not limited to, *Escherichia coli* (*E. coli*).

The bacterium belonging to the genus *Escherichia* that can be used in accordance with the presently disclosed subject matter is not particularly limited. For example, bacteria in accordance with the presently disclosed subject matter can encompass bacteria described by Neidhardt, F. C. et al. (*Escherichia coli* and *Salmonella typhimurium*, American Society for Microbiology, Washington D.C., 1208, Table 1).

The phrase "a bacterium belonging to the genus *Pantoea*" means that the bacterium can be classified as the genus *Pantoea* according to the classification known to a person skilled in the art of microbiology. Some species of *Enterobacter agglomerans* have been recently re-classified into *Pantoea agglomerans, Pantoea ananatis, Pantoea* stewartii or the like, based on the nucleotide sequence analysis of 16S rRNA, etc. (Int. J. Syst. Bacteriol., 43, 162-173 (1993)).

The phrase "glycerol kinanse in which feedback inhibition by fructose-1,6-bisphosphate (FBP) is desensitized" means that glycerol kinase in the presence of high concentrations of fructose-1,6-bisphosphate can be increased as compared with a wild-type strain or non-mutated strain. Whether feedback inhibition of glycerol kinase by FBP is desensitized can be confirmed by measurement of glycerol kinase activity in the presence of FBP (Pettigrew, D. W. et al. J. Bacteriol. 178, 10, 2846-52 (1996)). Effect of desentization of feedback inhibition of glycerol kinase by FBP on glycerol utilization can be confirmed by comparing the growth of modified bacterium and unmodified bacterium in glycerol medium.

The glpK gene of *E. coli* (synonyms: ECK3918, b3926) encodes glycerol kinase (synonym B3926). The glpK gene (nucleotides complementary to nucleotides in positions 4,113,737 to 4,115,245; GenBank accession no. NC_000913.2; gi: 49175990) is located between the glpX gene and the glpF gene on the chromosome of *E. coli* K-12. The nucleotide sequence of the glpK gene and the amino acid sequence of GlpK encoded by the glpK gene are shown in SEQ ID NO: 3 and SEQ ID NO: 4, respectively.

The mutation of glycerol kinase to desensitize feedback inhibition by FBP can be the replacement of one or more amino acids in the region corresponding to the positions from 233 to 235 in the amino acid sequence of a wild type glycerol kinase presented by SEQ ID NO: 4 with another amino acid. The mutant glycerol kinase can further contain mutations such as the replacement of at least one amino acid with another amino acid in the region corresponding to the positions from 231 to 232. The "another amino acid" is not particularly limited so long as it is different from the original amino acid and feedback inhibition of glycerol kinase by FBP is desensitized by the replacement. However, "another amino acid" in the positions 231, 232, 234, 235 means other than Gly, and the substitution of Lys, Glu, Thr, Val, Leu, Ile, Ser, Asp, Asn, Gln, Arg, Cys, Met, Phe, Trp, Tyr, Ala, Pro or His are exemplary. "Another amino acid" in the position 233 means other than Lys, and the substitution of Glu, Thr, Val, Leu, Ile, Ser, Asp, Asn, Gln, Arg, Cys, Met, Phe, Trp, Tyr, Ala, Pro, Gly or His are exemplary. In an exemplary embodiment in accordance with the presently disclosed subject matter, Gly at position 231 can be replaced with an basic amino acid such as Arg, Lys or an acidic amino acid such as Asp, Glu.

In another exemplary embodiment in accordance with the presently disclosed subject matter, Gly at position 232 can be replaced with an aliphatic amino acid such as Ala, Val, Leu or an acidic amino acid such as Asp or Glu.

In another exemplary embodiment in accordance with the presently disclosed subject matter, Lys at position 233 can be replaced with an amino acid such as Arg, Thr, Ala, or His.

In another exemplary embodiment in accordance with the presently disclosed subject matter, Gly at position 234 can be replaced with an amino acid such as Asp, Ile, Leu, Thr, or Arg.

In another exemplary embodiment in accordance with the presently disclosed subject matter, Gly at position 235 can be replaced with an amino acid such as Leu, Glu, Phe, Pro, or Ala.

Exemplary mutations in accordance with the disclosed subject matter can include replacing the Gly residue at position 234 with an Asp residue, replacing Lys-Gly-Gly at positions 233 to 235 with Arg-Ile-Pro, or replacing Gly-Gly-Lys-Gly-Gly at positions 231 to 235 with Arg-Ala-His-Leu-Ala. The last two described mutations can be more advantageous than the first described mutation. Mutations other than those described above can also occur, as long as the properties of the mutant are maintained, for example, amino acids that do not influence the enzymatic activity, can be replaced by one or several other amino acids. "Several" as used herein can include a range of 1 to 20, a range of 1 to 10, or a range of 1 to 5.

Furthermore, mutation of the known mutant of glycerol kinase in which feedback inhibition by FBP is desensitized can be applied to the mutant glycerol kinase in accordance with the presently disclosed subject matter, in addition to the mutations as described above.

For example, the mutation can be the replacement of the Gly at position 231 with another amino acid. (Honisch, C. et. al., Genome Research, 14:2495-502 (2004)). In another exemplary embodiment in accordance with the presently disclosed subject matter, Gly at position 231 can be replaced with an acidic amino acid such as Asp, Glu.

Additionally, the mutation can be the replacement of the Asp at position 73, the Val at position 62, the Met at position 272, the Gln at position 38, the Gly at position 231 with another amino acid. In another exemplary embodiment in accordance with the presently disclosed subject matter, the Asp residue at position 73 can be replaced with Val, the Val residue at position 62 can be replaced with Leu, the Met residue at position 272 can be replaced with Ile, the Gln residue at position 38 can be replaced with Pro, and/or the Gly at position 231 can be replaced with Asp (Herring C. D. et al, Nat. Genet., 38 (12): 1406-1412 (2006). Epub 2006 Nov. 5). Additionally, the 9 bp duplication of nucleotide can be inserted at position 705 in SEQ ID NO. 3, which causes duplication of Lys-Gly-Gly (Herring C. D. et al, Nat. Genet., 38 (12): 1406-1412 (2006). Epub 2006 Nov. 5).

A method for obtaining a mutant gene which encodes such a mutant glycerol kinase can be as follows. The mutant gene can be obtained by randomly introducing a mutation into the glpK gene in vitro, introducing the mutated gene into a bacterium of the Enterobacteriaceae family, and screening for strains which can grow on a medium containing glycerol and which produce an L-amino acid during cultivation in the medium containing glycerol. To screen for a mutant-type glpK gene, a glpK-deficient strain can be used. In vitro mutagenesis of the glpK gene can be performed as follows. First, glpK can be cloned into a plasmid that can replicate in a bacterium of Enterobacteriaceae family and a marker gene such as an antibiotic resistance gene. The obtained glpK gene-carrying plasmid can be dissolved in a buffer containing mutagens, for example, 400 mM hydroxylamine and eacted to introduce a mutation into the glpK gene. After mutagenesis, the plasmid can be desalted with SUPREC-02 (Takara Bio INC.) or the like, and then introduced into a ΔglpK strain with an ability to produce an L-amino acid, and transformants can be screened in a medium containing an antibiotic corresponding to the marker gene. As a control, a glpK gene-carrying plasmid which has not undergone mutagenesis can be introduced into the ΔglpK strain. The transformants which emerge can be inoculated into a medium containing glycerol and cultured with shaking, and then the concentration of the accumulated L-amino acid can be determined. The strain with the mutant glpK gene carried on a plasmid will produce a larger amount of the L-amino acid in the medium than the wild-type strain which contains the plasmid with the wild-type glpK gene. Whether the strain caries a mutant-type glpK gene or not can be confirmed by extracting the plasmid from the strain and determining the nucleotide sequence of the glpK gene.

Alternatively, a mutant-type glpK gene can be obtained by artificially introducing mutations into the glpK gene by methods such as error prone PCR, DNA shuffling, and StEP-PCR (Firth A E, A. E. and Patrick W. M., Bioinformatics, 21, 3314-3315 (2005)).

The methods of introducing a mutation into the glpK gene on the chromosome can include, in addition to the above-mentioned method, mutagenizing spontaneously or by treatment of a bacterium of Enterobacteriaceae family with irradiation of X-rays or ultraviolet rays or with a mutagen such as N-methyl-N'-nitro-N-nitrosoguanidine, and selecting a strain which grows on glycerol faster than a parent strain. Whether the mutant-type glpK gene has been introduced or not can be confirmed by determining the nucleotide sequence of the glpK gene on the chromosome.

Introduction of a mutant glpK gene can include introducing a mutation into a chromosomal glpK gene, introducing a plasmid containing a mutant glpK gene, and replacement of a chromosomal glpK gene with a mutant glpK gene. The method for introduction of mutant glpK can be done by referring to the following method for enhancement of the expression of enzyme.

Furthermore, a bacterium in accordance with the presently disclosed subject matter can be further modified so that the expression of the repressor of glp regulon is attenuated, in addition to desensitization of glycerol kinase. The phrase "repressor of the glp regulon" means the protein encoded by glpR. The glpR gene of E. coli (synonyms: ECK3409, b3423) encodes the repressor of the glycerol-3-phosphate regulon; specifically binding to operator sites of the glpD, glpFK, glpTQ, and glpACB operons. The attenuation of glpR gene can lead to overexpression of the glpACB, glpFK, glpD genes.

The glpR gene (nucleotides complementary to nucleotides in positions 3557870.3558628, GenBank accession no. NC_000913.2.[gi:16131297]) is located between the rtcR gene and the glpT gene on the chromosome of E. coli K-12. The nucleotide sequence of the glpR gene and the amino acid sequence of GlpR encoded by the glpR gene are shown in SEQ ID NO:31 and SEQ ID NO: 32, respectively.

The phrase "attenuation of expression of repressor of the glp regulon" means that the bacterium has been modified in such a way that the modified bacterium contains a reduced amount of the repressor of the glp regulon, as compared with an unmodified bacterium, or is unable to synthesize the repressor of the glp regulon.

The phrase "inactivation of the glpR gene" means that the modified DNA region is unable to naturally express the gene due to a deletion of a part of the gene or deletion of the gene entirely, or the modification of an adjacent region of the gene, including sequences controlling gene expression, such as promoters, enhancers, attenuators, etc.

Expression of the gene can be attenuated by introducing a mutation into the gene on the chromosome so that the intracellular amount of the protein encoded by the gene is decreased as compared to an unmodified strain. Such a mutation can be introduced by insertion of a drug-resistance gene into the target gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the glpR gene also can be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods can be employed to introduce a mutation by gene recombination. A mutant gene can be prepared, and a bacterium can be transformed with a DNA fragment containing the mutant gene. Then, the native gene on the chromosome can be replaced with the mutant gene by homologous recombination, and the resulting strain can be selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). Furthermore, the incorporation of a site-specific mutation by gene substitution using homologous recombination such as set forth above also can be conducted with a plasmid lacking the ability to replicate in the host.

Expression of the gene also can be attenuated by insertion of a transposon or an IS factor into the coding region of the gene (U.S. Pat. No. 5,175,107), or by conventional methods, such as a mutagenesis treatment using UV irradiation or nitrosoguanidine (N-methyl-N'-nitro-N-nitrosoguanidine) treatment.

An exemplary bacterium of the present invention can be further modified so that the activity of a glycerol facilitator is enhanced, in addition to desensitization of glycerol kinase and attenuation of repressor of glp regulon. The glpF gene encoding glycerol facilitator can be a glp regulon, therefore, the activity of glycerol facilitator can be enhanced by the attenuation of glpR gene.

The phrase "the activity of glycerol facilitator is enhanced." means that the bacterium has been modified in such a way that the modified bacterium can have increased activity of said protein(s) per cell, as compared with an unmodified bacterium. Examples of such modifications can include increasing the number of glycerol facilitator molecules per cell, increasing the specific activity per molecule of protein, etc. Furthermore, a wild-type strain that can be used for comparison includes, for example, Escherichia coli K-12. The amount of accumulated L-amino acid, for example, L-threonine, L-lysine, L-histidine, L-phenylalanine, L-arginine, L-tryptophan, or L-glutamic acid, can be increased in a culture medium as the result of enhancing the intracellular activity of one or several proteins of glycerol facilitator.

A glycerol facilitator in accordance with the presently disclosed subject matter can have the function of facilitating diffusion of glycerol into the cell. It can be a member of the major intrinsic protein (MIP) family of transmembrane channel proteins. The activity of glycerol facilitator can be measured by transport assay (Voegele, R. T., Sweet, G. D., and Boos, W. J. Bacteriol. 175:1087-1094 (1993)) The glycerol facilitator activity can be enhanced within a range of not less than 1.5-fold, preferably a range of not less than 2-fold, or within a range of not less than 3-fold as compared to an unmodified strain or a wild-type strain.

The glpF gene of E. coli (synonyms: ECK3919, b3927) can encode the GlpF protein-glycerol facilitator (synonym B3927). The glpF gene (nucleotides complementary to nucleotides in positions 4,115,268 to 4,116,113; GenBank accession no. NC_000913.2; gi: 49175990) is located between the glpK gene and the yliU ORF on the chromosome of E. coli K-12. The nucleotide sequence of the glpF gene and the amino acid sequence of GlpF encoded by the glpF gene are shown in SEQ ID NO: 1 and SEQ ID NO: 2, respectively.

A bacterium in accordance with the presently disclosed subject matter can be further modified so that the activity of glycerol-3-phosphate dehydrogenase is enhanced, in addition to the desensitization of a glycerol kinase, attenuation of glpR, and enhancement of a glycerol facilitator.

Glycerol-3-phosphate dehydrogenase can catalyze the oxidation from glycerol-3-phosphate (G3P) to dihydroxyacetone phosphate (EC 1.1.99.5). The activity of glycerol-3-phosphate dehydrogenase can be measured by the method of Spector and Pizer (Methods Enzymol. 41:249-254 (1975)). The glycerol-3-phosphate dehydrogenase activity can be enhanced within a range of not less than 1.5-fold, within a range of not less than 2-fold, or within a range of not less than 3-fold as compared to an unmodified strain or a wild-type strain.

In E. coli, glycerol-3-phosphate dehydrogenase can be encoded by glpABC and glpD genes.

The glpA gene of E. coli (synonyms: ECK2233, b2241) can encode the GlpA protein-subunit of glycerol 3-phosphate dehydrogenase (anaerobic)(synonym B2241). The glpA gene (nucleotides in positions 2,350,669 to 2,352,297; GenBank accession no. NC_000913.2; gi: 49175990) is located between the glpT gene and the glpB gene on the chromosome of E. coli K-12. The nucleotide sequence of the glpA gene and the amino acid sequence of GlpA encoded by the glpA gene are shown in SEQ ID NO: 5 and SEQ ID NO:6, respectively.

The glpB gene of E. coli (synonyms: ECK2234, psi-51, b2242) can encode the GlpB protein-subunit of glycerol 3-phosphate dehydrogenase (anaerobic)(synonym B2242). The glpB gene (nucleotides in positions 2,352,287 to 2,353,546; GenBank accession no. NC_000913.2; gi: 49175990) is located between the glpA gene and the glpC gene on the chromosome of E. coli K-12. The nucleotide sequence of the glpB gene and the amino acid sequence of GlpB encoded by the glpB gene are shown in SEQ ID NO: 7 and SEQ ID NO:8, respectively.

The glpC gene of E. coli (synonyms: ECK2235, b2243) can encode the GlpC protein-subunit of glycerol 3-phosphate dehydrogenase (anaerobic)(synonym B2243). The glpC gene (nucleotides in positions 2,353,543 to 2,354,733; GenBank accession no. NC_000913.2; gi: 49175990) is located between the glpB gene and the yfaD ORF on the chromosome of E. coli K-12. The nucleotide sequence of the glpC gene and the amino acid sequence of GlpC encoded by the glpC gene are shown in SEQ ID NO: 9 and SEQ ID NO:10, respectively.

The glpD gene of E. coli (synonyms: ECK3412, b3426, glvD, glyD) can encode the GlpD protein-subunit of glycerol 3-phosphate dehydrogenase (aerobic)(synonyms: B3426, GlvD, GlyD). The glpD gene (nucleotides in positions 3,560,036 to 3,561,541; GenBank accession no. NC_000913.2; gi: 49175990) is located between the glpE gene and the yzgL ORF on the chromosome of E. coli K-12. The nucleotide sequence of the glpD gene and the amino acid sequence of GlpD encoded by the glpD gene are shown in SEQ ID NO: 11 and SEQ ID NO: 12, respectively.

A bacterium in accordance with the presently disclosed subject matter can be further modified so that activity of triose phosphate isomerase is enhanced, in addition to the desensitization of a glycerol kinase, attenuation of glpR, enhancement of a glycerol facilitator, and enhancement of glycerol 3-phosphate dehydrogenase.

Triose phosphate isomerase can catalyze reversible conversion between dihydroxyacetone phosphate and glyceraldehydes-3-phosphate (EC:5.3.1.1). The activity of triose phosphate isomerase can be measured by the method of Anderson and Cooper (FEBS Lett. 4: 19-20 (1969)). The triose phosphate isomerase activity can be enhanced within a range of not less than 1.5-fold, within a range of not less than 2-fold, or within a range of not less than 3-fold as compared to an unmodified strain or a wild-type strain.

The tpiA gene of E. coli (synonyms: ECK3911, b3919, G102, tpi) can encode the TpiA protein—triose phosphate isomerase (synonyms: B3946, Tpi). The tpiA gene (nucleotides complementary to nucleotides in positions 4,108,763 to 4,109,530; GenBank accession no. NC_000913.2; gi: 16131757) is located between the cdh gene and the yijQ ORF on the chromosome of E. coli K-12. The nucleotide sequence of the tpiA gene and the amino acid sequence of TpiA encoded by the tpiA gene are shown in SEQ ID NO: 33 and SEQ ID NO: 34, respectively.

Since there can be some differences in DNA sequences between the genera or strains of the Enterobacteriaceae family, the glpF, glpK, glpA, glpB, glpC, glpD, glpR and tpi genes to be modified (or the expression amount thereof to be increased) on the chromosome are not limited to the genes shown in SEQ ID NO: 1, SEQ ID NO: 3, SEQ ID NO: 5, SEQ ID NO: 7, SEQ ID NO: 9, SEQ ID NO: 11, SEQ ID NO: 31 and SEQ ID NO: 33., but may include genes homologous to SEQ ID NO: 1, SEQ ID NO: 3, SEQ ID NO: 5, SEQ ID NO: 7, SEQ ID NO: 9, SEQ ID NO: 11, SEQ ID NO: 31 and SEQ ID NO: 33.

Therefore, the protein variant encoded by the glpF, glpK, glpA, glpB, glpC, glpD, glpR and tpi genes can have a homology range of not less than 80%, a homology range of not less than 90%, or a homology range of not less than 95%, with respect to the entire amino acid sequence shown in SEQ ID NO: 2, SEQ ID NO: 4, SEQ ID NO: 6, SEQ ID NO: 8, SEQ ID NO: 10, SEQ ID NO: 12, SEQ ID NO: 32 and SEQ ID NO: 34 respectively as long as the native activity of the protein is maintained. The phrase "variant protein" as used in in accordance with the presently disclosed subject matter means a protein which has changes in the sequence, whether they are deletions, insertions, additions, or substitutions of amino acids, but still maintains the desired activity at a useful level, for example, useful for the enhanced production of an L-amino acid. The number of changes in the variant protein depends on the position in the three dimensional structure of the protein or the type of amino acid residue. The number of changes can be in a range of 1 to 30, a range of 1 to 15, or a range of 1 to 5. These changes can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Activity of glycerol kinase can be measured by the method described by Hayashi, S. I. and Lin, E. C. (J. Biol. Chem. 242:1030-1035 (1967)). Activity of glycerol 3-phosphate dehydrogenase can be measured by the method described by Kistler, W. S. and Lin, E. C. (J. Bacteriol. 108: 1224-1234 (1971) and J. Bacteriol. 112: 539-547 (1972)).

Moreover, the glpF, glpK, glpA, glpB, glpC, glpD, glpR and tpi genes can be a variant which hybridizes with a complementary strand of the nucleotide sequence shown in SEQ ID NO: 1, SEQ ID NO: 3, SEQ ID NO: 5, SEQ ID NO: 7, SEQ ID NO: 9, SEQ ID NO: 11, SEQ ID NO: 31 and SEQ ID NO: 33, or a probe which can be prepared from the nucleotide sequence under stringent conditions. "Stringent conditions" can include those under which a specific hybrid, for example, a hybrid having homology range of not less than 80%, a homology range of not less than 90%, a homology range of not less than 95%, a homology range of not less than 97%, or a homology range of not less than 98%, is formed and a non-specific hybrid, for example, a hybrid having homology lower than the above, is not formed. For example, stringent conditions can be exemplified by washing one time or more, or two or three times at an exemplary salt concentration of 1×SSC, 0.1% SDS in accordance with the presently disclosed subject matter. This exemplary salt concentration of 0.1× SSC, 0.1% SDS can occur within a first temperature range of 60-68° C., or within a second temperature range of 64-68° C. Duration of washing can depend on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing can be performed 2 to 3 times. The length of the probe can, depend on the hybridization conditions, and can be 100 bp to 1 kbp in an exemplary embodiment in accordance with the presently disclosed subject matter.

Homology between two amino acid sequences can be determined using any method known to one skilled in the art, for example, the computer program BLAST 2.0.

The substitution, deletion, insertion, or addition of one or several amino acid residues can be conservative mutation(s) so that the activity can be maintained. The representative conservative mutation can be a conservative substitution. Examples of conservative substitutions can include: substitution of Ala with Ser or Thr, substitution of Arg with Gln, His, or Lys, substitution of Asn with Glu, Gln, Lys, His, or Asp, substitution of Asp with Asn, Glu, or Gln, substitution of Cys with Ser or Ala, substitution of Gln with Asn, Glu, Lys, His, Asp, or Arg, substitution of Glu with Gly, Asn, Gln, Lys, or Asp, substitution of Gly with Pro, substitution of His with Asn, Lys, Gln, Arg, or Tyr, substitution of Ile with Leu, Met, Val, or Phe, substitution of Leu with Ile, Met, Val, or Phe, substitution of Lys with Asn, Glu, Gln, His, or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, or Leu.

Data comparing the primary sequences of glycerol kinase from *Escherichia coli*, *Shigella sonnei*, *Yersinia pestis*, *Pseudomonas aeruginosa*, and *Bacillus subtilis* show a high level of homology among these proteins (see FIG. 1). From this point of view, substitutions or deletions of the amino acid residues which are identical (marked by asterisk) in all the above-mentioned proteins can be crucial for their function. It is possible to replace similar (indicated by a colon) amino acids residues with the similar amino acid residues without deterioration of the protein activity. But modifications of other non-conserved amino acid residues can not lead to alteration of the activity of glycerol kinase.

In accordance with the presently disclosed subject matter, "the region corresponding to the positions from 233 to 235 of the amino acid sequence of a wild type glycerol kinase shown in SEQ ID NO: 4" means the region of glycerol kinase of interest which corresponds to the positions from 233 to 235 in SEQ ID NO: 4 in the alignment of the amino acid sequences of the objective glycerol kinase and SEQ ID NO: 4. The position of an amino acid residue can change. For example, if an amino acid residue is inserted at the N-terminus portion, the amino acid residue at position 233 can become position 234. In such a case, the amino acid residue at the original position 233 can be designated as the amino acid residue at the position 233 in accordance with the presently disclosed subject matter.

To determine the positions from 233 to 235 of the glycerol kinase of interest, the amino acid sequence of SEQ ID NO: 4 can be aligned with the amino acid sequence of a glycerol kinase of interest, and the L-amino acids at positions from 233 to 235 in the glycerol kinase of interest can be determined.

The DNA which encodes substantially the same protein as shown in SEQ ID NO: 2, SEQ ID NO: 4, SEQ ID NO: 6, SEQ ID NO: 8, SEQ ID NO: 10, SEQ ID NO: 12, SEQ ID NO: 32, and SEQ ID NO: 34 described above can be obtained, for example, by modifying the nucleotide sequence of DNA shown in SEQ ID NO: 1, SEQ ID NO: 3, SEQ ID NO: 5, SEQ ID NO: 7, SEQ ID NO: 9, SEQ ID NO: 11, SEQ ID NO: 31, and SEQ ID NO: 33, respectively, for example, by means of site-directed mutagenesis so that the nucleotide sequence responsible for one or more amino acid residues at a specified site can be deleted, substituted, inserted, or added. DNA modified as described above can be obtained by any mutation treatment(s) known to one skilled in the art. Such treatments can include hydroxylamine treatment of the DNA encoding proteins in accordance with the presently disclosed subject matter, or treatment of the bacterium containing the DNA with UV irradiation or a reagent such as N-methyl-N'-nitro-N-nitrosoguanidine or nitrous acid.

A DNA encoding substantially the same protein as shown in SEQ ID NO: 2, SEQ ID NO: 4, SEQ ID NO: 6, SEQ ID NO: 8, SEQ ID NO: 10, SEQ ID NO: 12, SEQ ID NO: 32, and SEQ ID NO: 34 can be obtained by expressing DNA having a mutation as described above in an appropriate cell, and investigating the activity of any expressed product.

The substitution, deletion, insertion, or addition of nucleotides as described above also can include mutations which naturally occur (mutant or variant), for example, due to variety in the species or genus of bacterium, and which contains the corresponding enzyme.

The phrase "increasing/enhancing the expression of the gene" means that the expression of the gene is increased compared to that of a non-modified strain, for example, a wild-type strain. Examples of such modifications can include increasing the copy number of expressed gene(s) per cell, increasing the expression level of the gene(s), etc.

The quantity of the copy number of an expressed gene can be measured, for example, by restricting the chromosomal DNA followed by Southern blotting using a probe based on the gene sequence, fluorescence in situ hybridization (FISH), and the like. The level of gene expression can be determined by measuring the amount of sRNA transcribed from the gene using various known methods including Northern blotting, quantitative RT-PCR, and the like. The amount of the protein encoded by the gene can be measured by known methods including SDS-PAGE followed by immunoblotting assay (Western blotting analysis), and the like.

Hereinafter, a method for enhancing the activity of glycerol kinase, the glycerol facilitator, glycerol 3-phosphate dehydrogenase, triose phosphate isomerase (hereinafter referred to as glycerol utilization protein) is disclosed.

When using the gene from *Escherichia coli*, the gene encoding glycerol utilization protein can be obtained by PCR (polymerase chain reaction; White, T. J. et al., Trends Genet. 5, 185 (1989)) using primers based on the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 31, and SEQ ID NO: 33. The gene encoding the glycerol utilization protein from another bacterium also can be obtained by PCR from the chromosomal DNA or genomic DNA library of the bacterium using, as primers, oligonucleotides prepared based on the known sequences of the gene of the bacterium or of the gene of another kind of bacterium, or hybridization using an oligonucleotide prepared based on the sequence as a probe. A chromosomal DNA can be prepared from a bacterium that serves as a DNA donor by the method of Saito and Miura (see H. Saito and K. Miura, Biochem. Biophys. Acta, 72, 619 (1963), Experiment Manual for Biotechnology, edited by The Society for Biotechnology, Japan, p 97-98, Baifukan Co., Ltd., 1992) or the like.

Then, a recombinant DNA can be prepared by ligating the gene which has been amplified by PCR to a vector DNA which is capable of functioning in the host bacterium. Examples of the vector capable of functioning in the host bacterium can include vectors autonomously replicable in the host bacterium.

Examples of a vector which is autonomously replicable in *Escherichia coli* can include pUC19, pUC18, pHSG299, pHSG399, pHSG398, pACYC184, (pHSG and pACYC are available from Takara Bio Inc.), RSF1010 (Gene vol. 75(2), p 271-288, 1989), pBR322, pMW219, pMW119 (pMW is available from Nippon Gene Co., Ltd.), pSTV28, and pSTV29 (Takara Bio Inc.). A phage DNA vector also can be used.

To ligate the gene to the above-mentioned vector, the vector can be digested with a restriction enzyme corresponding to a recognition site in the terminus of a DNA fragment containing the gene. Ligation can be performed generally using a ligase such as T4 DNA ligase. Methods of digesting and ligating DNA, preparation of a chromosomal DNA, PCR, preparation of a plasmid DNA, transformation, design of oligonucleotides to be used as primers are methods well known to a person skilled in the art. These methods are described in Sambrook, J., Fritsch, E. F., and Maniatis, T., "Molecular Cloning A Laboratory Manual, Second Edition", Cold Spring Harbor Laboratory Press, (1989), and the like.

The thus-prepared recombinant DNA can be introduced into a bacterium in accordance with a conventional transformation method. Examples of the method can include electroporation (Gliesche, C. G., Can. J. Microbiol., 43, 2, 197-201 (1997)). Also, it is possible to increase the DNA permeability by treating recipient cells with calcium chloride, which has been reported with *Escherichia coli* K-12 (Mandel, M. and Higa, A., J. Mol. Biol., 53, 159 (1970), and introduce a DNA into a competent cell prepared from a cell at proliferation stage, which has been reported with *Bacillus subtilis* (Duncan, C. H., Wilson, G. A and Young, F. E, Gene, 1, 153 (1977)).

The copy number of the gene also can be increased by introducing multiple copies of the genes encoding glycerol utilization protein into the chromosomal DNA of a bacterium. Introduction of multiple copies of the genes into the chromosomal DNA of a bacterium can be attained by homologous recombination using a target sequence present on the chromosomal DNA in multiple copies. Such a sequence present on a chromosomal DNA in multiple copies may be a repetitive DNA or an inverted repeat present on the edge of a transposing element. Alternatively, as disclosed in JP 2-109985 A, multiple copies of a gene can be introduced into the chromosomal DNA by inserting the genes into a transposon, and transferring it so that multiple copies of the gene are integrated into the chromosomal DNA. Integration of these genes into the chromosome can be confirmed by Southern hybridization using a portion of the genes as a probe.

Furthermore, expression of the gene can be enhanced by, as described in WO 00/18935, substituting an expression regulatory sequence such as a promoter of the genes on a chromosomal DNA or of the genes on a plasmid with a stronger promoter, amplifying a regulator that increases expression of the genes, or deleting or attenuating a regulator that decreases expression of the genes. Examples of known strong promoters include the lac promoter, trp promoter, trc promoter, tac promoter, lambda phage $P_R$ promoter, $P_L$ promoter, and tet promoter.

Meanwhile, a promoter of a gene can be made stronger so that expression of the genes is enhanced by introducing nucleotide substitution into the promoter. Examples of a method of evaluating the strength of a promoter and examples of strong promoters are described in Goldstein et al. (Prokaryotic promoters in biotechnology. Biotechnol. Annu. Rev., 1995, 1, 105-128) or the like. In addition, it is known that a spacer sequence between the ribosome binding site (RBS) and translation initiation codon, especially, several nucleotides just upstream of the initiation codon, has a great influence on translation efficiency. Therefore, this sequence can be modified.

In addition, to enhance the activity of a protein encoded by the gene encoding glycerol utilization protein, a mutation that increases the enzymatic activity can be introduced into the genes. Examples of such a mutation can include a mutation in a promoter sequence to increase the transcription level of encoding glycerol utilization protein, and a mutation in the coding region of these genes to increase the specific activities of the glycerol utilization protein.

Furthermore, the glpR gene can encode a repressor of the glp regulon that negatively regulates expression of the gene encodes the glycerol utilization protein, so expression of the gene encoding the glycerol utilization protein can be enhanced by attenuation of expression of the glpR gene.

Methods for preparation of plasmid DNA, digestion and ligation of DNA, transformation, selection of an oligonucleotide as a primer, and the like can be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

Bacteria which are able to produce either an aromatic or a non-aromatic L-amino acids can be used as a bacterium in accordance with the disclosed subject matter which is modified to have enhanced ability to utilize glycerol.

Bacteria in accordance with the disclosed subject matter can be obtained by imparting an enhanced ability to utilize glycerol to a bacterium which inherently has the ability to produce L-amino acids. Alternatively, bacteria in accordance with the disclosed subject matter can be obtained by imparting the ability to produce L-amino acids to a bacterium already having enhanced ability to utilize glycerol.

L-Threonine-Producing Bacteria

Examples of parent strains which can be used to derive the L-threonine-producing bacteria in accordance with the disclosed subject matter can include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain also was deposited in the Russian National Collection of Industrial Microorganisms (VKPM)(Russia, 117545 Moscow, 1 Dorozhny proezd, 1) on Apr. 7, 1987 under the accession number VKPM B-3996.

*E. coli* VKPM B-5318 (EP 0593792B) also can be used as a parent strain for deriving L-threonine-producing bacteria. The strain B-5318 is prototrophic with regard to isoleucine, and a temperature-sensitive lambda-phage $C^1$ repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, bacteria in accordance with the disclosed subject matter can be additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription can be removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

Another example of a parent strain which can be used to derive the L-threonine producing bacteria in accordance with the disclosed subject matter can include the *E. coli* strain MG1655 Δtdh::rhtA* (WO2006/078051).

Another example of a parent strain which can be used to derive the L-threonine producing bacteria in accordance with the disclosed subject matter can include the *E. coli* strain MG1655 Δtdh::rhtA*/PVIC40.

L-Lysine-Producing Bacteria

Examples of L-lysine-producing bacteria belonging to the genus *Escherichia* can include mutants having resistance to an L-lysine analogue. The L-lysine analogue can inhibit growth of bacteria belonging to the genus *Escherichia*, but this inhibition can be fully or partially desensitized when L-lysine is present in the medium. Examples of the L-lysine analogue can include, but are not limited to, oxalysine, lysine hydroxamate, S-(2-aminoethyl)-L-cysteine (AEC), γ-methyllysine, α-chlorocaprolactam, etc. Mutants having resistance to these lysine analogues can be obtained by subjecting bacteria belonging to the genus *Escherichia* to a conventional artificial mutagenesis treatment. Specific examples of bacterial strains useful for producing L-lysine can include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 can be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria in accordance with the disclosed subject matter also can include strains in which expression of one or more genes encoding an L-lysine biosynthetic enzyme are enhanced. Examples of such genes can include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh)(U.S. Pat. No. 6,040,160), phosphoenolpyrvate carboxylase (ppc), aspartate semialdehyde dehydrogeneaes (asd), and aspartase (aspA)(EP 1253195 A). In addition, the parent strains can have an increased level of expression of the gene involved in energy efficiency (cyo)(EP 1170376 A), the gene encoding nicotinamide nucleotide transhydrogenase (pntAB)(U.S. Pat. No. 5,830,716), the ybjE gene (WO2005/073390), or combinations thereof.

Examples of parent strains which can be used to derive L-lysine-producing bacteria in accordance with the disclosed subject matter also can include strains having decreased or no activity of an enzyme that catalyzes a reaction which results in the generation of a compound other than L-lysine, by causing a deviation from the biosynthetic pathway of L-lysine. Examples of the such enzymes can include homoserine dehydrogenase, lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria in accordance with the disclosed subject matter can include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains which can be used to derive L-leucine-producing bacteria in accordance with the disclosed subject matter can include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5, 5-trifluoroleucine (JP 62-34397 B and JP 8-70879 A); *E. coli* strains obtained by the gene engineering method described in WO96/06926; *E. coli* H-9068 (JP 8-70879 A), and the like.

Bacteria in accordance with the disclosed subject matter can be improved by enhancing the expression of one or more genes involved in L-leucine biosynthesis. Examples can include genes of the leuABCD operon, which are preferably represented by a mutant leuA gene coding for isopropylmalate synthase not subject to feedback inhibition by L-leucine (U.S. Pat. No. 6,403,342). In addition, bacteria in accordance with the disclosed subject matter can be improved by enhancing the expression of one or more genes coding for proteins which excrete L-amino acid from the bacterial cell. Examples of such genes include the b2682 and b2683 genes (ygaZH genes)(EP 1239041 A2).

L-Histidine-Producing Bacteria

Examples of parent strains which can be used to derive L-histidine-producing bacteria in accordance with the disclosed subject matter can include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676)(U.S. Pat. No. 6,344, 347); *E. coli* H-9341 (FERM BP-6674)(EP1085087); *E. coli* A180/pFM201 (U.S. Pat. No. 6,258,554) and the like.

Examples of parent strains which can be used to derive L-histidine-producing bacteria in accordance with the disclosed subject matter also can include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), etc.

It is known that the L-histidine biosynthetic enzymes encoded by hisG and hisBHAFI are inhibited by L-histidine, and therefore the L-histidine-producing ability also can be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability can include *E. coli* FERM P-5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), etc.

L-Glutamic Acid-Producing Bacteria

Examples of parent strains which can be used to derive L-glutamic acid-producing bacteria in accordance with the disclosed subject matter can include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parent strains which can be used to derive the L-glutamic acid-producing bacteria in accordance with the disclosed subject matter can include, but are not limited to, strains in which expression of one or more genes encoding an L-glutamic acid biosynthetic enzyme are enhanced. Examples of such genes can include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose 1,6-bisphosphatase (Jbp), phosphofructokinase (pjkA, pjkB), and glucose phosphate isomerase (pgi).

Examples of strains modified so that expression of the citrate synthetase gene, the phosphoenolpyruvate carboxylase gene, and/or the glutamate dehydrogenase gene is/are enhanced can include those disclosed in EP1078989A, EP955368A, and EP952221A.

Examples of parent strains which can be used to derive the L-glutamic acid-producing bacteria in accordance with the disclosed subject matter also can include strains having decreased or eliminated activity of an enzyme that catalyzes synthesis of a compound other than L-glutamic acid by branching off from an L-glutamic acid biosynthesis pathway. Examples of such enzymes can include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* which are deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains can include the following:

E. coli W3110sucA::Km$^R$
E. coli AJ12624 (FERM BP-3853)
E. coli AJ12628 (FERM BP-3854)
E. coli AJ12949 (FERM BP-4881)

E. coli W3110sucA::Km$^R$ is a strain obtained by disrupting the α-ketoglutarate dehydrogenase gene (hereinafter referred to as "sucA gene") of E. coli W3110. This strain is completely deficient in the α-ketoglutarate dehydrogenase.

Other examples of L-glutamic acid-producing bacterium can include those which belong to the genus *Escherichia* and have resistance to an aspartic acid antimetabolite. These strains also can be deficient in the α-ketoglutarate dehydrogenase activity and include, for example, E. coli AJ13199 (FERM BP-5807)(U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria can include mutant strains belonging to the genus *Pantoea* which are deficient in the α-ketoglutarate dehydrogenase activity or have a decreased α-ketoglutarate dehydrogenase activity, and can be obtained as described above. Such strains can include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA, etc. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains which can be used to derive L-phenylalanine-producing bacteria in accordance with the disclosed subject matter can include, but are not limited to, strains belonging to the genus *Escherichia*, such as E. coli AJ12739 (tyrA::Tn10, tyrR)(VKPM B-8197); E. coli HW1089 (ATCC 55371) harboring the mutant pheA34 gene (U.S. Pat. No. 5,354,672); E. coli MWEC101-b (KR8903681); E. coli NRRL B-12141, NRRL B-12145, NRRL B-12146 and NRRL B-12147 (U.S. Pat. No. 4,407, 952). Also, as a parent strain, E. coli K-12 [W3110 (tyrA)/ pPHAB (FERM BP-3566), E. coli K-12 [W3110 (tyrA)/ pPHAD] (FERM BP-12659), E. coli K-12 [W3110 (tyrA)/ pPHATerm] (FERM BP-12662) and E. coli K-12 [W3110 (tyrA)/pBR-aroG4, pACMAB] named as AJ 12604 (FERM BP-3579) can be used (EP 488-424 B1). Furthermore, L-phenylalanine producing bacteria belonging to the genus *Escherichia* with an enhanced activity of the protein encoded by the yedA gene or the yddG gene also can be used (U.S. patent applications 2003/0148473 A1 and 2003/0157667 A1).

L-Tryptophan-Producing Bacteria

Examples of parent strains which can be used to derive the L-tryptophan-producing bacteria in accordance with the disclosed subject matter can include, but are not limited to, strains belonging to the genus *Escherichia*, such as E. coli JP4735/pMU3028 (DSM10122) and JP6015/pMU91 (DSM10123) deficient in the tryptophanyl-tRNA synthetase encoded by mutant trpS gene (U.S. Pat. No. 5,756,345); E. coli SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); E. coli AGX17 (pGX44)(NRRL B-12263) and AGX6(pGX50)aroP (NRRL B-12264) deficient in the enzyme tryptophanase (U.S. Pat. No. 4,371,614); E. coli AGX17/pGX50,pACKG4-pps in which a phosphoenolpyruvate-producing ability is enhanced (WO9708333, U.S. Pat. No. 6,319,696), and the like can be used. L-tryptophan-producing bacteria belonging to the genus *Escherichia* with an enhanced activity of the identified protein encoded by and the yedA gene or the yddG gene also can be used (U.S. patent applications 2003/0148473 A1 and 2003/0157667 A1).

Examples of parent strains which can be used to derive the L-tryptophan-producing bacteria in accordance with the disclosed subject matter also can include strains in which one or more activities of the enzymes anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition can be introduced into these enzymes. Specific examples of strains having such a mutation can include a E. coli SV164 which harbors desensitized anthranilate synthase and a transformant strain obtained by introducing into the E. coli SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria in accordance with the disclosed subject matter also can include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability can be imparted by enhancing expression of a gene which encodes tryptophan synthase, among tryptophan operons (trpBA). The tryptophan synthase consists of a and β subunits which are encoded by the trpA and trpB genes, respectively. In addition, L-tryptophan-producing ability can be improved by enhancing expression of the isocitrate lyase-malate synthase operon (WO2005/103275).

L-Proline-Producing Bacteria

Examples of parent strains which can be used to derive L-proline-producing bacteria oin accordance with the disclosed subject matter can include, but are not limited to, strains belonging to the genus *Escherichia*, such as *E. coli* 702ilvA (VKPM B-8012) which is deficient in the ilvA gene and is able to produce L-proline (EP 1172433). Bacteria in accordance with the disclosed subject matter can be improved by enhancing the expression of one or more genes involved in L-proline biosynthesis. Examples of such genes for L-proline producing bacteria which are preferred can include the proB gene coding for glutamate kinase which is desensitized to feedback inhibition by L-proline (DE Patent 3127361). In addition, bacteria in accordance with the disclosed subject matter can be improved by enhancing the expression of one or more genes coding for proteins excreting L-amino acid from bacterial cell. Such genes can be exemplified by b2682 and b2683 genes (ygaZH genes)(EP1239041 A2).

Examples of bacteria belonging to the genus *Escherichia*, which have an activity to produce L-proline can include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains which can be used to derive L-arginine-producing bacteria in accordance with the disclosed subject matter can include, but are not limited to, strains belonging to the genus *Escherichia*, such as *E. coli* strain 237 (VKPM B-7925)(U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EPI 170361A1), and the like.

Examples of parent strains which can be used to derive L-arginine producing bacteria in accordance with the disclosed subject matter also can include strains in which expression of one or more genes encoding an L-arginine biosynthetic enzyme are enhanced. Examples of such genes can include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains which can be used to derive L-valine-producing bacteria in accordance with the disclosed subject matter can include, but are not limited to, strains which have been modified to overexpress the ilvGMEDA operon (U.S. Pat. No. 5,998,178). The region of the ilvGMEDA operon which is required for attenuation can be removed so that expression of the operon is not attenuated by the L-valine that is produced. Furthermore, the ilvA gene in the operon can be disrupted so that threonine deaminase activity is decreased.

Examples of parent strains which can be used to derive L-valine-producing bacteria in accordance with the disclosed subject matter can include also mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM)(Russia, 117545 Moscow, 1 Dorozhny Proezd, 1) on Jun. 24, 1988 under accession number VKPM B-4411.

Furthermore, mutants requiring lipoic acid for growth and/or lacking H$^+$-ATPase can be also used as parent strains (WO96/06926).

L-Isoleucine-Producing Bacteria

Examples of parent strains which can be used to derive L-isoleucine producing bacteria in accordance with the disclosed subject matter can include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, also can be used as parent strains (JP 2-458 A, FR 0356739, and U.S. Pat. No. 5,998,178).

2. Method of the Present Invention

A method in accordance with the disclosed subject matter can produce an L-amino acid by cultivating bacteria in accordance with the disclosed subject matter in a culture medium containing glycerol to produce and excrete the L-amino acid into the medium, and collecting the L-amino acid from the medium.

In accordance with the disclosed subject matter, the cultivation, collection, and purification of an L-amino acid from the medium, and the like, can be performed in a manner similar to conventional fermentation methods wherein an amino acid can be produced using a bacterium.

A medium used for culture can be either a synthetic or natural medium, so long as the medium includes a carbon source and a nitrogen source and minerals and, if necessary, appropriate amounts of nutrients which the bacterium requires for growth.

As a carbon source, glycerol can be used. Glycerol can be used individually or as a mixture with carbohydrate(s) or sugar(s). Examples of carbohydrates and sugars can include glucose, sucrose, lactose, fructose, maltose, starch. Additionally, cellulose, oils and fats (such as soybean oil, sunflower oil, peanut oil, and coconut fat), fatty acids (such as palmitic acid, stearic acid and linoleic acid), and alcohols (such as, ethanol and methanol) can be used in combination with the above mentioned carbohydrates and sugars. The ratio of glycerol in a total carbon source can be in range of more than 50%, a range of more than 60%, a range of more than 70%, a range of more than 80%, or a range of more than 90%. Alternatively, the ratio of glycerol can be 100%. In an exemplary embodiment in accordance with the disclosed subject matter, the glycerol can be obtained as by-product of biodiesel production (Mu Y, et al, Biotechnol Lett., 28, 1755-91759 (2006), Haas M J, et al; Bioresour Technol. 97, 4, 671-8678 (2006)).

In a method in accordance with the disclosed subject matter, a batch culture, fed-batch culture, and/or a continuous culture can be employed. And, the glycerol in the medium can be regulated to be at a predetermined level in the initial medium, or the feed medium or by using these techniques in combination. The glycerol can be used for both the initial medium and the feed medium, or the carbon source in the feed medium can be different from that used in the initial medium.

As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be explained below in more detail with reference to the following non-limiting Examples.

Reference Example 1

Construction of a Strain Containing Mutant glpK Gene Coding for Glycerol Kinase with the Known Mutation 1. Deletion of the glpK Gene According to the approach described by Yu D. et al., a small deletion (34 bp) in the gene glpK around the site of interest was introduced by the Red-dependent recombination procedure. A strain having a deletion of the glpK gene was constructed by the Red-driven integration. The DNA fragment containing the $Cm^R$ marker encoded by the cat gene was obtained by PCR, using primers P3 (SEQ ID NO: 15) and P4 (SEQ ID NO: 16) and plasmid pMW118-attL-Cm-attR as a template. Primer P3 contains both a region complementary to the 36-nt region of the glpK gene upstream the region of deletion and a region complementary to the attL region. Primer P4 contains both a region complementary to the 35-nt region of the glpK downstream of the region of deletion gene, and a region complementary to the attR region. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1699-bp PCR product (FIG. 2) was obtained and purified in agarose gel and was used for electroporation of the E. coli strain MG1655, which contains the plasmid pKD46. The plasmid pKD46 (Datsenko, K. A. and Wanner, B. L., Proc. Natl. Acad. Sci. USA, 97: 6640-6645 (2000)) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The MG1655 strain is available from the American Type Culture Collection (P.O. Box 1549, Manassas, Va. 20108, 1, United States of America; ATCC700926, ATCC47076).

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 μl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 μg/ml) and grown at 37° C. to select $Cm^R$ recombinants.

Electroporation was performed using 70 μl of cells and ≈100 ng of the PCR product. Cells after electroporation were incubated with 1 ml of SOC medium at 37° C. for 2.5 hours and then were plated onto L-agar containing chloramphenicol (30 μg/ml) and grown at 37° C. to select $Cm^R$ recombinants.

2. Verification of the glpK Gene Deletion by PCR

Figure 3:
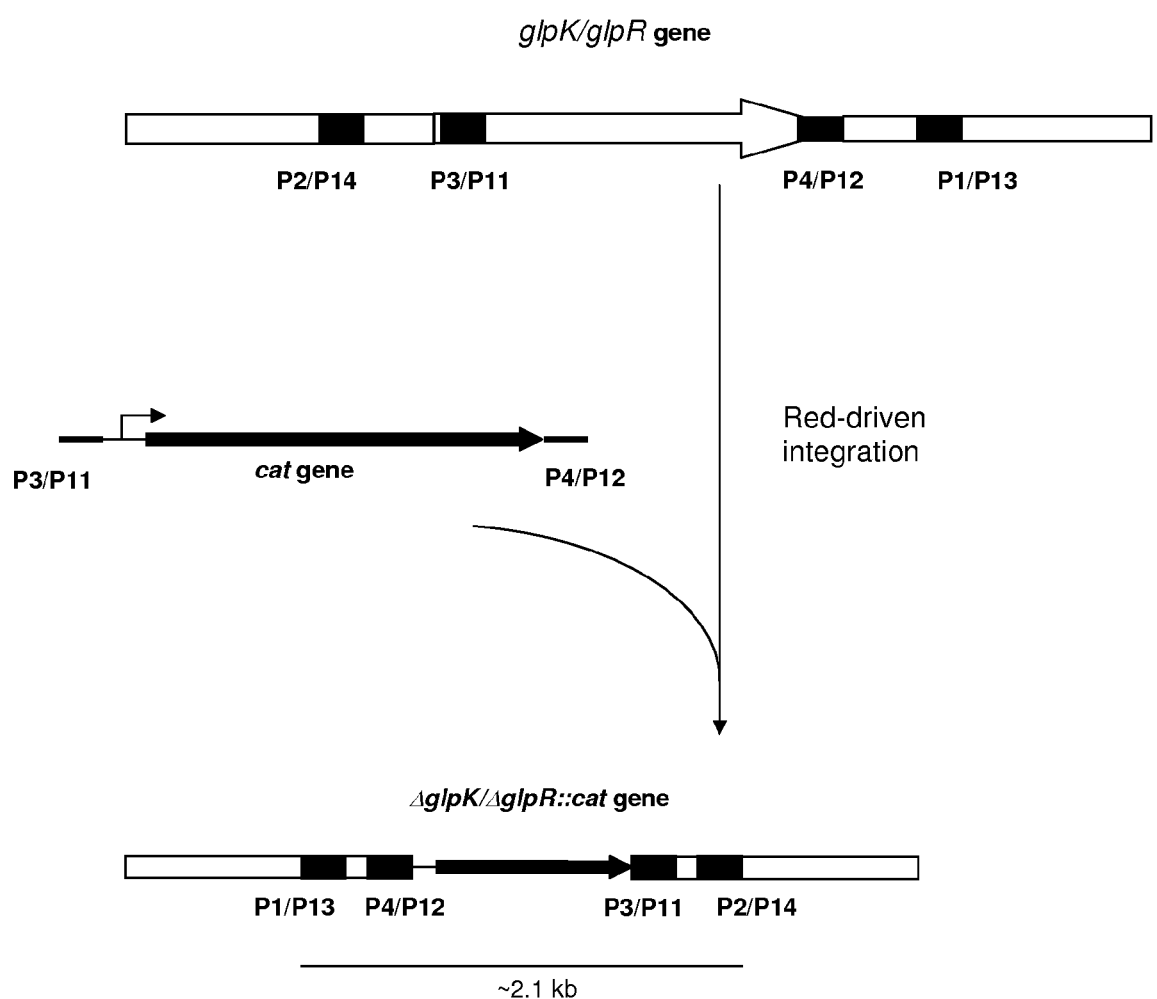
FIG. 3 shows the construction of the chromosomal DNA fragment containing the inactivated glpK/glpR gene.

The mutants having the glpK gene deleted and marked with the Cm resistance gene were verified by PCR. Locus-specific primers P1 (SEQ ID NO: 13) and P2 (SEQ ID NO: 14) were used in PCR for the verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The PCR product obtained in the reaction with the cells of parental glpK$^+$ strain MG1655 as a template, was ~0.4 kbp in length. The PCR product obtained in the reaction with the cells of mutant strain as the template was ~2.1 kbp in length (FIG. 3). The mutant strain was named MG1655 ΔglpK::cat-2. This strain was not able to grow on minimal Adams medium with agar containing glycerol (0.5%) as the sole carbon source and formed white-color colonies on MacConkey agar containing glycerol (0.5%).

3. Construction of strains containing mutant glpK gene coding for glycerol kinase with Gly231Asp substitution A strain containing the glpK gene coding for glycerol kinase with Gly231Asp substitution was constructed by using the Red-driven integration. To introduce G231D substitution the special oligonucleotides with overlapping termini, primers P5 (SEQ ID NO: 17) and P6 (SEQ ID NO: 18) were synthesized. Primers P5 and P6 were used for electroporation of the E. coli strain MG1655ΔglpK::cat-2, which contains the plasmid pKD46. Electrocompetent cells were prepared as described in Example 1. Electroporation was performed using 70 μl of cells and ≈100 ng of P5 and P6 oligonucleotides. Cells after electroporation were incubated with 1 ml of SOC medium at 37° C. for 2.5 hours and then were plated onto minimal Adams medium with agar containing glycerol (0.5%) as the sole carbon source and grown at 37° C. to select recombinants. Several colonies, which were able to grow on glycerol, were selected. All these clones were $Cm^S$ and formed red-color colonies on MacConkey agar containing glycerol(0.5%). Then, to eliminate the pKD46 plasmid, two passages on L-agar at 42° C. were performed and the obtained colonies were tested for sensitivity to ampicillin.

4. Verification of the glpK Gene Mutation Causing Gly231Asp Substitution in Glycerol Kinase The selected recombinants with deletion of the glpK gene were verified by PCR. Locus-specific primers P1 (SEQ ID NO: 13) and P2 (SEQ ID NO: 14) were used in PCR for the verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The obtained PCR product was ~0.4 kbp in length, and that confirmed the presence of the full-length glpK gene in selected recombinants. One of them was chosen for sequence analysis and the presence of the Gly231Asp mutation in glpK gene was confirmed. The mutant strain was named MG1655 glpK*-231.

Example 1

Construction of Strains Containing the Mutant glpK Gene Coding for Glycerol Kinase with the Gly234Asp Substitution 1. Introduction of the glpK gene coding for glycerol kinase with Gly234Asp substitution into the glpK gene-deleted strain A strain containing the glpK gene coding for glycerol kinase with Gly234Asp substitution was constructed by using the Red-driven integration. To introduce the G234D substitution of the special oligonucleotides with overlapping termini, primers P7 (SEQ ID NO: 19) and P8 (SEQ ID NO: 20) were synthesized. Primers P7 and P8 were used for electroporation of the E. coli strain MG1655ΔglpK::cat-2, which contains the plasmid pKD46. Electrocompetent cells were prepared as described in Example 1. Electroporation was performed using 70 µl of cells and ≈100 ng of P7 and P8 oligonucleotides. Cells after electroporation were incubated with 1 ml of SOC medium at 37° C. for 2.5 hours and then were plated onto minimal medium Adams with agar containing glycerol (0.5%) as the sole carbon source and grown at 37° C. to select recombinants. Several colonies, which were able to grow on glycerol, were selected. All these clones were Cm$^S$ and formed red-color colonies on MacConkey agar containing glycerol(0.5%). Then, to eliminate the pKD46 plasmid, two passages on L-agar at 42° C. were performed and the obtained colonies were tested for sensitivity to ampicillin.

2. Verification of the glpK Gene Mutation Causing Gly234Asp Substitution in Glycerol Kinase The selected recombinants with deletion of the glpK gene were verified by PCR. Locus-specific primers P1 (SEQ ID NO: 13) and P2 (SEQ ID NO: 14) were used in PCR for the verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The obtained PCR product was ~0.4 kbp in length, which confirmed presence of full-length glpK gene in selected recombinants. One of them was chosen for sequence analysis and the presence of Gly234Asp mutation in glpK gene was confirmed. The mutant strain was named MG1655 glpK*-234.

Example 2

Construction of Strains Containing Mutant glpK Gene Coding for Glycerol Kinase with Random Substitutions in Positions 231-235

1. Introduction of the glpK gene encoding glycerol kinase having random substitutions into the glpK gene-deleted strain Strains containing the glpK gene coding for glycerol kinase with random substitutions in positions 231-235 were constructed by using the Red-driven integration. To introduce random substitutions in positions 231-234 the special oligonucleotides with overlapping termini, primers P9 (SEQ ID NO: 21) and P10 (SEQ ID NO: 22) were synthesized. Primer P9 has 70 nucleotides and has a region with 7 random nucleotides, depicted in SEQ ID NO: 21 by the letters "h" (for A or C or T), "d" (for A or G or T) and "v" (for A or C or G). Primer P10 has 70 nucleotides and has a region with 7 random nucleotides, depicted in SEQ ID NO: 22 by the letters "h" (for A or C or T), "d" (for A or G or T) and "b" (for C or G or T). Primers P9 and P10 were used for electroporation of the E. coli strain MG1655ΔglpK::cat-2, which contains the plasmid pKD46. Electrocompetent cells were prepared as described in Reference Example 1. Electroporation was performed using 70 µl of cells and ≈100 ng of P9 and P10 oligonucleotides. Cells after electroporation were incubated with 1 ml of SOC medium at 37° C. for 2.5 hours and then were plated onto minimal Adams medium with agar containing glycerol (0.5%) as the sole carbon source and grown at 37° C. to select recombinants. Several colonies, which were able to grow on glycerol, were selected. All these clones were Cm$^S$ and formed red-color colonies on MacConkey agar containing glycerol (0.5%). Then, to eliminate the pKD46 plasmid, two passages on L-agar at 42° C. were performed and the obtained colonies were tested for sensitivity to ampicillin.

2. Sequencing the glpK Gene Mutations Causing Random Substitutions in Positions 231-235 in Glycerol Kinase The selected recombinants with deletion of the glpK gene were verified by PCR. Locus-specific primers P1 (SEQ ID NO:) and P2 (SEQ ID NO: 14) were used in PCR for the verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The obtained PCR product was ~0.4 kbp in length, which confirmed the presence of the full-length glpK gene in selected recombinants. Then selected recombinants were grown in minimal Adams medium containing glycerol (0.5%). Several of them, which utilized glycerol more effectively than other strains, were chosen for sequence analysis. Sequences of 231-235 region of mutated glycerol kinase genes with SEQ ID numbers and corresponding amino acid sequences are shown in Table 1. The general name of strains having substitutions in positions 231-235 in glycerol kinase is MG1655 glpK*-random.

TABLE 1

| Strain | Nucleotide sequence | SEQ ID NOs for nucleotide sequence | Corresponding amino acid sequence | SEQ ID NOs |
|---|---|---|---|---|
| MG1655 | GGC-GGC-AAA-GGC-GGC | 3 (691-705) | Gly-Gly-Lys-Gly-Gly | 48 |
| glpK-234 | GGC-GGC-AAA-GAC-GGC | 27 | Gly-Gly-Lys-Asp-Gly | 49 |

TABLE 1-continued

| Strain | Nucleotide sequence | SEQ ID NOs for nucleotide sequence | Corresponding amino acid sequence | SEQ ID NOs |
|---|---|---|---|---|
| RM-1 | GGC-GGC-AGA-ATA-CTA | 28 | Gly-Gly-Arg-Ile-Leu | 50 |
| RM-3 | GGC-GGC-AGA-CTT-GAA | 29 | Gly-Gly-Arg-Leu-Glu | 51 |
| RM-10 | GGC-GGC-AAA-ACG-TTT | 30 | Gly-Gly-Lys-Thr-Phe | 52 |
| RM-18 | GGC-GGC-AGA-ATA-CCT | 39 | Gly-Gly-Arg-Ile-Pro | 53 |
| RM-19 | GGC-GGC-ACA-TTG-TTA | 40 | Gly-Gly-Thr-Leu-Leu | 54 |
| RM-20 | CGG-GAA-GCT-CGA-GCC | 41 | Arg-Glu-Ala-Arg-Ala | 55 |
| RM-39 | CGA-GCA-CAC-CTT-GCC | 42 | Arg-Ala-His-Leu-Ala | 56 |
| glpK-231 | GAC-GGC-AAA-GGC-GGC | 47 | Asp-Gly-Lys-Gly-Gly | 57 |

Example 3

Production of L-Threonine by *E. coli* Strain MG1655 Δtdh::rhtA*glpK*-234/pVIC40

To test the effect of increased activity of the glycerol kinase on threonine production, a DNA fragment from the chromosome of the above-described *E. coli* MG1655 glpK*-234 was transferred to the threonine-producing *E. coli* strain MG1655 Δtdh::rhtA*/pVIC40 by P1 transduction (Miller, J. H. Experiments in Molecular Genetics, Cold Spring Harbor Lab. Press, 1972, Plainview, N.Y.) to obtain strain MG1655 Δtdh::rhtA* glpK*-234/pVIC40. Construction of the *E. coli* strain MG1655 Δtdh::rhtA*/pVIC40 is described below in the Reference example 2.

Both *E. coli* strains, MG1655 Δtdh::rhtA*/pVIC40 and MG1655 Δtdh::rhtA* glpK*-234/pVIC40, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glycerol. Then, the fermentation medium was inoculated with 0.21 ml (10%) of seed material. The fermentation was performed in 2 ml of minimal medium for fermentation in 20×200-mm test tubes. Cells were grown for 72 hours at 34° C. with shaking at 250 rpm.

After cultivation, the amount of L-threonine which had accumulated in the medium, was determined by paper chromatography using the following mobile phase: butanol–acetic acid–water=4:1:1 (v/v). A solution of ninhydrin (2%) in acetone was used as a visualizing reagent. A spot containing L-threonine was cut out, L-threonine was eluted with 0.5% water solution of $CdCl_2$, and the amount of L-threonine was estimated spectrophotometrically at 540 nm. The results of five independent test tube fermentations are shown in Table 2. As follows from Table 2, MG1655 Δtdh::rhtA* glpK*-234/pVIC40 produced a higher amount of L-threonine, as compared with MG1655 Δtdh::rhtA*/pVIC40.

The composition of the fermentation medium (g/l) was as follows:

| | |
|---|---|
| Glycerol | 60.0 |
| $(NH_4)_2SO_4$ | 31.2 |
| $KH_2PO_4$ | 1.9 |
| $MgSO_4 \cdot 7H_2O$ | 0.63 |
| Thiamine HCl | 0.0002 |
| Mameno (soybean hydrolysate) | 1.36 ml |
| $CaCO_3$ | 20.0 |

Magnesium sulfate were sterilized separately. $CaCO_3$ was sterilized by dry-heat at 180° C. for 2 hours. The pH was adjusted to 7.0.

TABLE 2

| Strain | $OD_{540}$ | Amount of L-threonine, g/l |
|---|---|---|
| MG1655 Δtdh::rhtA*/pVIC40 | 56.5 ± 1.8 | 5.8 ± 0.6 |
| MG1655 Δtdh::rhtA* glpK*-234/pVIC40 | 65.7 ± 2.1 | 7.2 ± 0.3 |

Example 4

Production of L-Threonine by *E. coli* Strain MG1655 Δtdh::rhtA* glpK*-RM18/pVIC40 and MG1655 Δtdh::rhtA* glpK*-RM39/pVIC40

To test the effect of increased activity of the glycerol kinase on threonine production, DNA fragments from the chromosome of the above-described *E. coli* MG1655 glpK*-RM18, *E. coli* MG1655 glpK*-RM39 and *E. coli* MG1655 glpK*-231 were transferred to the threonine-producing *E. coli* strain MG1655 Δtdh::rhtA*/PVIC40 by P1 transduction (Miller, J. H. Experiments in Molecular Genetics, Cold Spring Harbor Lab. Press, 1972, Plainview, N.Y.) to obtain strains MG1655 Δtdh::rhtA* glpK*-RM18/pVIC40, MG1655 Δtdh::rhtA* glpK*-RM39/pVIC40 and MG1655 Δtdh::rhtA* glpK*-231/pVIC40. Construction of the *E. coli* strain MG1655 Δtdh::rhtA*/PVIC40 is described below in the Reference example 2.

*E. coli* strains, MG1655 Δtdh::rhtA*/pVIC40, MG1655 Δtdh::rhtA* glpK*-231/pVIC40, MG1655 Δtdh::rhtA* glpK*-RM18/pVIC40 and MG1655 Δtdh::rhtA* glpK*-RM39/pVIC40, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glycerol. Then, the fermentation medium was inoculated with 0.21 ml (10%) of seed material. The fermentation was performed in 2 ml of minimal medium for fermentation in 20×200-mm test tubes. Cells were grown for 72 hours at 34° C. with shaking at 250 rpm.

After cultivation, the amount of L-threonine which had accumulated in the medium, was determined by paper chromatography using the following mobile phase: butanol–acetic acid–water=4:1:1 (v/v). A solution of ninhydrin (2%) in acetone was used as a visualizing reagent. A spot containing L-threonine was cut out, L-threonine was eluted with 0.5% water solution of $CdCl_2$, and the amount of L-threonine was estimated spectrophotometrically at 540 nm. The results of five independent test tube fermentations are shown in Table 3. As follows from Table 3, MG1655 Δtdh::rhtA* glpK*-RM 18/pVIC40 and MG1655 Δtdh::rhtA* glpK*-RM 39/pVIC40 produced a higher amount of L-threonine, as compared with MG1655 Δtdh::rhtA*/pVIC40 and MG1655 Δtdh::rhtA* glpK*-231/pVIC40.

The composition of the fermentation medium (g/l) was as follows:

| | |
|---|---|
| Glycerol | 60.0 |
| $(NH_4)_2SO_4$ | 31.2 |
| $KH_2PO_4$ | 1.9 |
| $MgSO_4\,7H_2O$ | 0.63 |
| Thiamine HCl | 0.0002 |
| Mameno | 1.36 ml |
| $CaCO_3$ | 20.0 |

Magnesium sulfate was sterilized separately. $CaCO_3$ was sterilized by dry-heat at 180° C. for 2 hours. The pH was adjusted to 7.0.

TABLE 3

| | 48 hours | | 72 hours | |
|---|---|---|---|---|
| Strains | $OD_{540}$ | Thr, g/l | $OD_{540}$ | Thr, g/l |
| MGΔtdh-rhtA*(pVIC40) | 40.3 ± 0.1 | 7.6 ± 0.2 | 39.4 ± 0.2 | 8.7 ± 0.3 |
| MGΔtdh-rhtA*(pVIC40) glpK-RM18 | 19.8 ± 0.1 | 5.8 ± 0.2 | 35.5 ± 0.3 | 13.4 ± 0.5 |
| MGΔtdh-rhtA*(pVIC40) glpK-RM39 | 35.2 ± 0.4 | 10.1 ± 0.4 | 36.3 ± 0.3 | 12.4 ± 0.3 |
| MGΔtdh-rhtA*(pVIC40) glpK-231 | 31.1 ± 0.2 | 10.3 ± 0.3 | 35.2 ± 0.3 | 11.7 ± 0.4 |

Example 5

Production of L-Threonine by *E. coli* Strains B-3996 glpK*-231, and B-3996 glpK*-Random To test the effect of enhanced ability to utilize glycerol on threonine production, DNA fragments from the chromosome of the above-described *E. coli* strains MG1655 glpK*-231 and MG1655 glpK*-random can be transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain the strains B-3996 glpK*-231 and B-3996 glpK*-random, respectively.

*E. coli* strains, B-3996, B-3996 glpK*-231, and B-3996 glpK*-random, can be grown for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% glucose. Then, the fermentation medium can be inoculated with 0.21 ml (10%) of seed material. The fermentation can be performed in 2 ml of minimal medium for fermentation in 20×200-mm test tubes. Cells can be grown for 65 hours at 32° C. with shaking at 250 rpm.

After cultivation, the amount of L-threonine, which had accumulated in the medium, can be determined by paper chromatography using the following mobile phase: butanol–acetic acid–water=4:1:1 (v/v). A solution of ninhydrin (2%) in acetone can be used as a visualizing reagent. A spot containing L-threonine can be cut out, L-threonine can be eluted with 0.5% water solution of $CdCl_2$, and the amount of L-threonine can be estimated spectrophotometrically at 540 nm.

The composition of the fermentation medium (g/l) is as follows:

| | |
|---|---|
| Glycerol | 60.0 |
| $(NH_4)_2SO_4$ | 22.0 |
| NaCl | 0.8 |
| $KH_2PO_4$ | 2.0 |
| $MgSO_4\,7H_2O$ | 0.8 |
| $FeSO_4\,7H_2O$ | 0.02 |
| $MnSO_4\,5H_2O$ | 0.02 |
| Thiamine HCl | 0.0002 |
| Yeast extract | 1.0 |
| $CaCO_3$ | 30.0 |

Glucose and magnesium sulfate are sterilized separately. $CaCO_3$ is sterilized by dry-heat at 180° C. for 2 hours. The pH is adjusted to 7.0. The antibiotic is introduced into the medium after sterilization.

Example 6

Construction of a strain containing mutant glpK gene and an inactivated glpR gene 1. Deletion of the glpR gene A strain having the mutation in the position 231-235 and deletion of the glpR gene is constructed by the Red-driven integration. The DNA fragment containing the $Cm^R$ marker encoded by the cat gene is obtained by PCR, using primers P11 (SEQ ID NO: 23) and P12 (SEQ ID NO: 24) and plasmid pMW118-attL-Cm-attR as a template. Primer P11 contains both a region complementary to the 36-nt region located at the 3' end of the glpR gene and a region complementary to the attL region. Primer P12 contains both a region complementary to the 35-nt region located at the 5' end of the glpR gene and a region complementary to the attR region. Conditions for PCR are as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1699-bp PCR product (FIG. 2) is obtained and purified in agarose gel and is used for electroporation of the *E. coli* strain MG1655, which contains the plasmid pKD46.

Electrocompetent cells are prepared as described in Reference Example 1. Electroporation is performed using 70 μl of cells and ≈100 ng of the PCR product. Cells after electroporation are incubated with 1 ml of SOC medium at 37° C. for 2.5 hours and then are plated onto L-agar containing chloramphenicol (30 μg/ml) and grown at 37° C. to select $Cm^R$ recombinants. Then, to eliminate the pKD46 plasmid, two passages on L-agar with Cm at 42° C. is performed and the obtained colonies are tested for sensitivity to ampicillin.

2. Verification of the glpR Gene Deletion by PCR

The mutants having the glpR gene deleted and marked with the Cm resistance gene are verified by PCR. Locus-specific primers P13 (SEQ ID NO: 25) and P14 (SEQ ID NO: 26) are used in PCR for the verification. Conditions for PCR verification are as follows: denaturation step for 3 min at 94° C.; profile for 30 cycles: 30 sec at 94° C., 30 sec at 54° C., 1 min at 72° C.; final step: 7 min at 72° C. The PCR product obtained in the reaction with the cells of parental glpR$^+$ strain MG1655 as a template, is ~1.1 kbp in length. The PCR product obtained in the reaction with the cells of mutant strain as the template is ~2.1 kbp in length (FIG. 3). The mutant strain is named MG1655 ΔglpR glpK*-234.

3. Utilization of glycerol by E. coli MG1655 ΔglpR glpK*-234

Overnight cultures of *E. coli* strains MG1655 and MG1655ΔglpR glpK*-234 are grown at 37° C. in LB broth, and the cultures are washed with NaCl(9%) and diluted 100 times with 5 ml of minimal Adams medium containing glycerol (0.5%) in 20×200-mm test tubes. The tubes with cultures are incubated at 37° C. with shaking at 240 rpm. Periodically aliquots of cultures are taken and optical density of cells is measured spectrophotometrically at 540 nm.

Example 7

Production of L-threonine by E. coli strain B-3996 glpK*-234-ΔglpR

To test the effect of the combination glpK mutation and deletion of the glpR gene on threonine production, DNA fragments from the chromosome of the above-described *E. coli* MG1655 glpK*ΔglpR can be transferred to the threonine-producing *E. coli* strain VKPM B-3996 glpK*-234 by P1 transduction to obtain the strain B-3996 glpK*-234-ΔglpR. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1 Dorozhny proezd, 1) under the accession number B-3996.

Both *E. coli* strains, B-3996 and B-3996-glpK*-234, and B-3996 glpK*-234-ΔglpR are grown for 18-24 hours at 37° C. on L-agar plates. To obtain a seed culture, the strains are grown on a rotary shaker (250 rpm) at 32° C. for 18 hours in 20×200-mm test tubes containing 2 ml of L-broth supplemented with 4% glycerol. Then, the fermentation medium is inoculated with 0.21 ml (10%) of seed material. The fermentation is performed in 2 ml of minimal medium for fermentation in 20×200-mm test tubes. Cells are grown for 72 hours at 34° C. with shaking at 250 rpm.

After cultivation, the amount of L-threonine which accumulates in the medium, is determined by paper chromatography using the following mobile phase: butanol–acetic acid–water=4:1:1 (v/v). A solution of ninhydrin (2%) in acetone is used as a visualizing reagent. A spot containing L-threonine is cut out, L-threonine is eluted with 0.5% water solution of CdCl$_2$, and the amount of L-threonine is estimated spectrophotometrically at 540 nm. The composition of the fermentation medium (g/l) is as follows:

| | |
|---|---|
| (NH$_4$)$_2$SO$_4$ | 22.0 |
| NaCl | 0.8 |
| MgSO$_4$ 7H$_2$O | 0.8 |
| Fe SO$_4$ | 0.02 |
| Mn SO$_4$ | 0.02 |
| K$_2$HPO$_4$ | 2.0 |
| Thiamine HCl | 0.0002 |
| Yeast extract | 1.0 |
| CaCO$_3$ | 30.0 |
| Glycerol | 80.0 |

Magnesium sulfate is sterilized separately. CaCO$_3$ is sterilized by dry-heat at 180° C. for 2 hours. The pH is adjusted to 7.0.

Example 8

Production of L-Lysine by E. coli Strain AJ11442 glpK*-234 or AJ11442 glpK*-Random or AJ11442 glpK*ΔglpR To test the effect of enhanced ability to utilize glycerol on lysine production, DNA fragments from the chromosome of the above-described *E. coli* strain MG1655 glpK*-231, MG1655 glpK*-234, MG1655 glpK*-random, or MG1655 ΔglpR can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain the strain AJ11442 glpK*-231, AJ11442 glpK*-234, AJ11442 glpK*-random, or AJ11442 glpK*-ΔglpR, respectively. The strain AJ14442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

*E. coli* strains, AJ11442, AJ11442 glpK*-231, AJ11442 glpK*-234, AJ11442 glpK*-random, and AJ11442 glpK*-ΔglpR, can be cultured in L-medium at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glycerol | 60.0 |
| (NH$_4$)$_2$SO$_4$ | 24 |
| K$_2$HPO$_4$ | 1.0 |
| MgSO$_4$ 7H$_2$O | 1.0 |
| FeSO$_4$ 7H$_2$O | 0.01 |
| MnSO$_4$ 5H$_2$O | 0.01 |
| Yeast extract | 2.0 |

The pH is adjusted to 7.0 by KOH and the medium is autoclaved at 115° C. for 10 min. Glucose and MgSO$_4$ 7H$_2$O are sterilized separately. CaCO$_3$ is dry-heat sterilized at 180° C. for 2 hours and added to the medium for a final concentration of 30 μl.

Example 9

Production of L-cysteine by E. coli strains JM15(ydeD) glpK*-234, JM15(ydeD) glpK*-random or JM15(ydeD) glpK*-ΔglpR To test the effect of enhanced ability to utilize glycerol on L-cysteine production, DNA fragments from the chromosome of the above-described E. coli strain MG1655 glpK*-231, MG1655 glpK*-234, MG1655 glpK*-random or MG1655 glpK*-ΔglpR can be transferred to the E. coli L-cysteine-producing strain JM15(ydeD) by P1 transduction (Miller, J. H. Experiments in Molecular Genetics, Cold Spring Harbor Lab. Press, 1972, Plainview, N.Y.) to obtain the strains JM15(ydeD) glpK*-231, JM15(ydeD) glpK*-234, JM15(ydeD) glpK*-random and JM15(ydeD) glpK*-ΔglpR, respectively.

E. coli strain JM15(ydeD) is a derivative of E. coli strain JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663). The strain JM15 (CGSC# 5042) can be obtained from The Coli Genetic Stock Collection at the E. coli Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 10

Production of L-leucine by E. coli strains 57 glpK*-234 or 57 glpK*-random or E. coli strains 57 glpK*-ΔglpR To test the effect of the enhanced ability to utilize glycerol on L-leucine production, DNA fragments from the chromosome of the above-described E. coli strain MG1655 glpK*-231, MG1655 glpK*-234, MG1655 glpK*-random, or MG1655 glpK*-ΔglpR can be transferred to the E. coli L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57 glpK*-231, 57 glpK*-234, 57 glpK*-random, or 57 ΔglpR. The strain 57 has been deposited in the Russian National Collection of Industrial Microorganisms (VKPM)(Russia, 117545 Moscow, 1 Dorozhny proezd, 1) on May 19, 1997 under accession number VKPM B-7386, respectively.

E. coli strains, 57, 57 glpK*-231, 57 glpK*-234, 57 glpK*-random, and 57 glpK*-ΔglpR, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% glycerol. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol–acetic acid–water=4:1:1).

The composition of the fermentation medium (g/l)(pH 7.2) is as follows:

| | |
|---|---|
| Glycerol | 60.0 |
| (NH$_4$)$_2$SO$_4$ | 25.0 |
| K$_2$HPO$_4$ | 2.0 |
| MgSO$_4$ 7H$_2$O | 1.0 |
| Thiamine | 0.01 |
| CaCO$_3$ | 25.0 |

Glucose and CaCO$_3$ are sterilized separately.

Example 11

Production of L-histidine by E. coli strains 80 glpK*-234 or 80 glpK*-random or 80 glpK*-ΔglpR To test the effect of the enhanced ability to utilize glycerol on L-histidine production, DNA fragments from the chromosome of the above-described E. coli strain MG1655 glpK*-231, MG1655 glpK*-234, MG1655 glpK*-random, or MG1655-glpK*-ΔglpR can be transferred to the histidine-producing E. coli strain 80 by P1 transduction (Miller, J. H. Experiments in Molecular Genetics, Cold Spring Harbor Lab. Press, 1972, Plainview, N.Y.) to obtain the strain 80 glpK*-231, 80 glpK*-234, 80 glpK*-random, or 80 ΔglpR, respectively. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

E. coli strains, 80, 80 glpK*-231, 80 glpK*-234, 80 glpK*-random, and 80 glpK*-ΔglpR, can be cultured in L-broth supplemented with 4% glycerol for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glycerol | 60.0 |
| Mameno (soybean hydrolysate) | 0.2 of as total nitrogen |
| -proline | 1.0 |
| (NH$_4$)$_2$SO$_4$ | 25.0 |
| KH$_2$PO$_4$ | 2.0 |
| MgSO$_4$ 7H$_2$0 | 1.0 |
| FeSO$_4$ 7H$_2$0 | 0.01 |
| MnSO$_4$ | 0.01 |
| Thiamine | 0.001 |
| Betaine | 2.0 |
| CaCO$_3$ | 60.0 |

Glucose, proline, betaine and CaCO$_3$ are sterilized separately. The pH is adjusted to 6.0 before sterilization.

Example 12

Production of L-glutamate by E. coli strains VL334thrC+glpK*-234 or VL334thrC+ glpK*-random or VL334thrC+ glpK*-ΔglpR To test the effect of enhanced ability to utilize glycerol on L-glutamate production, DNA fragments from the chromosome of the above-described E. coli strain MG1655 glpK*-231, MG1655 glpK*-234, MG1655 glpK*-random, and MG1655 glpK*-ΔglpR can be transferred to the E. coli L-glutamate-producing strain VL334thrC+(EP 1172433) by P1 transduction (Miller, J. H. Experiments in Molecular Genetics, Cold Spring Harbor Lab. Press, 1972, Plainview, N.Y.) to obtain the strain VL334thrC+glpK*-231, VL334thrC+glpK*-234, VL334thrC+glpK*-random, or VL334thrC+ ΔglpR, respectively. The strain VL334thrC+ has been deposited in the Russian National Collection of Industrial Microorganisms (VKPM)(Russia, 117545 Moscow, 1 Dorozhny proezd, 1) on Dec. 6, 2004 under the accession number B-8961 and then converted to a deposit under the Budapest Treaty on Dec. 8, 2004.

E. coli strains, VL334thrC+, VL334thrC+glpK*-231, VL334thrC+glpK*-234, VL334thrC+glpK*-random, and VL334thrC+glpK*-ΔglpR, can be grown for 18-24 hours at 37° C. on L-agar plates. Then, one loop of the cells can be transferred into test tubes containing 2 ml of fermentation medium. The fermentation medium contains glycerol (60 μl), ammonium sulfate (25 μl), KH$_2$PO$_4$ (2 g/l), MgSO$_4$ (1 μl), thiamine (0.1 mg/ml), L-isoleucine (70 μg/ml), and CaCO$_3$ (25 μl). The pH is adjusted to 7.2. Glycerol and CaCO$_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% CdCl$_2$.

Example 13

Production of L-phenylalanine by E. coli strains AJ12739 glpK*-234, AJ12739 glpK*-random or AJ12739 glpK*-ΔglpR To test the effect of enhanced ability to utilize glycerol on L-phenylalanine production, DNA fragments from the chromosome of the above-described E. coli strain MG1655 glpK*-231, MG1655 glpK*-234, MG1655 glpK*-random, or MG1655 glpK*-ΔglpR can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain the strain AJ12739 glpK*-231, AJ12739 glpK*-234, AJ12739 glpK*-random, or AJ12739 AglpR, respectively. The strain AJ12739 has been deposited in the Russian National Collection of Industrial Microorganisms (VKPM)(Russia, 117545 Moscow, 1 Dorozhny proezd, 1) on Nov. 6, 2001 under accession no. VKPM B-8197 and then converted to a deposit under the Budapest Treaty on Aug. 23, 2002.

E. coli strains, AJ12739, AJ12739 glpK*-231, AJ12739 glpK*-234, AJ12739 glpK*-random, and AJ12739 glpK*-ΔglpR, can be cultivated at 37° C. for 18 hours in a nutrient broth supplemented with 4% glycerol, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glycerol | 60.0 |
| (NH$_4$)$_2$SO$_4$ | 16.0 |
| K$_2$HPO$_4$ | 0.1 |
| MgSO$_4$ 7H$_2$O | 1.0 |
| FeSO$_4$ 7H$_2$O | 0.01 |
| MnSO$_4$ 5H$_2$O | 0.01 |
| Thiamine HCl | 0.0002 |
| Yeast extract | 2.0 |
| Tyrosine | 0.125 |
| CaCO$_3$ | 20.0 |

Glucose and magnesium sulfate are sterilized separately. CaCO$_3$ is dry-heat sterilized at 180° C. for 2 hours. The pH is adjusted to 7.0.

Example 14

Production of L-tryptophan by E. coli strains SV164(pGH5) glpK*-234 or SV164(pGH5) glpK*-random or SV164(pGH5) glpK*-ΔglpR To test the effect of enhanced ability to utilize glycerol on L-tryptophan production, DNA fragments from the chromosome of the above-described E. coli strain MG1655 glpK*-231, MG1655 glpK*-234, MG1655 glpK*-random, or MG1655 glpK*-ΔglpR can be transferred to the tryptophan-producing E. coli strain SV164 (pGH5) by P1 transduction (Miller, J. H. Experiments in Molecular Genetics, Cold Spring Harbor Lab. Press, 1972, Plainview, N.Y.) to obtain the strain SV164(pGH5) glpK*-231, SV164(pGH5) glpK*-234, SV164(pGH5) glpK*-random, or SV164(pGH5) ΔglpR, respectively. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143.

E. coli strains, SV164(pGH5), SV164(pGH5) glpK*-231, SV164(pGH5) glpK*-234, SV164(pGH5) glpK*-random, and SV164(pGH5) glpK*-ΔglpR, can be cultivated with shaking at 32° C. for 18 hours in 3 ml of nutrient broth supplemented with tetracycline (10 mg/ml, marker of pGH5 plasmid) and 4% glycerol. The obtained cultures (0.3 ml each) can be inoculated into 3 ml of a fermentation medium containing tetracycline (10 mg/ml) in 20×200-mm test tubes, and cultivated at 32° C. for 72 hours with a rotary shaker at 250 rpm. After cultivation, the amount of tryptophan which accumulates in the medium can be determined by TLC as described in Example 12.

The fermentation medium components are listed in Table 4, but should be sterilized in separate groups (A, B, C, D, E, F, and G), as shown, to avoid adverse interactions during sterilization.

TABLE 4

| Solutions | Component | Final concentration, g/l |
|---|---|---|
| A | KH$_2$PO$_4$ | 0.28 |
|   | NaCl | 0.14 |
|   | (NH$_4$)$_2$SO$_4$ | 16 |
|   | L-Methionine | 0.08 |
|   | L-Phenylalanine | 0.28 |
|   | L-Tyrosine | 0.28 |
|   | Mameno (total N) | 0.07 |
| B | Glucose | 40.0 |
|   | MgSO$_4$•7H$_2$O | 0.03 |
| C | FeSO$_4$•7H$_2$O | 0.03 |
| D | Na$_2$MoO$_4$•2H$_2$O | 0.00015 |
|   | H$_3$BO$_3$ | 0.0025 |
|   | CoCl$_2$•6H$_2$O | 0.00007 |
|   | CuSO$_4$•5H$_2$O | 0.00025 |
|   | MnCl$_2$•4H$_2$O | 0.0016 |
|   | ZnSO$_4$•7H$_2$O | 0.0003 |
| E | Thiamine HCl | 0.001 |
| F | CaCO$_3$ | 30.0 |
| G | Pyridoxine | 0.03 |

The pH of solution A is adjusted to 7.1 with NH$_4$OH.

Example 15

Production of L-proline by E. coli strains 702ilvA glpK*-234 or 702ilvA glpK*-random or 702ilvA glpK*-ΔglpR To test the effect of enhanced ability to utilize glycerol on L-proline production, DNA fragments from the chromosome of the above-described E. coli strain MG1655 glpK*-231, MG1655 glpK*-234, MG1655 glpK*-random, or MG1655_glpK*-ΔglpR can be transferred to the proline-producing E. coli strain 702ilvA by P1 transduction (Miller, J. H. Experiments in Molecular Genetics, Cold Spring Harbor Lab. Press, 1972, Plainview, N.Y.) to obtain the strain 702ilvA glpK*-231, 702ilvA glpK*-234, 702ilvA glpK*-random, or 702ilvA ΔglpR, respectively. The strain 702ilvA has been deposited in the Russian National Collection of Industrial Microorganisms (VKPM)(Russia, 117545 Moscow, 1 Dorozhny proezd, 1) on Jul. 18, 2000 under accession number VKPM B-8012 and then converted to a deposit under the Budapest Treaty on May 18, 2001.

E. coli strains, 702ilvA, 702ilvA glpK*-231, 702ilvA glpK*-234, 702ilvA glpK*-random, and 702ilvA glpK*-ΔglpR, can be grown for 18-24 hours at 37° C. on L-agar plates. Then, these strains can be cultivated under the same conditions as in Example 11.

Example 16

Production of L-arginine by E. coli strains 382 glpK*-234 or 382 glpK*-random or 382-glpK*-ΔglpR To test the effect of enhanced ability to utilize glycerol on L-arginine production, DNA fragments from the chromosome of the above-described E. coli strain MG1655 glpK*-231, MG1655 glpK*-234, MG1655 glpK*-random, or MG1655 glpK*-ΔglpR can be transferred to the arginine-producing E. coli strain 382 by P1 transduction (Miller, J. H. Experiments in Molecular Genetics, Cold Spring Harbor Lab. Press, 1972, Plainview, N.Y.) to obtain the strain 382 glpK*-231, 382 glpK*-234, 382 glpK*-random, or 382 ΔglpR, respectively. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

E. coli strains, 382, 382 glpK*-231, 382 glpK*-234, 382 glpK*-random, and 382 glpK*-ΔglpR, can be cultivated with shaking at 37° C. for 18 hours in 3 ml of nutrient broth supplemented with 4% glycerol, and 0.3 ml of the obtained cultures can be inoculated into 2 ml of a fermentation medium in 20×200-mm test tubes and cultivated at 32° C. for 48 hours on a rotary shaker.

After the cultivation, the amount of L-arginine which had accumulated in the medium can be determined by paper chromatography using the following mobile phase:butanol:acetic acid:water=4:1:1 (v/v). A solution of ninhydrin (2%) in acetone can be used as a visualizing reagent. A spot containing L-arginine can be cut out, L-arginine can be eluted with 0.5% water solution of CdCl$_2$, and the amount of L-arginine can be estimated spectrophotometrically at 540 nm.

The composition of the fermentation medium (g/l) is as follows:

| | |
|---|---|
| Glycerol | 60.0 |
| (NH$_4$)$_2$SO$_4$ | 35.0 |
| KH$_2$PO$_4$ | 2.0 |
| MgSO$_4$ 7H$_2$O | 1.0 |
| Thiamine HCl | 0.0002 |
| Yeast extract | 1.0 |
| L-isoleucine | 0.1 |
| CaCO3 | 5.0 |

Glucose and magnesium sulfate are sterilized separately. CaCO$_3$ is dry-heat sterilized at 180° C. for 2 hours. The pH is adjusted to 7.0.

Reference example 2. Construction of the E. coli strain MG1655 Δtdh::rhtA*/pVIC40.

The L-threonine producing E. coli strain MG1655 Δtdh, rhtA* (pVIC40) was constructed by inactivation of the native tdh gene in E. coli MG1655 using the cat gene followed by introduction of an rhtA23 mutation which confers resistance to high concentrations of threonine (>40 mg/ml) and homoserine (>5 mg/ml). Then, the resulting strain was transformed with plasmid pVIC40 from E. coli VKPM B-3996. Plasmid pVIC40 is described in detail in U.S. Pat. No. 5,705,371.

To replace the native tdh gene, a DNA fragment carrying the chloramphenicol resistance marker (Cm$^R$) encoded by the cat gene was integrated into the chromosome of E. coli MG1655 (ATCC 700926) in place of the native tdh gene by the method described by Datsenko K. A. and Wanner B. L. (Proc. Natl. Acad. Sci. USA, 2000, 97, 6640-6645) which is also called "Red-mediated integration" and/or "Red-driven integration". The recombinant plasmid pKD46 (Datsenko, K. A., Wanner, B. L., Proc. Natl. Acad. Sci. USA, 2000, 97, 6640-6645) with the thermo sensitive replicon was used as the donor of the phage λ-derived genes responsible for the Red-mediated recombination system. E. coli BW25113 containing the recombinant plasmid pKD46 can be obtained from the E. coli Genetic Stock Center, Yale University, New Haven, USA, the accession number of which is CGSC7630.

A DNA fragment containing a Cm$^R$ marker encoded by the cat gene was obtained by PCR using the commercially available plasmid pACYC184 (GenBank/EMBL accession number X06403, "Fermentas", Lithuania) as the template, and primers P15 (SEQ ID NO: 35) and P16 (SEQ ID NO: 36). Primer P15 contains 35 nucleotides homologous to the 5'-region of the tdh gene introduced into the primer for further integration into the bacterial chromosome. Primer P16 contains 32 nucleotides homologous to the 3'-region of the tdh gene introduced into the primer for further integration into the bacterial chromosome.

PCR was provided using the "Gene Amp PCR System 2700" amplificatory (Applied Biosystems). The reaction mixture (total volume—50 µl) consisted of 5 µl of 10×PCR-buffer with 25 mM MgCl$_2$ ("Fermentas", Lithuania), 200 µM each of dNTP, 25 µmol each of the exploited primers and 1 U of Taq-polymerase ("Fermentas", Lithuania). Approximately 5 ng of the plasmid DNA was added in the reaction mixture as a template DNA for the PCR amplification. The temperature profile was the following: initial DNA denaturation for 5 min at 95° C., followed by 25 cycles of denaturation at 95° C. for 30 sec, annealing at 55° C. for 30 sec, elongation at 72° C. for 40 sec; and the final elongation for 5 min at 72° C. Then, the amplified DNA fragment was purified by agarose gel-electrophoresis, extracted using "GenElute Spin Columns" (Sigma, USA), and precipitated by ethanol.

The obtained DNA fragment was used for electroporation and Red-mediated integration into the bacterial chromosome of the E. coli MG1655/pKD46. Electrocompetent cells were prepared as described in Reference Example 1.

Electroporation was performed by "Bio-Rad" electroporator (USA)(No. 165-2098, version 2-89) according to the manufacturer's instructions. Shocked cells were added to 1-ml of SOC medium (Sambrook et al, "Molecular Cloning A Laboratory Manual, Second Edition", Cold Spring Harbor Laboratory Press (1989)), incubated for 2 hours at 37° C., and then were spread onto L-agar containing 25 µg/ml of chloramphenicol. Colonies grown for 24 hours were tested for the presence of Cm$^R$ marker instead of the native tdh gene by PCR using primers P17 (SEQ ID NO: 37) and P18 (SEQ ID NO: 38). For this purpose, a freshly isolated colony was suspended in 20 µl water and then 1 µl of obtained suspension was used for PCR. The temperature profile follows: initial DNA denaturation for 5 min at 95° C.; then 30 cycles of denaturation at 95° C. for 30 sec, annealing at 55° C. for 30 sec and elongation at 72° C. for 30 sec; the final elongation for 5 min at 72° C. A few Cm$^R$ colonies tested contained the desired 1104 bp DNA fragment, confirming the presence of Cm$^R$ marker DNA instead of 1242 bp fragment of tdh gene. One of the obtained strains was cured of the thermosensitive plasmid pKD46 by culturing at 37° C. and the resulting strain was named E. coli MG1655Δtdh.

Then, the rhtA23 mutation from the strain VL614rhtA23 (Livshits V. A. et al, 2003, Res. Microbiol., 154:123-135) was introduced into the obtained strain MG1655 Δtdh resulting in strain MG1655 Δtdh, rhtA*. The rhtA23 is a mutation which confers resistance to high concentrations of threonine (>40 mg/ml) and homoserine (>5 mg/ml). For that purpose the strain MG1655 Δtdh was infected with phage P1$_{vir}$ grown on the donor strain VL614rhtA23. The transductants were selected on M9 minimal medium containing 8 mg/ml homoserine and 0.4% glucose as the sole carbon source.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

Explanation of Sequence Listing

SEQ ID NO: 1 nucleotide sequence of glpF
SEQ ID NO: 2 amino acid seqeunce of GlpF
SEQ ID NO: 3 nucleotide sequence of glpK
SEQ ID NO: 4 amino acid seqeunce of glycerol kinase
SEQ ID NO: 5 nucleotide sequence of glpA
SEQ ID NO: 6 amino acid seqeunce of GlpA
SEQ ID NO: 7 nucleotide sequence of glpB
SEQ ID NO: 8 amino acid seqeunce of GlpB
SEQ ID NO: 9 nucleotide sequence of glpC
SEQ ID NO: 10 amino acid seqeunce of GlpC
SEQ ID NO: 11 nucleotide sequence of glpD
SEQ ID NO: 12 amino acid seqeunce of GlpD
SEQ ID NO: 13 primer P1
SEQ ID NO: 14 primer P2
SEQ ID NO: 15 primer P3
SEQ ID NO: 16 primer P4
SEQ ID NO: 17 primer P5
SEQ ID NO: 18 primer P6
SEQ ID NO: 19 primer P7
SEQ ID NO: 20 primer P8
SEQ ID NO: 21 primer P9
SEQ ID NO: 22 primer P10
SEQ ID NO: 23 primer P11
SEQ ID NO: 24 primer P12
SEQ ID NO: 25 primer P13
SEQ ID NO: 26 primer P14
SEQ ID NO: 27 DNA fragment coding 231-235 region of GlpK
SEQ ID NO: 28 DNA fragment coding 231-235 region of GlpK
SEQ ID NO: 29 DNA fragment coding 231-235 region of GlpK
SEQ ID NO: 30 DNA fragment coding 231-235 region of GlpK
SEQ ID NO: 31 nucleotide sequence of glpR
SEQ ID NO: 32 amino acid seqeunce of GlpR
SEQ ID NO: 33 nucleotide sequence of tpiA
SEQ ID NO: 34 amino acid seqeunce of TpiA
SEQ ID NO: 35 primer P15
SEQ ID NO: 36 primer P16
SEQ ID NO: 37 primer P17
SEQ ID NO: 38 primer P18
SEQ ID NO: 39 DNA fragment coding 231-235 region of GlpK
SEQ ID NO: 40 DNA fragment coding 231-235 region of GlpK
SEQ ID NO: 41 DNA fragment coding 231-235 region of GlpK
SEQ ID NO: 42 DNA fragment coding 231-235 region of GlpK
SEQ ID NO: 43 amino acid seqeunce of glycerol kinase from S. Sonnei
SEQ ID NO: 44 amino acid seqeunce of glycerol kinase from Y. Pestis
SEQ ID NO: 45 amino acid seqeunce of glycerol kinase from P. Aeruginosa
SEQ ID NO: 46 amino acid seqeunce of glycerol kinase from B. Subtilis
SEQ ID NO: 47 DNA fragment coding 231-235 region of GlpK
SEQ ID NO: 48 231-235 region of mutant GlpK
SEQ ID NO: 49 231-235 region of mutant GlpK
SEQ ID NO: 50 231-235 region of mutant GlpK
SEQ ID NO: 51 231-235 region of mutant GlpK
SEQ ID NO: 52 231-235 region of mutant GlpK
SEQ ID NO: 53 231-235 region of mutant GlpK
SEQ ID NO: 54 231-235 region of mutant GlpK
SEQ ID NO: 55 231-235 region of mutant GlpK
SEQ ID NO: 56 231-235 region of mutant GlpK
SEQ ID NO: 47 231-235 region of mutant GlpK

INDUSTRIAL APPLICABILITY

According to the present invention, an L-amino acid-producing bacterium having enhanced ability to utilize glycerol, and a method for producing an L-amino acid by fermentation of glycerol using the bacterium are provided.

The invention claimed is:

1. A method for producing an L-amino acid comprising:
   a) culturing in a culture medium containing glycerol an L-amino acid producing bacterium of the Enterobacteriaceae family, and
   b) collecting the L-amino acid from the culture,
wherein said bacterium comprises glycerol kinase in which feedback inhibition by fructose-1,6-bisphosphate is desensitized, and said glycerol kinase comprises a mutation which results in the replacement of at least one amino acid with another amino acid in the region corresponding to the positions from 233 to 235 of the amino acid sequence of the wild type glycerol kinase shown in SEQ ID NO: 4.

2. The method according to claim 1, wherein said glycerol kinase further comprises a mutation which results in the replacement of at least one amino acid with another amino acid in the region corresponding to the positions from 231 to 232.

3. The method according to claim 1, wherein said glycerol kinase comprises a mutation selected from the group consisting of replacing the Gly residue at position 234 with an Asp residue, replacing Lys-Gly-Gly at the 233 to 235 positions with Arg-Ile-Pro, and replacing Gly-Gly-Lys-Gly-Gly at the 231 to 235 positions with Arg-Ala-His-Leu-Ala.

4. The method according to claim 1, wherein said bacterium is further modified so that activity of a glycerol facilitator and/or glycerol 3-phosphate dehydrogenase is enhanced.

5. The method according to claim 4, wherein the expression of at least one of said glycerol facilitator and said glycerol 3-phosphate dehydrogenase is increased by increasing the copy number of the gene or modifying an expression control sequence of the gene.

6. The method according to claim 1, wherein said bacterium is further modified so that activity of triose phosphate isomerase is enhanced.

7. The method according to claim 6, wherein the expression of said triose phosphate isomerase is increased by increasing the copy number of the gene or modifying an expression control sequence of the gene.

8. The method according to claim 1, wherein said L-amino acid is selected from the group consisting of an aromatic L-amino acid and a non-aromatic L-amino acid.

9. The method according to claim 8, wherein said aromatic L-amino acid is selected from the group consisting of L-phenylalanine, L-tyrosine, and L-tryptophan.

10. The method according to claim 8, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

11. The method according to claim 1, wherein said bacterium belongs to the genus *Escheriahia* or *Pantoea*.

12. The method according to claim 1, wherein the glycerol is obtained as from biodiesel production.

* * * * *

SEQUENCE LISTING

<160> NUMBER OF SEQ ID NOS: 57

<210> SEQ ID NO 1
<211> LENGTH: 846
<212> TYPE: DNA
<213> ORGANISM: Escherichia coli
<220> FEATURE:
<221> NAME/KEY: CDS
<222> LOCATION: (1)..(846)

<400> SEQUENCE: 1

| | | | | | | | | | | | | | | | | |
|---|---|---|---|---|---|---|---|---|---|---|---|---|---|---|---|---|
| atg | agt | caa | aca | tca | acc | ttg | aaa | ggc | cag | tgc | att | gct | gaa | ttc | ctc | 48 |
| Met | Ser | Gln | Thr | Ser | Thr | Leu | Lys | Gly | Gln | Cys | Ile | Ala | Glu | Phe | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | acc | ggg | ttg | ttg | att | ttc | ttc | ggt | gtg | ggt | tgc | gtt | gca | gca | cta | 96 |
| Gly | Thr | Gly | Leu | Leu | Ile | Phe | Phe | Gly | Val | Gly | Cys | Val | Ala | Ala | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| aaa | gtc | gct | ggt | gcg | tct | ttt | ggt | cag | tgg | gaa | atc | agt | gtc | att | tgg | 144 |
| Lys | Val | Ala | Gly | Ala | Ser | Phe | Gly | Gln | Trp | Glu | Ile | Ser | Val | Ile | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | ctg | ggg | gtg | gca | atg | gcc | atc | tac | ctg | acc | gca | ggg | gtt | tcc | ggc | 192 |
| Gly | Leu | Gly | Val | Ala | Met | Ala | Ile | Tyr | Leu | Thr | Ala | Gly | Val | Ser | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| gcg | cat | ctt | aat | ccc | gct | gtt | acc | att | gca | ttg | tgg | ctg | ttt | gcc | tgt | 240 |
| Ala | His | Leu | Asn | Pro | Ala | Val | Thr | Ile | Ala | Leu | Trp | Leu | Phe | Ala | Cys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | gac | aag | cgc | aaa | gtt | att | cct | ttt | atc | gtt | tca | caa | gtt | gcc | ggc | 288 |
| Phe | Asp | Lys | Arg | Lys | Val | Ile | Pro | Phe | Ile | Val | Ser | Gln | Val | Ala | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | ttc | tgt | gct | gcg | gct | tta | gtt | tac | ggg | ctt | tac | tac | aat | tta | ttt | 336 |
| Ala | Phe | Cys | Ala | Ala | Ala | Leu | Val | Tyr | Gly | Leu | Tyr | Tyr | Asn | Leu | Phe | |
| | | | | 100 | | | | | 105 | | | | | 110 | | |

| | | | | | | | | | | | | | | | | |
|---|---|---|---|---|---|---|---|---|---|---|---|---|---|---|---|---|
| ttc | gac | ttc | gag | cag | act | cat | cac | att | gtt | cgc | ggc | agc | gtt | gaa | agt | 384 |
| Phe | Asp | Phe | Glu | Gln | Thr | His | His | Ile | Val | Arg | Gly | Ser | Val | Glu | Ser | |
| | | | 115 | | | | | 120 | | | | | 125 | | | |

| | | | | | | | | | | | | | | | | |
|---|---|---|---|---|---|---|---|---|---|---|---|---|---|---|---|---|
| gtt | gat | ctg | gct | ggc | act | ttc | tct | act | tac | cct | aat | cct | cat | atc | aat | 432 |
| Val | Asp | Leu | Ala | Gly | Thr | Phe | Ser | Thr | Tyr | Pro | Asn | Pro | His | Ile | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| ttt | gtg | cag | gct | ttc | gca | gtt | gag | atg | gtg | att | acc | gct | att | ctg | atg | 480 |
| Phe | Val | Gln | Ala | Phe | Ala | Val | Glu | Met | Val | Ile | Thr | Ala | Ile | Leu | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggg | ctg | atc | ctg | gcg | tta | acg | gac | gat | ggc | aac | ggt | gta | cca | cgc | ggc | 528 |
| Gly | Leu | Ile | Leu | Ala | Leu | Thr | Asp | Asp | Gly | Asn | Gly | Val | Pro | Arg | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| cct | ttg | gct | ccc | ttg | ctg | att | ggt | cta | ctg | att | gcg | gtc | att | ggc | gca | 576 |
| Pro | Leu | Ala | Pro | Leu | Leu | Ile | Gly | Leu | Leu | Ile | Ala | Val | Ile | Gly | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| tct | atg | ggc | cca | ttg | aca | ggt | ttt | gcc | atg | aac | cca | gcg | cgt | gac | ttc | 624 |
| Ser | Met | Gly | Pro | Leu | Thr | Gly | Phe | Ala | Met | Asn | Pro | Ala | Arg | Asp | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| ggt | ccg | aaa | gtc | ttt | gcc | tgg | ctg | gcg | ggc | tgg | ggc | aat | gtc | gcc | ttt | 672 |
| Gly | Pro | Lys | Val | Phe | Ala | Trp | Leu | Ala | Gly | Trp | Gly | Asn | Val | Ala | Phe | |
| | 210 | | | | | 215 | | | | | 220 | | | | | |

| | | | | | | | | | | | | | | | | |
|---|---|---|---|---|---|---|---|---|---|---|---|---|---|---|---|---|
| acc | ggc | ggc | aga | gac | att | cct | tac | ttc | ctg | gtg | ccg | ctt | ttc | ggc | cct | 720 |
| Thr | Gly | Gly | Arg | Asp | Ile | Pro | Tyr | Phe | Leu | Val | Pro | Leu | Phe | Gly | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atc | gtt | ggc | gcg | att | gta | ggt | gca | ttt | gcc | tac | cgc | aaa | ctg | att | ggt | 768 |
| Ile | Val | Gly | Ala | Ile | Val | Gly | Ala | Phe | Ala | Tyr | Arg | Lys | Leu | Ile | Gly | |
| | | | | 245 | | | | | 250 | | | | | 255 | | |

```
cgc cat ttg cct tgc gat atc tgt gtt gtg gaa gaa aag gaa acc aca      816
Arg His Leu Pro Cys Asp Ile Cys Val Val Glu Glu Lys Glu Thr Thr
        260                 265                 270 act cct tca gaa caa aaa gct tcg ctg taa                              846
Thr Pro Ser Glu Gln Lys Ala Ser Leu
        275                 280

<210> SEQ ID NO 2
<211> LENGTH: 281
<212> TYPE: PRT
<213> ORGANISM: Escherichia coli

<400> SEQUENCE: 2

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280

<210> SEQ ID NO 3
<211> LENGTH: 1509
<212> TYPE: DNA
<213> ORGANISM: Escherichia coli
<220> FEATURE:
<221> NAME/KEY: CDS
<222> LOCATION: (1)..(1509)
```

<400> SEQUENCE: 3

```
atg act gaa aaa aaa tat atc gtt gcg ctc gac cag ggc acc acc agc      48
Met Thr Glu Lys Lys Tyr Ile Val Ala Leu Asp Gln Gly Thr Thr Ser
1               5                   10                  15 tcc cgc gcg gtc gta atg gat cac gat gcc aat atc att agc gtg tcg      96
Ser Arg Ala Val Val Met Asp His Asp Ala Asn Ile Ile Ser Val Ser
                20                  25                  30 cag cgc gaa ttt gag caa atc tac cca aaa cca ggt tgg gta gaa cac     144
Gln Arg Glu Phe Glu Gln Ile Tyr Pro Lys Pro Gly Trp Val Glu His
            35                  40                  45 gac cca atg gaa atc tgg gcc acc caa agc tcc acg ctg gta gaa gtg     192
Asp Pro Met Glu Ile Trp Ala Thr Gln Ser Ser Thr Leu Val Glu Val
        50                  55                  60 ctg gcg aaa gcc gat atc agt tcc gat caa att gca gct atc ggt att     240
Leu Ala Lys Ala Asp Ile Ser Ser Asp Gln Ile Ala Ala Ile Gly Ile
65                  70                  75                  80 acg aac cag cgt gaa acc act att gtc tgg gaa aaa gaa acc ggc aag     288
Thr Asn Gln Arg Glu Thr Thr Ile Val Trp Glu Lys Glu Thr Gly Lys
                85                  90                  95 cct atc tat aac gcc att gtc tgg cag tgc cgt cgt acc gca gaa atc     336
Pro Ile Tyr Asn Ala Ile Val Trp Gln Cys Arg Arg Thr Ala Glu Ile
            100                 105                 110 tgc gag cat tta aaa cgt gac ggt tta gaa gat tat atc cgc agc aat     384
Cys Glu His Leu Lys Arg Asp Gly Leu Glu Asp Tyr Ile Arg Ser Asn
        115                 120                 125 acc ggt ctg gtg att gac ccg tac ttt tct ggc acc aaa gtg aag tgg     432
Thr Gly Leu Val Ile Asp Pro Tyr Phe Ser Gly Thr Lys Val Lys Trp
130                 135                 140 atc ctc gac cat gtg gaa ggc tct cgc gag cgt gca cgt cgt ggt gaa     480
Ile Leu Asp His Val Glu Gly Ser Arg Glu Arg Ala Arg Arg Gly Glu
145                 150                 155                 160 ttg ctg ttt ggt acg gtt gat acg tgg ctt atc tgg aaa atg act cag     528
Leu Leu Phe Gly Thr Val Asp Thr Trp Leu Ile Trp Lys Met Thr Gln
                165                 170                 175 ggc cgt gtc cat gtg acc gat tac acc aac gcc tct cgt acc atg ttg     576
Gly Arg Val His Val Thr Asp Tyr Thr Asn Ala Ser Arg Thr Met Leu
            180                 185                 190 ttc aac atc cat acc ctg gac tgg gac gac aaa atg ctg gaa gtg ctg     624
Phe Asn Ile His Thr Leu Asp Trp Asp Asp Lys Met Leu Glu Val Leu
        195                 200                 205 gat att ccg cgc gag atg ctg cca gaa gtg cgt cgt tct tcc gaa gta     672
Asp Ile Pro Arg Glu Met Leu Pro Glu Val Arg Arg Ser Ser Glu Val
210                 215                 220 tac ggt cag act aac att ggc ggc aaa ggc ggc acg cgt att cca atc     720
Tyr Gly Gln Thr Asn Ile Gly Gly Lys Gly Gly Thr Arg Ile Pro Ile
225                 230                 235                 240 tcc ggg atc gcc ggt gac cag cag gcc gcg ctg ttt ggt cag ttg tgc     768
Ser Gly Ile Ala Gly Asp Gln Gln Ala Ala Leu Phe Gly Gln Leu Cys
                245                 250                 255 gtg aaa gaa ggg atg gcg aag aac acc tat ggc act ggc tgc ttt atg     816
Val Lys Glu Gly Met Ala Lys Asn Thr Tyr Gly Thr Gly Cys Phe Met
            260                 265                 270 ctg atg aac act ggc gag aaa gcg gtg aaa tca gaa aac ggc ctg ctg     864
Leu Met Asn Thr Gly Glu Lys Ala Val Lys Ser Glu Asn Gly Leu Leu
        275                 280                 285 acc acc atc gcc tgc ggc ccg act ggc gaa gtg aac tat gcg ttg gaa     912
Thr Thr Ile Ala Cys Gly Pro Thr Gly Glu Val Asn Tyr Ala Leu Glu
290                 295                 300
```

```
                                                                        -continued ggt gcg gtg ttt atg gca ggc gca tcc att cag tgg ctg cgc gat gaa         960
Gly Ala Val Phe Met Ala Gly Ala Ser Ile Gln Trp Leu Arg Asp Glu
305                 310                 315                 320 atg aag ttg att aac gac gcc tac gat tcc gaa tat ttc gcc acc aaa         1008
Met Lys Leu Ile Asn Asp Ala Tyr Asp Ser Glu Tyr Phe Ala Thr Lys
                325                 330                 335 gtg caa aac acc aat ggt gtg tat gtg gtt ccg gca ttt acc ggg ctg         1056
Val Gln Asn Thr Asn Gly Val Tyr Val Val Pro Ala Phe Thr Gly Leu
            340                 345                 350 ggt gcg ccg tac tgg gac ccg tat gcg cgc ggg gcg att ttc ggt ctg         1104
Gly Ala Pro Tyr Trp Asp Pro Tyr Ala Arg Gly Ala Ile Phe Gly Leu
        355                 360                 365 act cgt ggg gtg aac gct aac cac att ata cgc gcg acg ctg gag tct         1152
Thr Arg Gly Val Asn Ala Asn His Ile Ile Arg Ala Thr Leu Glu Ser
    370                 375                 380 att gct tat cag acg cgt gac gtg ctg gaa gcg atg cag gcc gac tct         1200
Ile Ala Tyr Gln Thr Arg Asp Val Leu Glu Ala Met Gln Ala Asp Ser
385                 390                 395                 400 ggt atc cgt ctg cac gcc ctg cgc gtg gat ggt ggc gca gta gca aac         1248
Gly Ile Arg Leu His Ala Leu Arg Val Asp Gly Gly Ala Val Ala Asn
                405                 410                 415 aat ttc ctg atg cag ttc cag tcc gat att ctc ggc acc cgc gtt gag         1296
Asn Phe Leu Met Gln Phe Gln Ser Asp Ile Leu Gly Thr Arg Val Glu
            420                 425                 430 cgc ccg gaa gtg cgc gaa gtc acc gca ttg ggt gcg gcc tat ctc gca         1344
Arg Pro Glu Val Arg Glu Val Thr Ala Leu Gly Ala Ala Tyr Leu Ala
        435                 440                 445 ggc ctg gcg gtt ggc ttc tgg cag aac ctc gac gag ctg caa gag aaa         1392
Gly Leu Ala Val Gly Phe Trp Gln Asn Leu Asp Glu Leu Gln Glu Lys
    450                 455                 460 gcg gtg att gag cgc gag ttc cgt cca ggc atc gaa acc act gag cgt         1440
Ala Val Ile Glu Arg Glu Phe Arg Pro Gly Ile Glu Thr Thr Glu Arg
465                 470                 475                 480 aat tac cgt tac gca ggc tgg aaa aaa gcg gtt aaa cgc gcg atg gcg         1488
Asn Tyr Arg Tyr Ala Gly Trp Lys Lys Ala Val Lys Arg Ala Met Ala
                485                 490                 495 tgg gaa gaa cac gac gaa taa                                             1509
Trp Glu Glu His Asp Glu
            500

<210> SEQ ID NO 4
<211> LENGTH: 502
<212> TYPE: PRT
<213> ORGANISM: Escherichia coli

<400> SEQUENCE: 4

Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Ile Ser Val Ser
                20                  25                  30

Gln Arg Glu Phe Glu Gln Ile Tyr Pro Lys Pro Gly Trp Val Glu His
            35                  40                  45

Asp Pro Met Glu Ile Trp Ala Thr Gln Ser Ser Thr Leu Val Glu Val
        50                  55                  60

Leu Ala Lys Ala Asp Ile Ser Ser Asp Gln Ile Ala Ala Ile Gly Ile
65                  70                  75                  80

Thr Asn Gln Arg Glu Thr Thr Ile Val Trp Glu Lys Glu Thr Gly Lys
                85                  90                  95
```

```
Pro Ile Tyr Asn Ala Ile Val Trp Gln Cys Arg Arg Thr Ala Glu Ile
            100                 105                 110
Cys Glu His Leu Lys Arg Asp Gly Leu Glu Asp Tyr Ile Arg Ser Asn
            115                 120                 125
Thr Gly Leu Val Ile Asp Pro Tyr Phe Ser Gly Thr Lys Val Lys Trp
            130                 135                 140
Ile Leu Asp His Val Glu Gly Ser Arg Glu Arg Ala Arg Arg Gly Glu
145                 150                 155                 160
Leu Leu Phe Gly Thr Val Asp Thr Trp Leu Ile Trp Lys Met Thr Gln
                165                 170                 175
Gly Arg Val His Val Thr Asp Tyr Thr Asn Ala Ser Arg Thr Met Leu
            180                 185                 190
Phe Asn Ile His Thr Leu Asp Trp Asp Asp Lys Met Leu Glu Val Leu
            195                 200                 205
Asp Ile Pro Arg Glu Met Leu Pro Glu Val Arg Arg Ser Ser Glu Val
        210                 215                 220
Tyr Gly Gln Thr Asn Ile Gly Gly Lys Gly Gly Thr Arg Ile Pro Ile
225                 230                 235                 240
Ser Gly Ile Ala Gly Asp Gln Gln Ala Ala Leu Phe Gly Gln Leu Cys
                245                 250                 255
Val Lys Glu Gly Met Ala Lys Asn Thr Tyr Gly Thr Gly Cys Phe Met
            260                 265                 270
Leu Met Asn Thr Gly Glu Lys Ala Val Lys Ser Glu Asn Gly Leu Leu
            275                 280                 285
Thr Thr Ile Ala Cys Gly Pro Thr Gly Glu Val Asn Tyr Ala Leu Glu
        290                 295                 300
Gly Ala Val Phe Met Ala Gly Ala Ser Ile Gln Trp Leu Arg Asp Glu
305                 310                 315                 320
Met Lys Leu Ile Asn Asp Ala Tyr Asp Ser Glu Tyr Phe Ala Thr Lys
                325                 330                 335
Val Gln Asn Thr Asn Gly Val Tyr Val Val Pro Ala Phe Thr Gly Leu
            340                 345                 350
Gly Ala Pro Tyr Trp Asp Pro Tyr Ala Arg Gly Ala Ile Phe Gly Leu
            355                 360                 365
Thr Arg Gly Val Asn Ala Asn His Ile Ile Arg Ala Thr Leu Glu Ser
        370                 375                 380
Ile Ala Tyr Gln Thr Arg Asp Val Leu Glu Ala Met Gln Ala Asp Ser
385                 390                 395                 400
Gly Ile Arg Leu His Ala Leu Arg Val Asp Gly Gly Ala Val Ala Asn
                405                 410                 415
Asn Phe Leu Met Gln Phe Gln Ser Asp Ile Leu Gly Thr Arg Val Glu
            420                 425                 430
Arg Pro Glu Val Arg Glu Val Thr Ala Leu Gly Ala Ala Tyr Leu Ala
            435                 440                 445
Gly Leu Ala Val Gly Phe Trp Gln Asn Leu Asp Glu Leu Gln Glu Lys
        450                 455                 460
Ala Val Ile Glu Arg Glu Phe Arg Pro Gly Ile Glu Thr Thr Glu Arg
465                 470                 475                 480
Asn Tyr Arg Tyr Ala Gly Trp Lys Lys Ala Val Lys Arg Ala Met Ala
                485                 490                 495
Trp Glu Glu His Asp Glu
            500
```

```
<210> SEQ ID NO 5
<211> LENGTH: 1629
<212> TYPE: DNA
<213> ORGANISM: Escherichia coli
<220> FEATURE:
<221> NAME/KEY: CDS
<222> LOCATION: (1)..(1629)

<400> SEQUENCE: 5 atg aaa act cgc gac tcg caa tca agt gac gtg att atc att ggc ggc        48
Met Lys Thr Arg Asp Ser Gln Ser Ser Asp Val Ile Ile Ile Gly Gly
1               5                   10                  15 ggc gca acg gga gcc ggg att gcc cgc gac tgt gcc ctg cgc ggg ctg        96
Gly Ala Thr Gly Ala Gly Ile Ala Arg Asp Cys Ala Leu Arg Gly Leu
            20                  25                  30 cgc gtg att ttg gtt gag cgc cac gac atc gca acc ggt gcc acc ggg       144
Arg Val Ile Leu Val Glu Arg His Asp Ile Ala Thr Gly Ala Thr Gly
        35                  40                  45 cgt aac cac ggc ctg ctg cac agc ggt gcg cgc tat gcg gta acc gat       192
Arg Asn His Gly Leu Leu His Ser Gly Ala Arg Tyr Ala Val Thr Asp
    50                  55                  60 gcg gaa tcg gcc cgc gaa tgc att agt gaa aac cag atc ctg aaa cgc       240
Ala Glu Ser Ala Arg Glu Cys Ile Ser Glu Asn Gln Ile Leu Lys Arg
65                  70                  75                  80 att gca cgt cac tgc gtt gaa cca acc aac ggc ctg ttt atc acc ctg       288
Ile Ala Arg His Cys Val Glu Pro Thr Asn Gly Leu Phe Ile Thr Leu
                85                  90                  95 ccg gaa gat gac ctc tcc ttc cag gcc act ttt att cgc gcc tgc gaa       336
Pro Glu Asp Asp Leu Ser Phe Gln Ala Thr Phe Ile Arg Ala Cys Glu
            100                 105                 110 gaa gca ggg atc agc gca gaa gct ata gac ccg cag caa gcg cgc att       384
Glu Ala Gly Ile Ser Ala Glu Ala Ile Asp Pro Gln Gln Ala Arg Ile
        115                 120                 125 atc gaa cct gcc gtt aac ccg gca ctg att ggc gcg gtg aaa gtt ccg       432
Ile Glu Pro Ala Val Asn Pro Ala Leu Ile Gly Ala Val Lys Val Pro
    130                 135                 140 gat ggc acc gtt gat cca ttt cgt ctg acc gca gca aac atg ctg gat       480
Asp Gly Thr Val Asp Pro Phe Arg Leu Thr Ala Ala Asn Met Leu Asp
145                 150                 155                 160 gcc aaa gaa cac ggt gcc gtt atc ctt acc gct cat gaa gtc acg ggg       528
Ala Lys Glu His Gly Ala Val Ile Leu Thr Ala His Glu Val Thr Gly
                165                 170                 175 ctg att cgt gaa ggc gcg acg gtg tgc ggt gtt cgt gta cgt aac cat       576
Leu Ile Arg Glu Gly Ala Thr Val Cys Gly Val Arg Val Arg Asn His
            180                 185                 190 ctc acc ggc gaa act cag gcc ctt cat gca cct gtc gtg gtt aat gcc       624
Leu Thr Gly Glu Thr Gln Ala Leu His Ala Pro Val Val Val Asn Ala
        195                 200                 205 gct ggg atc tgg ggg caa cac att gcc gaa tat gcc gat ctg cgc att       672
Ala Gly Ile Trp Gly Gln His Ile Ala Glu Tyr Ala Asp Leu Arg Ile
    210                 215                 220 cgc atg ttc ccg gcg aaa gga tcg ctg ctg atc atg gat cac cgc att       720
Arg Met Phe Pro Ala Lys Gly Ser Leu Leu Ile Met Asp His Arg Ile
225                 230                 235                 240 aac cag cat gtg atc aac cgc tgc cgt aaa cct tcc gac gcc gat att       768
Asn Gln His Val Ile Asn Arg Cys Arg Lys Pro Ser Asp Ala Asp Ile
                245                 250                 255 ctg gtg cct ggc gat acc att tcg ctg att ggt acc acc tct tta cgt       816
Leu Val Pro Gly Asp Thr Ile Ser Leu Ile Gly Thr Thr Ser Leu Arg
            260                 265                 270
```

```
att tac aac gag att gac gat aat cga gtg acg gca gaa gag gtt        864
Ile Asp Tyr Asn Glu Ile Asp Asp Asn Arg Val Thr Ala Glu Glu Val
            275                 280                 285 gat att ctg ctg cgt gaa ggg gaa aaa ctg gcc ccc gtg atg gcg aaa    912
Asp Ile Leu Leu Arg Glu Gly Glu Lys Leu Ala Pro Val Met Ala Lys
        290                 295                 300 acg cgc att ttg cgg gcc tat tct ggc gtg cgc ccg ctg gtt gcc agc    960
Thr Arg Ile Leu Arg Ala Tyr Ser Gly Val Arg Pro Leu Val Ala Ser
305                 310                 315                 320 gat gac gac ccg agc gga cgt aac gtc agc cgt ggc atc gtg ctg ctc   1008
Asp Asp Asp Pro Ser Gly Arg Asn Val Ser Arg Gly Ile Val Leu Leu
                325                 330                 335 gac cat gct gaa cgc gat ggt ctg gac gga ttt atc acc atc acc ggt   1056
Asp His Ala Glu Arg Asp Gly Leu Asp Gly Phe Ile Thr Ile Thr Gly
            340                 345                 350 ggc aaa ctg atg acc tat cgg ctg atg gct gaa tgg gct acc gac gcg   1104
Gly Lys Leu Met Thr Tyr Arg Leu Met Ala Glu Trp Ala Thr Asp Ala
        355                 360                 365 gta tgc cgc aaa ctg ggc aac acg cgc ccc tgt acg act gcc gat ctg   1152
Val Cys Arg Lys Leu Gly Asn Thr Arg Pro Cys Thr Thr Ala Asp Leu
370                 375                 380 gca ctg cct ggt tca caa gaa ccc gct gaa gtt acc ttg cgt aaa gtc   1200
Ala Leu Pro Gly Ser Gln Glu Pro Ala Glu Val Thr Leu Arg Lys Val
385                 390                 395                 400 atc tcc ctg cct gcc ccg ctg cgc ggt tct gcg gtt tat cgt cat ggc   1248
Ile Ser Leu Pro Ala Pro Leu Arg Gly Ser Ala Val Tyr Arg His Gly
                405                 410                 415 gat cgc acg cct gcc tgg ctg agc gaa ggc cgt ctg cac cgt agc ctg   1296
Asp Arg Thr Pro Ala Trp Leu Ser Glu Gly Arg Leu His Arg Ser Leu
            420                 425                 430 gta tgt gag tgc gaa gcg gta act gcg ggt gaa gtg cag tac gcg gta   1344
Val Cys Glu Cys Glu Ala Val Thr Ala Gly Glu Val Gln Tyr Ala Val
        435                 440                 445 gaa aat tta aac gtt aat agc ctg ctg gat tta cgc cgt cgt acc cgt   1392
Glu Asn Leu Asn Val Asn Ser Leu Leu Asp Leu Arg Arg Arg Thr Arg
450                 455                 460 gtg ggg atg ggc acc tgc cag ggc gaa ctc tgc gcc tgc cgc gct gcc   1440
Val Gly Met Gly Thr Cys Gln Gly Glu Leu Cys Ala Cys Arg Ala Ala
465                 470                 475                 480 gga ctg ctg caa cgt ttt aac gtc acg acg tcc gcg caa tct atc gag   1488
Gly Leu Leu Gln Arg Phe Asn Val Thr Thr Ser Ala Gln Ser Ile Glu
                485                 490                 495 caa ctt tcc acc ttc ctt aac gaa cgc tgg aaa ggc gtg caa ccc atc   1536
Gln Leu Ser Thr Phe Leu Asn Glu Arg Trp Lys Gly Val Gln Pro Ile
            500                 505                 510 gcc tgg gga gat gca ctg cgc gaa agc gaa ttt acc cgc tgg gtt tat   1584
Ala Trp Gly Asp Ala Leu Arg Glu Ser Glu Phe Thr Arg Trp Val Tyr
        515                 520                 525 cag gga ttg tgt ggt ctg gag aag gag cag aaa gat gcg ctt tga      1629
Gln Gly Leu Cys Gly Leu Glu Lys Glu Gln Lys Asp Ala Leu
530                 535                 540

<210> SEQ ID NO 6
<211> LENGTH: 542
<212> TYPE: PRT
<213> ORGANISM: Escherichia coli
```

<400> SEQUENCE: 6

```
Met Lys Thr Arg Asp Ser Gln Ser Asp Val Ile Ile Ile Gly Gly
 1               5                  10                  15

Gly Ala Thr Gly Ala Gly Ile Ala Arg Asp Cys Ala Leu Arg Gly Leu
                20                  25                  30

Arg Val Ile Leu Val Glu Arg His Asp Ile Ala Thr Gly Ala Thr Gly
            35                  40                  45

Arg Asn His Gly Leu Leu His Ser Gly Ala Arg Tyr Ala Val Thr Asp
        50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
                100                 105                 110

Glu Ala Gly Ile Ser Ala Glu Ala Ile Asp Pro Gln Gln Ala Arg Ile
                115                 120                 125

Ile Glu Pro Ala Val Asn Pro Ala Leu Ile Gly Ala Val Lys Val Pro
        130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Asn Ala
        195                 200                 205

Ala Gly Ile Trp Gly Gln His Ile Ala Glu Tyr Ala Asp Leu Arg Ile
        210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asp Asn Arg Val Thr Ala Glu Glu Val
        275                 280                 285

Asp Ile Leu Leu Arg Glu Gly Glu Lys Leu Ala Pro Val Met Ala Lys
    290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Val Ser Arg Gly Ile Val Leu Leu
                325                 330                 335

Asp His Ala Glu Arg Asp Gly Leu Asp Gly Phe Ile Thr Ile Thr Gly
                340                 345                 350

Gly Lys Leu Met Thr Tyr Arg Leu Met Ala Glu Trp Ala Thr Asp Ala
            355                 360                 365

Val Cys Arg Lys Leu Gly Asn Thr Arg Pro Cys Thr Thr Ala Asp Leu
        370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415
```

```
Asp Arg Thr Pro Ala Trp Leu Ser Glu Gly Arg Leu His Arg Ser Leu
            420                 425                 430

Val Cys Glu Cys Glu Ala Val Thr Ala Gly Glu Val Gln Tyr Ala Val
            435                 440                 445

Glu Asn Leu Asn Val Asn Ser Leu Leu Asp Leu Arg Arg Arg Thr Arg
            450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
            485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
            515                 520                 525

Gln Gly Leu Cys Gly Leu Glu Lys Glu Gln Lys Asp Ala Leu
            530                 535                 540

<210> SEQ ID NO 7
<211> LENGTH: 1260
<212> TYPE: DNA
<213> ORGANISM: Escherichia coli
<220> FEATURE:
<221> NAME/KEY: CDS
<222> LOCATION: (1)..(1260)

<400> SEQUENCE: 7 atg cgc ttt gat act gtc att atg ggc ggc ggc ctc gcc gga tta ctc      48
Met Arg Phe Asp Thr Val Ile Met Gly Gly Gly Leu Ala Gly Leu Leu
1               5                   10                  15 tgt ggc ctg caa ctg caa aaa cac ggc ctg cgc tgt gcc att gtc act      96
Cys Gly Leu Gln Leu Gln Lys His Gly Leu Arg Cys Ala Ile Val Thr
                20                  25                  30 cgt ggt caa agc gca ctg cat ttc tca tcc gga tcg ctg gat ttg ctg     144
Arg Gly Gln Ser Ala Leu His Phe Ser Ser Gly Ser Leu Asp Leu Leu
            35                  40                  45 agc cat ctg cca gat ggt caa ccg gtg aca gac att cac agt gga ctg     192
Ser His Leu Pro Asp Gly Gln Pro Val Thr Asp Ile His Ser Gly Leu
        50                  55                  60 gaa tct ttg cgt cag cag gca cca gcc cat cct tac tcc ctt ctc gag     240
Glu Ser Leu Arg Gln Gln Ala Pro Ala His Pro Tyr Ser Leu Leu Glu
65                  70                  75                  80 cca caa cgc gtg ctc gat ctc gct tgc cag gcg cag gca tta atc gct     288
Pro Gln Arg Val Leu Asp Leu Ala Cys Gln Ala Gln Ala Leu Ile Ala
                85                  90                  95 gaa agc ggt gcg caa ttg cag ggc agc gta gaa ctt gct cac cag cgg     336
Glu Ser Gly Ala Gln Leu Gln Gly Ser Val Glu Leu Ala His Gln Arg
            100                 105                 110 gtt acg ccg ctc ggc act ctg cgc tct acc tgg cta agt tcg cca gaa     384
Val Thr Pro Leu Gly Thr Leu Arg Ser Thr Trp Leu Ser Ser Pro Glu
        115                 120                 125 gtc ccc gtc tgg ccg ctg ccc gcg aag aaa ata tgt gta gtg gga att     432
Val Pro Val Trp Pro Leu Pro Ala Lys Lys Ile Cys Val Val Gly Ile
    130                 135                 140 agc ggc ctg atg gat ttt cag gcg cac ctt gcg gca gct tcg ttg cgt     480
Ser Gly Leu Met Asp Phe Gln Ala His Leu Ala Ala Ala Ser Leu Arg
145                 150                 155                 160 gaa ctc ggc ctt gcc gtt gaa acc gca gaa ata gag ctg ccg gaa ctg     528
Glu Leu Gly Leu Ala Val Glu Thr Ala Glu Ile Glu Leu Pro Glu Leu
                165                 170                 175
```

```
gat gtg ctg cgc aat aac gcc acc gaa ttt cgc gcg gtg aat atc gcc      576
Asp Val Leu Arg Asn Asn Ala Thr Glu Phe Arg Ala Val Asn Ile Ala
        180                 185                 190 cgt ttc ctt gat aat gaa gaa aac tgg ccg ctg tta ctt gat gcg ctt      624
Arg Phe Leu Asp Asn Glu Glu Asn Trp Pro Leu Leu Leu Asp Ala Leu
        195                 200                 205 att cct gtc gcc aat acc tgc gaa atg atc ctg atg ccc gcc tgc ttc      672
Ile Pro Val Ala Asn Thr Cys Glu Met Ile Leu Met Pro Ala Cys Phe
    210                 215                 220 ggt ctg gcc gat gac aaa ctg tgg cgt tgg ttg aat gaa aaa cta cct      720
Gly Leu Ala Asp Asp Lys Leu Trp Arg Trp Leu Asn Glu Lys Leu Pro
225                 230                 235                 240 tgt tca ctg atg ctt ttg cca acg ctg ccg cct tcc gtg ctg ggc att      768
Cys Ser Leu Met Leu Leu Pro Thr Leu Pro Pro Ser Val Leu Gly Ile
                245                 250                 255 cgt ctg caa aac cag tta cag cgc cag ttt gtg cgc cag ggt ggc gtg      816
Arg Leu Gln Asn Gln Leu Gln Arg Gln Phe Val Arg Gln Gly Gly Val
            260                 265                 270 tgg atg ccg ggc gat gaa gtg aaa aaa gtg acc tgt aaa aat ggc gta      864
Trp Met Pro Gly Asp Glu Val Lys Lys Val Thr Cys Lys Asn Gly Val
        275                 280                 285 gtg aac gaa atc tgg acc cgc aat cac gcc gat att ccg cta cgt cca      912
Val Asn Glu Ile Trp Thr Arg Asn His Ala Asp Ile Pro Leu Arg Pro
    290                 295                 300 cgt ttc gcg gtt ctc gcc agc ggc agt ttc ttt agt ggc gga ctg gta      960
Arg Phe Ala Val Leu Ala Ser Gly Ser Phe Phe Ser Gly Gly Leu Val
305                 310                 315                 320 gcg gaa cgt aac ggc att cga gag ccg att ctc ggc ctt gat gtg cta     1008
Ala Glu Arg Asn Gly Ile Arg Glu Pro Ile Leu Gly Leu Asp Val Leu
                325                 330                 335 caa acc gcc acg cgg ggt gaa tgg tat aag gga gat ttt ttt gcg ccg     1056
Gln Thr Ala Thr Arg Gly Glu Trp Tyr Lys Gly Asp Phe Phe Ala Pro
            340                 345                 350 caa ccg tgg cag cag ttc ggt gta acc act gat gag acg cta cgc ccg     1104
Gln Pro Trp Gln Gln Phe Gly Val Thr Thr Asp Glu Thr Leu Arg Pro
        355                 360                 365 tca cag gca ggg caa acc att gaa aac ctg ttt gcc atc ggt tcg gtg     1152
Ser Gln Ala Gly Gln Thr Ile Glu Asn Leu Phe Ala Ile Gly Ser Val
    370                 375                 380 ctg ggc gga ttt gat ccc atc gcc cag gga tgc ggc ggc gtt tgt         1200
Leu Gly Gly Phe Asp Pro Ile Ala Gln Gly Cys Gly Gly Val Cys
385                 390                 395                 400 gcc gtc agt gct tta cat gcc gct caa cag att gcc caa cgc gca gga     1248
Ala Val Ser Ala Leu His Ala Ala Gln Gln Ile Ala Gln Arg Ala Gly
                405                 410                 415 ggc caa caa tga                                                     1260
Gly Gln Gln <210> SEQ ID NO 8
<211> LENGTH: 419
<212> TYPE: PRT
<213> ORGANISM: Escherichia coli

<400> SEQUENCE: 8

Met Arg Phe Asp Thr Val Ile Met Gly Gly Gly Leu Ala Gly Leu Leu
1               5                   10                  15

Cys Gly Leu Gln Leu Gln Lys His Gly Leu Arg Cys Ala Ile Val Thr
            20                  25                  30

Arg Gly Gln Ser Ala Leu His Phe Ser Ser Gly Ser Leu Asp Leu Leu
        35                  40                  45
```

Ser His Leu Pro Asp Gly Gln Pro Val Thr Asp Ile His Ser Gly Leu
 50                  55                  60

Glu Ser Leu Arg Gln Gln Ala Pro Ala His Pro Tyr Ser Leu Leu Glu
 65                  70                  75                  80

Pro Gln Arg Val Leu Asp Leu Ala Cys Gln Ala Gln Ala Leu Ile Ala
                 85                  90                  95

Glu Ser Gly Ala Gln Leu Gln Gly Ser Val Glu Leu Ala His Gln Arg
                100                 105                 110

Val Thr Pro Leu Gly Thr Leu Arg Ser Thr Trp Leu Ser Ser Pro Glu
                115                 120                 125

Val Pro Val Trp Pro Leu Pro Ala Lys Lys Ile Cys Val Val Gly Ile
130                 135                 140

Ser Gly Leu Met Asp Phe Gln Ala His Leu Ala Ala Ser Leu Arg
145                 150                 155                 160

Glu Leu Gly Leu Ala Val Glu Thr Ala Glu Ile Glu Leu Pro Glu Leu
                165                 170                 175

Asp Val Leu Arg Asn Asn Ala Thr Glu Phe Arg Ala Val Asn Ile Ala
                180                 185                 190

Arg Phe Leu Asp Asn Glu Glu Asn Trp Pro Leu Leu Leu Asp Ala Leu
                195                 200                 205

Ile Pro Val Ala Asn Thr Cys Glu Met Ile Leu Met Pro Ala Cys Phe
210                 215                 220

Gly Leu Ala Asp Asp Lys Leu Trp Arg Trp Leu Asn Glu Lys Leu Pro
225                 230                 235                 240

Cys Ser Leu Met Leu Leu Pro Thr Leu Pro Pro Ser Val Leu Gly Ile
                245                 250                 255

Arg Leu Gln Asn Gln Leu Gln Arg Gln Phe Val Arg Gln Gly Gly Val
                260                 265                 270

Trp Met Pro Gly Asp Glu Val Lys Lys Val Thr Cys Lys Asn Gly Val
                275                 280                 285

Val Asn Glu Ile Trp Thr Arg Asn His Ala Asp Ile Pro Leu Arg Pro
290                 295                 300

Arg Phe Ala Val Leu Ala Ser Gly Ser Phe Phe Ser Gly Gly Leu Val
305                 310                 315                 320

Ala Glu Arg Asn Gly Ile Arg Glu Pro Ile Leu Gly Leu Asp Val Leu
                325                 330                 335

Gln Thr Ala Thr Arg Gly Glu Trp Tyr Lys Gly Asp Phe Phe Ala Pro
                340                 345                 350

Gln Pro Trp Gln Gln Phe Gly Val Thr Thr Asp Glu Thr Leu Arg Pro
                355                 360                 365

Ser Gln Ala Gly Gln Thr Ile Glu Asn Leu Phe Ala Ile Gly Ser Val
                370                 375                 380

Leu Gly Gly Phe Asp Pro Ile Ala Gln Gly Cys Gly Gly Gly Val Cys
385                 390                 395                 400

Ala Val Ser Ala Leu His Ala Ala Gln Gln Ile Ala Gln Arg Ala Gly
                405                 410                 415

Gly Gln Gln

<210> SEQ ID NO 9
<211> LENGTH: 1191
<212> TYPE: DNA
<213> ORGANISM: Escherichia coli
<220> FEATURE:
<221> NAME/KEY: CDS
<222> LOCATION: (1)..(1191)

<400> SEQUENCE: 9

```
atg aat gac acc agc ttc gaa aac tgc att aag tgc acc gtc tgc acc      48
Met Asn Asp Thr Ser Phe Glu Asn Cys Ile Lys Cys Thr Val Cys Thr
1               5                   10                  15 acc gcc tgc ccg gtg agc cgg gtg aat ccc ggt tat cca ggg cca aaa      96
Thr Ala Cys Pro Val Ser Arg Val Asn Pro Gly Tyr Pro Gly Pro Lys
            20                  25                  30 caa gcc ggg ccg gat ggc gag cgt ctg cgt ttg aaa gat ggc gca ctg     144
Gln Ala Gly Pro Asp Gly Glu Arg Leu Arg Leu Lys Asp Gly Ala Leu
        35                  40                  45 tat gac gag gcg ctg aaa tat tgc atc aac tgc aaa cgt tgt gaa gtc     192
Tyr Asp Glu Ala Leu Lys Tyr Cys Ile Asn Cys Lys Arg Cys Glu Val
50                  55                  60 gcc tgc ccg tcc gat gtg aag att ggc gat att atc cag cgc gcg cgg     240
Ala Cys Pro Ser Asp Val Lys Ile Gly Asp Ile Ile Gln Arg Ala Arg
65                  70                  75                  80 gcg aaa tat gac acc acg cgc ccg tcg ctg cgt aat ttt gtg ttg agt     288
Ala Lys Tyr Asp Thr Thr Arg Pro Ser Leu Arg Asn Phe Val Leu Ser
                85                  90                  95 cat acc gac ctg atg ggt agc gtt tcc acg ccg ttc gca cca atc gtc     336
His Thr Asp Leu Met Gly Ser Val Ser Thr Pro Phe Ala Pro Ile Val
            100                 105                 110 aac acc gct acc tcg ctg aaa ccg gtg cgg cag ctg ctt gat gcg gcg     384
Asn Thr Ala Thr Ser Leu Lys Pro Val Arg Gln Leu Leu Asp Ala Ala
        115                 120                 125 tta aaa atc gat cat cgc cgc acg cta ccg aaa tac tcc ttc ggc acg     432
Leu Lys Ile Asp His Arg Arg Thr Leu Pro Lys Tyr Ser Phe Gly Thr
    130                 135                 140 ttc cgt cgc tgg tat cgc agc gtg gcg gct cag caa gca caa tat aaa     480
Phe Arg Arg Trp Tyr Arg Ser Val Ala Ala Gln Gln Ala Gln Tyr Lys
145                 150                 155                 160 gac cag gtc gct ttc ttt cac ggc tgc ttc gtt aac tac aac cat ccg     528
Asp Gln Val Ala Phe Phe His Gly Cys Phe Val Asn Tyr Asn His Pro
                165                 170                 175 cag tta ggt aaa gat tta att aaa gtg ctc aac gca atg ggt acc ggt     576
Gln Leu Gly Lys Asp Leu Ile Lys Val Leu Asn Ala Met Gly Thr Gly
            180                 185                 190 gta caa ctg ctc agc aaa gaa aaa tgc tgc ggc gta ccg cta atc gcc     624
Val Gln Leu Leu Ser Lys Glu Lys Cys Cys Gly Val Pro Leu Ile Ala
        195                 200                 205 aac ggc ttt acc gat aaa gca cgc aaa cag gca att acg aat gta gag     672
Asn Gly Phe Thr Asp Lys Ala Arg Lys Gln Ala Ile Thr Asn Val Glu
    210                 215                 220 tcg atc cgc gaa gct gtg gga gta aaa ggc att ccg gtg att gcc acc     720
Ser Ile Arg Glu Ala Val Gly Val Lys Gly Ile Pro Val Ile Ala Thr
225                 230                 235                 240 tcc tca acc tgt aca ttt gcc ctg cgc gac gaa tac ccg gaa gtg ctg     768
Ser Ser Thr Cys Thr Phe Ala Leu Arg Asp Glu Tyr Pro Glu Val Leu
                245                 250                 255 aat gtc gac aac aaa ggc ttg cgc gat cat atc gaa ctg gca acc cgc     816
Asn Val Asp Asn Lys Gly Leu Arg Asp His Ile Glu Leu Ala Thr Arg
            260                 265                 270 tgg ctg tgg cgc aag ctg gac gaa ggc aaa acg tta ccg ctg aaa ccg     864
Trp Leu Trp Arg Lys Leu Asp Glu Gly Lys Thr Leu Pro Leu Lys Pro
        275                 280                 285 ctg ccg ctg aaa gtg gtt tat cac act ccg tgc cat atg gaa aaa atg     912
Leu Pro Leu Lys Val Val Tyr His Thr Pro Cys His Met Glu Lys Met
    290                 295                 300
```

-continued

```
ggc tgg acg ctc tac acc ctg gag ctg ttg cgt aac atc ccg ggg ctt     960
Gly Trp Thr Leu Tyr Thr Leu Glu Leu Leu Arg Asn Ile Pro Gly Leu
305                 310                 315                 320 gag tta acg gtg ctg gat tcc cag tgc tgc ggt att gcg ggt act tac    1008
Glu Leu Thr Val Leu Asp Ser Gln Cys Cys Gly Ile Ala Gly Thr Tyr
                325                 330                 335 ggt ttc aaa aaa gag aac tac ccc acc tca caa gcc atc ggc gca cca    1056
Gly Phe Lys Lys Glu Asn Tyr Pro Thr Ser Gln Ala Ile Gly Ala Pro
            340                 345                 350 ctg ttc cgc cag ata gaa gaa agc ggc gca gat ctg gtg gtc acc gac    1104
Leu Phe Arg Gln Ile Glu Glu Ser Gly Ala Asp Leu Val Val Thr Asp
        355                 360                 365 tgc gaa acc tgt aaa tgg cag att gag atg tcc aca agt ctt cgc tgc    1152
Cys Glu Thr Cys Lys Trp Gln Ile Glu Met Ser Thr Ser Leu Arg Cys
    370                 375                 380 gaa cat ccg att acg cta ctg gcc cag gcg ctg gct taa                1191
Glu His Pro Ile Thr Leu Leu Ala Gln Ala Leu Ala
385                 390                 395
```

<210> SEQ ID NO 10
<211> LENGTH: 396
<212> TYPE: PRT
<213> ORGANISM: Escherichia coli

<400> SEQUENCE: 10

```
Met Asn Asp Thr Ser Phe Glu Asn Cys Ile Lys Cys Thr Val Cys Thr
1               5                   10                  15

Thr Ala Cys Pro Val Ser Arg Val Asn Pro Gly Tyr Pro Gly Pro Lys
            20                  25                  30

Gln Ala Gly Pro Asp Gly Glu Arg Leu Arg Leu Lys Asp Gly Ala Leu
        35                  40                  45

Tyr Asp Glu Ala Leu Lys Tyr Cys Ile Asn Cys Lys Arg Cys Glu Val
    50                  55                  60

Ala Cys Pro Ser Asp Val Lys Ile Gly Asp Ile Ile Gln Arg Ala Arg
65                  70                  75                  80

Ala Lys Tyr Asp Thr Thr Arg Pro Ser Leu Arg Asn Phe Val Leu Ser
                85                  90                  95

His Thr Asp Leu Met Gly Ser Val Ser Thr Pro Phe Ala Pro Ile Val
            100                 105                 110

Asn Thr Ala Thr Ser Leu Lys Pro Val Arg Gln Leu Leu Asp Ala Ala
        115                 120                 125

Leu Lys Ile Asp His Arg Arg Thr Leu Pro Lys Tyr Ser Phe Gly Thr
    130                 135                 140

Phe Arg Arg Trp Tyr Arg Ser Val Ala Ala Gln Gln Ala Gln Tyr Lys
145                 150                 155                 160

Asp Gln Val Ala Phe Phe His Gly Cys Phe Val Asn Tyr Asn His Pro
                165                 170                 175

Gln Leu Gly Lys Asp Leu Ile Lys Val Leu Asn Ala Met Gly Thr Gly
            180                 185                 190

Val Gln Leu Leu Ser Lys Glu Lys Cys Cys Gly Val Pro Leu Ile Ala
        195                 200                 205

Asn Gly Phe Thr Asp Lys Ala Arg Lys Gln Ala Ile Thr Asn Val Glu
    210                 215                 220

Ser Ile Arg Glu Ala Val Gly Val Lys Gly Ile Pro Val Ile Ala Thr
225                 230                 235                 240

Ser Ser Thr Cys Thr Phe Ala Leu Arg Asp Glu Tyr Pro Glu Val Leu
                245                 250                 255
```

```
Asn Val Asp Asn Lys Gly Leu Arg Asp His Ile Glu Leu Ala Thr Arg
            260                 265                 270

Trp Leu Trp Arg Lys Leu Asp Glu Gly Lys Thr Leu Pro Leu Lys Pro
        275                 280                 285

Leu Pro Leu Lys Val Val Tyr His Thr Pro Cys His Met Glu Lys Met
        290                 295                 300

Gly Trp Thr Leu Tyr Thr Leu Glu Leu Leu Arg Asn Ile Pro Gly Leu
305                 310                 315                 320

Glu Leu Thr Val Leu Asp Ser Gln Cys Cys Gly Ile Ala Gly Thr Tyr
                325                 330                 335

Gly Phe Lys Lys Glu Asn Tyr Pro Thr Ser Gln Ala Ile Gly Ala Pro
                340                 345                 350

Leu Phe Arg Gln Ile Glu Glu Ser Gly Ala Asp Leu Val Val Thr Asp
                355                 360                 365

Cys Glu Thr Cys Lys Trp Gln Ile Glu Met Ser Thr Ser Leu Arg Cys
        370                 375                 380

Glu His Pro Ile Thr Leu Leu Ala Gln Ala Leu Ala
385                 390                 395
```

```
<210> SEQ ID NO 11
<211> LENGTH: 1506
<212> TYPE: DNA
<213> ORGANISM: Escherichia coli
<220> FEATURE:
<221> NAME/KEY: CDS
<222> LOCATION: (1)..(1506)

<400> SEQUENCE: 11
```

```
atg gaa acc aaa gat ctg att gtg ata ggg ggc ggc atc aat ggt gct    48
Met Glu Thr Lys Asp Leu Ile Val Ile Gly Gly Gly Ile Asn Gly Ala
1               5                   10                  15 ggt atc gcg gca gac gcc gct gga cgc ggt tta tcc gtg ctg atg ctg    96
Gly Ile Ala Ala Asp Ala Ala Gly Arg Gly Leu Ser Val Leu Met Leu
            20                  25                  30 gag gcg cag gat ctc gct tgc gcg acc tct tcc gcc agt tca aaa ctc   144
Glu Ala Gln Asp Leu Ala Cys Ala Thr Ser Ser Ala Ser Ser Lys Leu
        35                  40                  45 att cac ggt ggc ctg cgc tac ctt gag cac tat gaa ttc cgc ctg gtc   192
Ile His Gly Gly Leu Arg Tyr Leu Glu His Tyr Glu Phe Arg Leu Val
    50                  55                  60 agc gag gcg ctg gct gaa cgt gaa gtg ctg ctg aaa atg gcc ccg cat   240
Ser Glu Ala Leu Ala Glu Arg Glu Val Leu Leu Lys Met Ala Pro His
65                  70                  75                  80 atc gcc ttc ccg atg cgt ttt cgc ctg cca cat cgt ccg cat ctg cgc   288
Ile Ala Phe Pro Met Arg Phe Arg Leu Pro His Arg Pro His Leu Arg
                85                  90                  95 ccg gcg tgg atg att cgc att ggt ctg ttt atg tac gat cat ctg ggt   336
Pro Ala Trp Met Ile Arg Ile Gly Leu Phe Met Tyr Asp His Leu Gly
            100                 105                 110 aaa cgc acc agc ttg ccg gga tca act ggt ttg cgt ttt ggc gca aat   384
Lys Arg Thr Ser Leu Pro Gly Ser Thr Gly Leu Arg Phe Gly Ala Asn
        115                 120                 125 tca gtg tta aaa ccg gaa att aag cgc gga ttc gaa tat tct gac tgt   432
Ser Val Leu Lys Pro Glu Ile Lys Arg Gly Phe Glu Tyr Ser Asp Cys
    130                 135                 140 tgg gta gac gac gcc cgt ctg gta ctc gcc aac gcc cag atg gtg gtg   480
Trp Val Asp Asp Ala Arg Leu Val Leu Ala Asn Ala Gln Met Val Val
145                 150                 155                 160
```

| | | |
|---|---|---|
| cgt aaa ggc ggc gaa gtg ctt act cgg act cgc gcc acc tct gct cgc<br>Arg Lys Gly Gly Glu Val Leu Thr Arg Thr Arg Ala Thr Ser Ala Arg<br>165 170 175 | | 528 |
| cgc gaa aac ggc ctg tgg att gtg gaa gcg gaa gat atc gat acc ggc<br>Arg Glu Asn Gly Leu Trp Ile Val Glu Ala Glu Asp Ile Asp Thr Gly<br>180 185 190 | | 576 |
| aaa aaa tat agc tgg caa gcg cgc ggc ttg gtt aac gcc acc ggc ccg<br>Lys Lys Tyr Ser Trp Gln Ala Arg Gly Leu Val Asn Ala Thr Gly Pro<br>195 200 205 | | 624 |
| tgg gtg aaa cag ttc ttc gac gac ggg atg cat ctg cct tcg cct tat<br>Trp Val Lys Gln Phe Phe Asp Asp Gly Met His Leu Pro Ser Pro Tyr<br>210 215 220 | | 672 |
| ggc att cgc ctg atc aaa ggc agc cat att gtg gtg ccg cgc gtg cat<br>Gly Ile Arg Leu Ile Lys Gly Ser His Ile Val Val Pro Arg Val His<br>225 230 235 240 | | 720 |
| acc cag aag caa gcc tac att ctg caa aac gaa gat aaa cgt att gtg<br>Thr Gln Lys Gln Ala Tyr Ile Leu Gln Asn Glu Asp Lys Arg Ile Val<br>245 250 255 | | 768 |
| ttc gtg atc ccg tgg atg gac gag ttt tcc atc atc ggc act acc gat<br>Phe Val Ile Pro Trp Met Asp Glu Phe Ser Ile Ile Gly Thr Thr Asp<br>260 265 270 | | 816 |
| gtc gag tac aaa ggc gat ccg aaa gcg gtg aag att gaa gag agt gaa<br>Val Glu Tyr Lys Gly Asp Pro Lys Ala Val Lys Ile Glu Glu Ser Glu<br>275 280 285 | | 864 |
| atc aat tac ctg ctg aat gtg tat aac acg cac ttt aaa aag cag tta<br>Ile Asn Tyr Leu Leu Asn Val Tyr Asn Thr His Phe Lys Lys Gln Leu<br>290 295 300 | | 912 |
| agc cgt gac gat atc gtc tgg acc tac tcc ggt gtg cgt ccg ctg tgt<br>Ser Arg Asp Asp Ile Val Trp Thr Tyr Ser Gly Val Arg Pro Leu Cys<br>305 310 315 320 | | 960 |
| gat gat gag tcc gac tcg ccg cag gct att acc cgt gat tac acc ctt<br>Asp Asp Glu Ser Asp Ser Pro Gln Ala Ile Thr Arg Asp Tyr Thr Leu<br>325 330 335 | | 1008 |
| gat att cat gat gaa aat ggc aaa gca ccg ctg ctg tcg gta ttc ggc<br>Asp Ile His Asp Glu Asn Gly Lys Ala Pro Leu Leu Ser Val Phe Gly<br>340 345 350 | | 1056 |
| ggt aag ctg acc acc tac cga aaa ctg gcg gaa cat gcg ctg gaa aaa<br>Gly Lys Leu Thr Thr Tyr Arg Lys Leu Ala Glu His Ala Leu Glu Lys<br>355 360 365 | | 1104 |
| cta acg ccg tat tat cag ggt att ggc ccg gca tgg acg aaa gag agt<br>Leu Thr Pro Tyr Tyr Gln Gly Ile Gly Pro Ala Trp Thr Lys Glu Ser<br>370 375 380 | | 1152 |
| gtg cta ccg ggt ggc gcc att gaa ggc gac cgc gac gat tat gcc gct<br>Val Leu Pro Gly Gly Ala Ile Glu Gly Asp Arg Asp Asp Tyr Ala Ala<br>385 390 395 400 | | 1200 |
| cgc ctg cgc cgc cgc tat ccg ttc ctg act gaa tcg ctg gcg cgt cat<br>Arg Leu Arg Arg Arg Tyr Pro Phe Leu Thr Glu Ser Leu Ala Arg His<br>405 410 415 | | 1248 |
| tac gct cgc act tac ggc agc aac agc gag ctg ctc ggc aat gcg<br>Tyr Ala Arg Thr Tyr Gly Ser Asn Ser Glu Leu Leu Leu Gly Asn Ala<br>420 425 430 | | 1296 |
| gga acg gta agc gat ctc ggg gaa gat ttc ggt cat gag ttc tac gaa<br>Gly Thr Val Ser Asp Leu Gly Glu Asp Phe Gly His Glu Phe Tyr Glu<br>435 440 445 | | 1344 |
| gcg gag ctg aaa tac ctg gtg gat cac gaa tgg gtc cgc cgc gcc gac<br>Ala Glu Leu Lys Tyr Leu Val Asp His Glu Trp Val Arg Arg Ala Asp<br>450 455 460 | | 1392 |
| gac gcc ctg tgg cgt cgc aca aaa caa ggc atg tgg cta aat gcg gat<br>Asp Ala Leu Trp Arg Arg Thr Lys Gln Gly Met Trp Leu Asn Ala Asp<br>465 470 475 480 | | 1440 |

```
caa caa tct cgt gtg agt cag tgg ctg gtg gag tat acg cag cag agg      1488
Gln Gln Ser Arg Val Ser Gln Trp Leu Val Glu Tyr Thr Gln Gln Arg
            485                 490                 495 tta tcg ctg gcg tcg taa                                               1506
Leu Ser Leu Ala Ser
            500

<210> SEQ ID NO 12
<211> LENGTH: 501
<212> TYPE: PRT
<213> ORGANISM: Escherichia coli

<400> SEQUENCE: 12

Met Glu Thr Lys Asp Leu Ile Val Ile Gly Gly Ile Asn Gly Ala
1               5                   10                  15

Gly Ile Ala Ala Asp Ala Ala Gly Arg Gly Leu Ser Val Leu Met Leu
                20                  25                  30

Glu Ala Gln Asp Leu Ala Cys Ala Thr Ser Ser Ala Ser Ser Lys Leu
            35                  40                  45

Ile His Gly Gly Leu Arg Tyr Leu Glu His Tyr Glu Phe Arg Leu Val
        50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Leu Arg Phe Gly Ala Asn
        115                 120                 125

Ser Val Leu Lys Pro Glu Ile Lys Arg Gly Phe Glu Tyr Ser Asp Cys
    130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
            180                 185                 190

Lys Lys Tyr Ser Trp Gln Ala Arg Gly Leu Val Asn Ala Thr Gly Pro
        195                 200                 205

Trp Val Lys Gln Phe Phe Asp Asp Gly Met His Leu Pro Ser Pro Tyr
    210                 215                 220

Gly Ile Arg Leu Ile Lys Gly Ser His Ile Val Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
            260                 265                 270

Val Glu Tyr Lys Gly Asp Pro Lys Ala Val Lys Ile Glu Glu Ser Glu
        275                 280                 285

Ile Asn Tyr Leu Leu Asn Val Tyr Asn Thr His Phe Lys Lys Gln Leu
    290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335
```

-continued

```
Asp Ile His Asp Glu Asn Gly Lys Ala Pro Leu Leu Ser Val Phe Gly
            340                 345                 350
Gly Lys Leu Thr Thr Tyr Arg Lys Leu Ala Glu His Ala Leu Glu Lys
        355                 360                 365
Leu Thr Pro Tyr Tyr Gln Gly Ile Gly Pro Ala Trp Thr Lys Glu Ser
    370                 375                 380
Val Leu Pro Gly Gly Ala Ile Glu Gly Asp Arg Asp Tyr Ala Ala
385                 390                 395                 400
Arg Leu Arg Arg Arg Tyr Pro Phe Leu Thr Glu Ser Leu Ala Arg His
                405                 410                 415
Tyr Ala Arg Thr Tyr Gly Ser Asn Ser Glu Leu Leu Gly Asn Ala
            420                 425                 430
Gly Thr Val Ser Asp Leu Gly Glu Asp Phe Gly His Glu Phe Tyr Glu
        435                 440                 445
Ala Glu Leu Lys Tyr Leu Val Asp His Glu Trp Val Arg Arg Ala Asp
    450                 455                 460
Asp Ala Leu Trp Arg Arg Thr Lys Gln Gly Met Trp Leu Asn Ala Asp
465                 470                 475                 480
Gln Gln Ser Arg Val Ser Gln Trp Leu Val Glu Tyr Thr Gln Gln Arg
                485                 490                 495
Leu Ser Leu Ala Ser
            500
```

<210> SEQ ID NO 13
<211> LENGTH: 19
<212> TYPE: DNA
<213> ORGANISM: Artificial
<220> FEATURE:
<223> OTHER INFORMATION: primer P1

<400> SEQUENCE: 13
aaccacatac acaccattg                                        19

<210> SEQ ID NO 14
<211> LENGTH: 18
<212> TYPE: DNA
<213> ORGANISM: Artificial
<220> FEATURE:
<223> OTHER INFORMATION: primer P2

<400> SEQUENCE: 14
acgacaaaat gctggaag                                         18

<210> SEQ ID NO 15
<211> LENGTH: 59
<212> TYPE: DNA
<213> ORGANISM: Artificial
<220> FEATURE:
<223> OTHER INFORMATION: primer P3

<400> SEQUENCE: 15
tgctgccaga agtgcgtcgt tcttccgaag tataccgctc aagttagtat aaaaaagct   59

<210> SEQ ID NO 16
<211> LENGTH: 60
<212> TYPE: DNA
<213> ORGANISM: Artificial
<220> FEATURE:
<223> OTHER INFORMATION: primer P4

```
<400> SEQUENCE: 16
ctgctggtca ccggcgatcc cggagattgg aatacgtgaa gcctgctttt ttatactaag      60

<210> SEQ ID NO 17
<211> LENGTH: 70
<212> TYPE: DNA
<213> ORGANISM: Artificial
<220> FEATURE:
<223> OTHER INFORMATION: primer P5

<400> SEQUENCE: 17
gatgctgcca gaagtgcgtc gttcttccga agtatacggt cagactaaca ttgacggcaa      60
aggcggcacg                                                            70

<210> SEQ ID NO 18
<211> LENGTH: 70
<212> TYPE: DNA
<213> ORGANISM: Artificial
<220> FEATURE:
<223> OTHER INFORMATION: primer P6

<400> SEQUENCE: 18
ctgctggtca ccggcgatcc cggagattgg aatacgcgtg ccgcctttgc cgtcaatgtt      60
agtctgaccg                                                            70

<210> SEQ ID NO 19
<211> LENGTH: 70
<212> TYPE: DNA
<213> ORGANISM: Artificial
<220> FEATURE:
<223> OTHER INFORMATION: primer P7

<400> SEQUENCE: 19
gatgctgcca gaagtgcgtc gttcttccga agtatacggt cagactaaca ttgacggcaa      60
agacggcacg                                                            70

<210> SEQ ID NO 20
<211> LENGTH: 69
<212> TYPE: DNA
<213> ORGANISM: Artificial
<220> FEATURE:
<223> OTHER INFORMATION: primer P8

<400> SEQUENCE: 20
ctgctggtca ccggcgatcc cggagattgg aatacgcgtg ccgtctttgc cgcaatgtta      60
gtctgaccg                                                             69

<210> SEQ ID NO 21
<211> LENGTH: 70
<212> TYPE: DNA
<213> ORGANISM: Artificial
<220> FEATURE:
<223> OTHER INFORMATION: primer P9

<400> SEQUENCE: 21
ctgctggtca ccggcgatcc cggagattgg aatacgcgth dvhddtvtgc cgccaatgtt      60
agtctgaccg                                                            70

<210> SEQ ID NO 22
<211> LENGTH: 70
<212> TYPE: DNA
<213> ORGANISM: Artificial
```

<220> FEATURE:
<223> OTHER INFORMATION: primer P10

<400> SEQUENCE: 22
gatgctgcca gaagtgcgtc gttcttccga agtatacggt cagactaaca tthhdhhdba    60
aggcggcacg    70

<210> SEQ ID NO 23
<211> LENGTH: 60
<212> TYPE: DNA
<213> ORGANISM: Artificial
<220> FEATURE:
<223> OTHER INFORMATION: primer P11

<400> SEQUENCE: 23
tcagcacagc tccagttgaa tatggtggtc cgtcagtgaa gcctgctttt ttatactaag    60

<210> SEQ ID NO 24
<211> LENGTH: 59
<212> TYPE: DNA
<213> ORGANISM: Artificial
<220> FEATURE:
<223> OTHER INFORMATION: primer P12

<400> SEQUENCE: 24
atgaaacaaa cacaacgtca caacggtatt atcgacgctc aagttagtat aaaaaagct    59

<210> SEQ ID NO 25
<211> LENGTH: 18
<212> TYPE: DNA
<213> ORGANISM: Artificial
<220> FEATURE:
<223> OTHER INFORMATION: primer P13

<400> SEQUENCE: 25
ttgcgctgat ctggattg    18

<210> SEQ ID NO 26
<211> LENGTH: 19
<212> TYPE: DNA
<213> ORGANISM: Artificial
<220> FEATURE:
<223> OTHER INFORMATION: primer P14

<400> SEQUENCE: 26
aacatcgatc tcttcgacc    19

<210> SEQ ID NO 27
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 27
ggcggcaaag acggc    15

<210> SEQ ID NO 28
<211> LENGTH: 15
<212> TYPE: DNA
<213> ORGANISM: Artificial
<220> FEATURE:
<223> OTHER INFORMATION: DNA fragment coding 231-235 region of GlpK -continued

<400> SEQUENCE: 28
ggcggcagaa tacta                                                      15

<210> SEQ ID NO 29
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 29
ggcggcagac ttgaa                                                      15

<210> SEQ ID NO 30
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 30
ggcggcaaaa cgttt                                                      15

<210> SEQ ID NO 31
<211> LENGTH: 759
<212> TYPE: DNA
<213> ORGANISM: Escherichia coli
<220> FEATURE:
<221> NAME/KEY: CDS
<222> LOCATION: (1)..(759)

<400> SEQUENCE: 31

```
atg aaa caa aca caa cgt cac aac ggt att atc gaa ctg gtt aaa cag        48
Met Lys Gln Thr Gln Arg His Asn Gly Ile Ile Glu Leu Val Lys Gln
1               5                  10                  15 cag ggt tat gtc agt acc gaa gag ctg gta gag cat ttc tcc gtc agc        96
Gln Gly Tyr Val Ser Thr Glu Glu Leu Val Glu His Phe Ser Val Ser
                20                  25                  30 ccg cag act att cgc cgc gac ctc aat gag ctg gcg gag caa aac ctg       144
Pro Gln Thr Ile Arg Arg Asp Leu Asn Glu Leu Ala Glu Gln Asn Leu
            35                  40                  45 atc ctg cgc cat cat ggc ggt gcg gcg ctg cct tcc agt tcg gtt aac       192
Ile Leu Arg His His Gly Gly Ala Ala Leu Pro Ser Ser Ser Val Asn
        50                  55                  60 acg ccg tgg cac gat cgc aag gcc acc cag acc gaa gaa aaa gag cgc       240
Thr Pro Trp His Asp Arg Lys Ala Thr Gln Thr Glu Glu Lys Glu Arg
65                  70                  75                  80 atc gcc cgc aaa gtg gcg gag caa atc ccc aat ggc tcg acg ctg ttt       288
Ile Ala Arg Lys Val Ala Glu Gln Ile Pro Asn Gly Ser Thr Leu Phe
                85                  90                  95 atc gat atc ggc acc acg ccg gaa gcg gta gcg cac gca ctg ctc aat       336
Ile Asp Ile Gly Thr Thr Pro Glu Ala Val Ala His Ala Leu Leu Asn
                100                 105                 110 cac agc aat ttg cgc att gtc acc aac aat ctc aac gtt gct aac acg       384
His Ser Asn Leu Arg Ile Val Thr Asn Asn Leu Asn Val Ala Asn Thr
            115                 120                 125 ttg atg gta aaa gaa gat ttt cgc atc att ctc gcc ggt ggc gaa tta       432
Leu Met Val Lys Glu Asp Phe Arg Ile Ile Leu Ala Gly Gly Glu Leu
        130                 135                 140 cgc agc cgc gat ggc ggg atc att ggc gaa gcg acg ctc gat ttt atc       480
Arg Ser Arg Asp Gly Gly Ile Ile Gly Glu Ala Thr Leu Asp Phe Ile
145                 150                 155                 160
```

```
tcc cag ttc cgc ctt gat ttc ggc att ctg ggg ata agc ggc atc gat      528
Ser Gln Phe Arg Leu Asp Phe Gly Ile Leu Gly Ile Ser Gly Ile Asp
                165                 170                 175 agc gac ggc tcg ctg ctg gag ttc gat tac cac gaa gtt cgc acc aaa      576
Ser Asp Gly Ser Leu Leu Glu Phe Asp Tyr His Glu Val Arg Thr Lys
            180                 185                 190 cgc gcc att att gag aac tcg cgc cac gtt atg ctg gtc gat cac          624
Arg Ala Ile Ile Glu Asn Ser Arg His Val Met Leu Val Asp His
        195                 200                 205 tcg aaa ttt ggc cgt aac gcg atg gtc aat atg ggc agc atc agc atg      672
Ser Lys Phe Gly Arg Asn Ala Met Val Asn Met Gly Ser Ile Ser Met
    210                 215                 220 gta gat gcc gtc tac acc gac gcc ccg ccg cca gta agc gtg atg cag      720
Val Asp Ala Val Tyr Thr Asp Ala Pro Pro Pro Val Ser Val Met Gln
225                 230                 235                 240 gtg ctg acg gac cac cat att caa ctg gag ctg tgc tga                  759
Val Leu Thr Asp His His Ile Gln Leu Glu Leu Cys
                245                 250

<210> SEQ ID NO 32
<211> LENGTH: 252
<212> TYPE: PRT
<213> ORGANISM: Escherichia coli

<400> SEQUENCE: 32

Met Lys Gln Thr Gln Arg His Asn Gly Ile Ile Glu Leu Val Lys Gln
1               5                   10                  15

Gln Gly Tyr Val Ser Thr Glu Glu Leu Val Glu His Phe Ser Val Ser
            20                  25                  30

Pro Gln Thr Ile Arg Arg Asp Leu Asn Glu Leu Ala Glu Gln Asn Leu
        35                  40                  45

Ile Leu Arg His His Gly Gly Ala Ala Leu Pro Ser Ser Ser Val Asn
    50                  55                  60

Thr Pro Trp His Asp Arg Lys Ala Thr Gln Thr Glu Glu Lys Glu Arg
65                  70                  75                  80

Ile Ala Arg Lys Val Ala Glu Gln Ile Pro Asn Gly Ser Thr Leu Phe
                85                  90                  95

Ile Asp Ile Gly Thr Thr Pro Glu Ala Val Ala His Ala Leu Leu Asn
            100                 105                 110

His Ser Asn Leu Arg Ile Val Thr Asn Asn Leu Asn Val Ala Asn Thr
        115                 120                 125

Leu Met Val Lys Glu Asp Phe Arg Ile Ile Leu Ala Gly Gly Glu Leu
    130                 135                 140

Arg Ser Arg Asp Gly Gly Ile Ile Gly Glu Ala Thr Leu Asp Phe Ile
145                 150                 155                 160

Ser Gln Phe Arg Leu Asp Phe Gly Ile Leu Gly Ile Ser Gly Ile Asp
                165                 170                 175

Ser Asp Gly Ser Leu Leu Glu Phe Asp Tyr His Glu Val Arg Thr Lys
            180                 185                 190

Arg Ala Ile Ile Glu Asn Ser Arg His Val Met Leu Val Asp His
        195                 200                 205

Ser Lys Phe Gly Arg Asn Ala Met Val Asn Met Gly Ser Ile Ser Met
    210                 215                 220

Val Asp Ala Val Tyr Thr Asp Ala Pro Pro Pro Val Ser Val Met Gln
225                 230                 235                 240

Val Leu Thr Asp His His Ile Gln Leu Glu Leu Cys
                245                 250
```

<210> SEQ ID NO 33
<211> LENGTH: 768
<212> TYPE: DNA
<213> ORGANISM: Escherichia coli
<220> FEATURE:
<221> NAME/KEY: CDS
<222> LOCATION: (1)..(768)

<400> SEQUENCE: 33

```
atg cga cat cct tta gtg atg ggt aac tgg aaa ctg aac ggc agc cgc      48
Met Arg His Pro Leu Val Met Gly Asn Trp Lys Leu Asn Gly Ser Arg
1               5                   10                  15 cac atg gtt cac gag ctg gtt tct aac ctg cgt aaa gag ctg gca ggt      96
His Met Val His Glu Leu Val Ser Asn Leu Arg Lys Glu Leu Ala Gly
            20                  25                  30 gtt gct ggc tgt gcg gtt gca atc gca cca ccg gaa atg tat atc gat     144
Val Ala Gly Cys Ala Val Ala Ile Ala Pro Pro Glu Met Tyr Ile Asp
        35                  40                  45 atg gcg aag cgc gaa gct gaa ggc agc cac atc atg ctg ggt gcg caa     192
Met Ala Lys Arg Glu Ala Glu Gly Ser His Ile Met Leu Gly Ala Gln
    50                  55                  60 aac gtg gac ctg aac ctg tcc ggc gca ttc acc ggt gaa acc tct gct     240
Asn Val Asp Leu Asn Leu Ser Gly Ala Phe Thr Gly Glu Thr Ser Ala
65                  70                  75                  80 gct atg ctg aaa gac atc ggc gca cag tac atc atc atc ggt cac tct     288
Ala Met Leu Lys Asp Ile Gly Ala Gln Tyr Ile Ile Ile Gly His Ser
                85                  90                  95 gaa cgt cgt act tac cac aaa gaa tct gac gaa ctg atc gcg aaa aaa     336
Glu Arg Arg Thr Tyr His Lys Glu Ser Asp Glu Leu Ile Ala Lys Lys
            100                 105                 110 ttc gcg gtg ctg aaa gag cag ggc ctg act ccg gtt ctg tgc atc ggt     384
Phe Ala Val Leu Lys Glu Gln Gly Leu Thr Pro Val Leu Cys Ile Gly
        115                 120                 125 gaa acc gaa gct gaa aat gaa gcg ggc aaa act gaa gaa gtt tgc gca     432
Glu Thr Glu Ala Glu Asn Glu Ala Gly Lys Thr Glu Glu Val Cys Ala
    130                 135                 140 cgt cag atc gac gcg gta ctg aaa act cag ggt gct gcg gca ttc gaa     480
Arg Gln Ile Asp Ala Val Leu Lys Thr Gln Gly Ala Ala Ala Phe Glu
145                 150                 155                 160 ggt gcg gtt atc gct tac gaa cct gta tgg gca atc ggt act ggc aaa     528
Gly Ala Val Ile Ala Tyr Glu Pro Val Trp Ala Ile Gly Thr Gly Lys
                165                 170                 175 tct gca act ccg gct cag gca cag gct gtt cac aaa ttc atc cgt gac     576
Ser Ala Thr Pro Ala Gln Ala Gln Ala Val His Lys Phe Ile Arg Asp
            180                 185                 190 cac atc gct aaa gtt gac gct aac atc gct gaa caa gtg atc att cag     624
His Ile Ala Lys Val Asp Ala Asn Ile Ala Glu Gln Val Ile Ile Gln
        195                 200                 205 tac ggc ggc tct gta aac gcg tct aac gct gca gaa ctg ttt gct cag     672
Tyr Gly Gly Ser Val Asn Ala Ser Asn Ala Ala Glu Leu Phe Ala Gln
    210                 215                 220 ccg gat atc gac ggc gcg ctg gtt ggt ggt gct tct ctg aaa gct gac     720
Pro Asp Ile Asp Gly Ala Leu Val Gly Gly Ala Ser Leu Lys Ala Asp
225                 230                 235                 240 gcc ttc gca gta atc gtt aaa gct gca gaa gcg gct aaa cag gct taa     768
Ala Phe Ala Val Ile Val Lys Ala Ala Glu Ala Ala Lys Gln Ala
                245                 250                 255
```

<210> SEQ ID NO 34
<211> LENGTH: 255
<212> TYPE: PRT
<213> ORGANISM: Escherichia coli

<400> SEQUENCE: 34

| Met | Arg | His | Pro | Leu | Val | Met | Gly | Asn | Trp | Lys | Leu | Asn | Gly | Ser | Arg |
|---|---|---|---|---|---|---|---|---|---|---|---|---|---|---|---|
| 1 | | | | 5 | | | | | 10 | | | | | 15 | |

| His | Met | Val | His | Glu | Leu | Val | Ser | Asn | Leu | Arg | Lys | Glu | Leu | Ala | Gly |
|---|---|---|---|---|---|---|---|---|---|---|---|---|---|---|---|
| | | | 20 | | | | 25 | | | | | 30 | | | |

| Val | Ala | Gly | Cys | Ala | Val | Ala | Ile | Ala | Pro | Pro | Glu | Met | Tyr | Ile | Asp |
|---|---|---|---|---|---|---|---|---|---|---|---|---|---|---|---|
| | | | 35 | | | | 40 | | | | 45 | | | | |

| Met | Ala | Lys | Arg | Glu | Ala | Glu | Gly | Ser | His | Ile | Met | Leu | Gly | Ala | Gln |
|---|---|---|---|---|---|---|---|---|---|---|---|---|---|---|---|
| 50 | | | | | 55 | | | | | 60 | | | | | |

| Asn | Val | Asp | Leu | Asn | Leu | Ser | Gly | Ala | Phe | Thr | Gly | Glu | Thr | Ser | Ala |
|---|---|---|---|---|---|---|---|---|---|---|---|---|---|---|---|
| 65 | | | | | 70 | | | | | 75 | | | | | 80 |

| Ala | Met | Leu | Lys | Asp | Ile | Gly | Ala | Gln | Tyr | Ile | Ile | Ile | Gly | His | Ser |
|---|---|---|---|---|---|---|---|---|---|---|---|---|---|---|---|
| | | | | 85 | | | | | 90 | | | | | 95 | |

| Glu | Arg | Arg | Thr | Tyr | His | Lys | Glu | Ser | Asp | Glu | Leu | Ile | Ala | Lys | Lys |
|---|---|---|---|---|---|---|---|---|---|---|---|---|---|---|---|
| | | | 100 | | | | | 105 | | | | | 110 | | |

| Phe | Ala | Val | Leu | Lys | Glu | Gln | Gly | Leu | Thr | Pro | Val | Leu | Cys | Ile | Gly |
|---|---|---|---|---|---|---|---|---|---|---|---|---|---|---|---|
| | | 115 | | | | | 120 | | | | | 125 | | | |

| Glu | Thr | Glu | Ala | Glu | Asn | Glu | Ala | Gly | Lys | Thr | Glu | Glu | Val | Cys | Ala |
|---|---|---|---|---|---|---|---|---|---|---|---|---|---|---|---|
| 130 | | | | | 135 | | | | | 140 | | | | | |

| Arg | Gln | Ile | Asp | Ala | Val | Leu | Lys | Thr | Gln | Gly | Ala | Ala | Ala | Phe | Glu |
|---|---|---|---|---|---|---|---|---|---|---|---|---|---|---|---|
| 145 | | | | | 150 | | | | | 155 | | | | | 160 |

| Gly | Ala | Val | Ile | Ala | Tyr | Glu | Pro | Val | Trp | Ala | Ile | Gly | Thr | Gly | Lys |
|---|---|---|---|---|---|---|---|---|---|---|---|---|---|---|---|
| | | | | 165 | | | | | 170 | | | | | 175 | |

| Ser | Ala | Thr | Pro | Ala | Gln | Ala | Gln | Ala | Val | His | Lys | Phe | Ile | Arg | Asp |
|---|---|---|---|---|---|---|---|---|---|---|---|---|---|---|---|
| | | | 180 | | | | | 185 | | | | | 190 | | |

| His | Ile | Ala | Lys | Val | Asp | Ala | Asn | Ile | Ala | Glu | Gln | Val | Ile | Ile | Gln |
|---|---|---|---|---|---|---|---|---|---|---|---|---|---|---|---|
| | | 195 | | | | | 200 | | | | | 205 | | | |

| Tyr | Gly | Gly | Ser | Val | Asn | Ala | Ser | Asn | Ala | Ala | Glu | Leu | Phe | Ala | Gln |
|---|---|---|---|---|---|---|---|---|---|---|---|---|---|---|---|
| 210 | | | | | 215 | | | | | 220 | | | | | |

| Pro | Asp | Ile | Asp | Gly | Ala | Leu | Val | Gly | Gly | Ala | Ser | Leu | Lys | Ala | Asp |
|---|---|---|---|---|---|---|---|---|---|---|---|---|---|---|---|
| 225 | | | | | 230 | | | | | 235 | | | | | 240 |

| Ala | Phe | Ala | Val | Ile | Val | Lys | Ala | Ala | Glu | Ala | Ala | Lys | Gln | Ala |
|---|---|---|---|---|---|---|---|---|---|---|---|---|---|---|
| | | | | 245 | | | | | 250 | | | | | 255 |

<210> SEQ ID NO 35
<211> LENGTH: 70
<212> TYPE: DNA
<213> ORGANISM: Artificial
<220> FEATURE:
<223> OTHER INFORMATION: primer P15

<400> SEQUENCE: 35
gatgaaagcg ttatccaaac tgaaagcgga agaggccgac gcactttgcg ccgaataaat    60
acctgtgacg    70

<210> SEQ ID NO 36
<211> LENGTH: 69
<212> TYPE: DNA
<213> ORGANISM: Artificial
<220> FEATURE:
<223> OTHER INFORMATION: primer P16

<400> SEQUENCE: 36
ttaatcccag ctcagaataa ctttcccgga ctttacgccc cgccctgcca ctcatcgcag    60
tactgttgt    69

```
<210> SEQ ID NO 37
<211> LENGTH: 18
<212> TYPE: DNA
<213> ORGANISM: Artificial
<220> FEATURE:
<223> OTHER INFORMATION: primer P17

<400> SEQUENCE: 37
cggtcatgct tggtgatg                                                 18

<210> SEQ ID NO 38
<211> LENGTH: 21
<212> TYPE: DNA
<213> ORGANISM: Artificial
<220> FEATURE:
<223> OTHER INFORMATION: primer P18

<400> SEQUENCE: 38
ttaatcccag ctcagaataa c                                             21

<210> SEQ ID NO 39
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 39
ggcggcagaa tacct                                                    15

<210> SEQ ID NO 40
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 40
ggcggcacat tgtta                                                    15

<210> SEQ ID NO 41
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 41
cgggaagctc gagcc                                                    15

<210> SEQ ID NO 42
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 42
cgagcacacc ttgcc                                                    15

<210> SEQ ID NO 43
<211> LENGTH: 510
<212> TYPE: PRT
<213> ORGANISM: Shigella sonnei
```

<400> SEQUENCE: 43

```
Met Thr Thr Gly Gln Leu Asn Met Thr Glu Lys Lys Tyr Ile Val Ala
1               5                   10                  15
Leu Asp Gln Gly Thr Thr Ser Ser Arg Ala Val Val Met Asp His Asp
            20                  25                  30
Ala Asn Ile Ile Ser Val Ser Gln Arg Glu Phe Glu Gln Ile Tyr Pro
        35                  40                  45
Lys Pro Gly Trp Val Glu His Asp Pro Met Glu Ile Trp Ala Thr Gln
    50                  55                  60
Ser Ser Thr Leu Val Glu Val Leu Ala Lys Ala Asp Ile Ser Ser Asp
65                  70                  75                  80
Gln Ile Ala Ala Ile Gly Ile Thr Asn Gln Arg Glu Thr Thr Ile Val
                85                  90                  95
Trp Glu Lys Glu Thr Gly Lys Pro Ile Tyr Asn Ala Ile Val Trp Gln
            100                 105                 110
Cys Arg Arg Thr Ala Glu Ile Cys Glu His Leu Lys Arg Asp Gly Leu
        115                 120                 125
Glu Asp Tyr Ile Arg Ser Asn Thr Gly Leu Val Ile Asp Pro Tyr Phe
    130                 135                 140
Ser Gly Thr Lys Val Lys Trp Ile Leu Asp His Val Glu Gly Ser Arg
145                 150                 155                 160
Glu Arg Ala Arg Arg Gly Glu Leu Leu Phe Gly Thr Val Asp Thr Trp
                165                 170                 175
Leu Ile Trp Lys Met Thr Gln Gly Arg Val His Val Thr Asp Tyr Thr
            180                 185                 190
Asn Ala Ser Arg Thr Met Leu Phe Asn Ile His Thr Leu Asp Trp Asp
        195                 200                 205
Asp Lys Met Leu Glu Val Leu Asp Ile Pro Arg Glu Met Leu Pro Glu
    210                 215                 220
Val Arg Arg Ser Ser Glu Val Tyr Gly Gln Thr Asn Ile Gly Gly Lys
225                 230                 235                 240
Gly Gly Thr Arg Ile Pro Ile Ser Gly Ile Ala Gly Asp Gln Gln Ala
                245                 250                 255
Ala Leu Phe Gly Gln Leu Cys Val Lys Glu Gly Met Ala Lys Asn Thr
            260                 265                 270
Tyr Gly Thr Gly Cys Phe Met Leu Met Asn Thr Gly Glu Lys Ala Val
        275                 280                 285
Lys Ser Glu Asn Gly Leu Leu Thr Thr Ile Ala Cys Gly Pro Thr Gly
    290                 295                 300
Glu Val Asn Tyr Ala Leu Glu Gly Ala Val Phe Met Ala Gly Ala Ser
305                 310                 315                 320
Ile Gln Trp Leu Arg Asp Glu Met Lys Leu Ile Asn Asp Ala Tyr Asp
                325                 330                 335
Ser Glu Tyr Phe Ala Thr Lys Val Gln Asn Thr Asn Gly Val Tyr Val
            340                 345                 350
Val Pro Ala Phe Thr Gly Leu Gly Ala Pro Tyr Trp Asp Pro Tyr Ala
        355                 360                 365
Arg Gly Ala Ile Phe Gly Leu Thr Arg Gly Val Asn Ala Asn His Ile
    370                 375                 380
Ile Arg Ala Thr Leu Glu Ser Ile Ala Tyr Gln Thr Arg Asp Val Leu
385                 390                 395                 400
Glu Ala Met Gln Ala Asp Ser Gly Ile Arg Leu His Ala Leu Arg Val
                405                 410                 415
```

```
Asp Gly Gly Ala Val Ala Asn Asn Phe Leu Met Gln Phe Gln Ser Asp
            420                 425                 430

Ile Leu Gly Thr Arg Val Glu Arg Pro Glu Val Arg Glu Val Thr Ala
        435                 440                 445

Leu Gly Ala Ala Tyr Leu Ala Gly Leu Ala Val Gly Phe Trp Gln Asn
    450                 455                 460

Leu Asp Glu Leu Gln Glu Lys Ala Val Ile Glu Arg Glu Phe Arg Pro
465                 470                 475                 480

Gly Ile Glu Thr Thr Glu Arg Asn Tyr Arg Tyr Ala Gly Trp Lys Lys
                485                 490                 495

Ala Val Lys Arg Ala Met Ala Trp Glu Glu His Asp Val Met
            500                 505                 510

<210> SEQ ID NO 44
<211> LENGTH: 507
<212> TYPE: PRT
<213> ORGANISM: Yersinia pestis

<400> SEQUENCE: 44

Met Thr Thr Glu Asn Thr Thr Gln Lys Lys Tyr Ile Val Ala Leu Asp
1               5                   10                  15

Gln Gly Thr Thr Ser Ser Arg Ala Val Val Leu Asp His Asn Ala Asn
            20                  25                  30

Ile Val Ser Val Ser Gln Arg Glu Phe Thr Gln Ile Tyr Pro Lys Ala
        35                  40                  45

Gly Trp Val Glu His Asp Pro Met Glu Ile Trp Ala Thr Gln Ser Ser
    50                  55                  60

Thr Leu Ile Glu Val Leu Ala Lys Ala Gly Ile Asn Ser Asp Glu Ile
65                  70                  75                  80

Ala Gly Ile Gly Ile Thr Asn Gln Arg Glu Thr Thr Ile Val Trp Asp
                85                  90                  95

Lys Val Thr Gly Lys Pro Val Tyr Asn Ala Ile Val Trp Gln Cys Arg
            100                 105                 110

Arg Thr Ala Asp Ile Cys Glu Lys Leu Lys Lys Glu Gly Leu Glu Glu
        115                 120                 125

Tyr Ile Arg His Asn Thr Gly Leu Val Val Asp Pro Tyr Phe Ser Gly
    130                 135                 140

Thr Lys Val Lys Trp Ile Leu Asp Asn Val Glu Gly Ala Arg Glu Arg
145                 150                 155                 160

Ala Glu Arg Gly Glu Leu Leu Phe Gly Thr Val Asp Thr Trp Leu Val
                165                 170                 175

Trp Asn Met Thr Gln Gly Arg Val His Val Thr Asp Tyr Thr Asn Ala
            180                 185                 190

Ser Arg Thr Met Met Phe Asn Ile Arg Thr Lys Glu Trp Asp Asp Arg
        195                 200                 205

Met Leu Lys Ala Leu Asn Ile Pro Arg Ala Met Leu Pro Glu Val Arg
    210                 215                 220

Pro Ser Ser Glu Ile Tyr Gly Lys Thr Asn Ile Gly Gly Lys Gly Gly
225                 230                 235                 240

Thr Arg Ile Pro Ile Ala Gly Ile Ala Gly Asp Gln Gln Ala Ala Leu
                245                 250                 255

Phe Gly Gln Leu Cys Val Gln Pro Gly Met Ala Lys Asn Thr Tyr Gly
            260                 265                 270

Thr Gly Cys Phe Leu Leu Met Asn Thr Gly Glu Glu Ala Val Gln Ser
        275                 280                 285
```

```
Thr His Gly Leu Leu Thr Thr Ile Ala Cys Gly Pro Arg Gly Glu Val
    290                 295                 300

Asn Tyr Ala Leu Glu Gly Ala Val Phe Ile Gly Gly Ala Ser Ile Gln
305                 310                 315                 320

Trp Leu Arg Asp Glu Leu Lys Leu Ile Gly Asp Ala Thr Asp Ser Glu
                325                 330                 335

Tyr Phe Ala Thr Lys Val Lys Asn Ser Asn Gly Val Tyr Val Val Pro
                340                 345                 350

Ala Phe Thr Gly Leu Gly Ala Pro Tyr Trp Asp Pro Tyr Ala Arg Gly
                355                 360                 365

Ala Ile Phe Gly Leu Thr Arg Gly Val Asn Ser Asn His Ile Ile Arg
    370                 375                 380

Ala Thr Leu Glu Ser Ile Ala Tyr Gln Thr Arg Asp Val Leu Asp Ala
385                 390                 395                 400

Met Gln Ala Asp Ser Gly Ala Arg Leu Lys Ser Leu Arg Val Asp Gly
                405                 410                 415

Gly Ala Val Ala Asn Asn Phe Leu Met Gln Phe Gln Ala Asp Ile Leu
                420                 425                 430

Gly Thr Arg Val Glu Arg Pro Ala Ile Arg Glu Ser Thr Ala Leu Gly
            435                 440                 445

Ala Ala Phe Leu Ala Gly Leu Ala Thr Gly Phe Trp Asp Asp Leu Asp
    450                 455                 460

Glu Val Lys Ser Lys Ala Ser Ile Glu Arg Glu Phe Arg Pro Gly Ile
465                 470                 475                 480

Glu Thr Thr Glu Arg Asp Ile Arg Tyr Lys Gly Trp Lys Lys Ala Val
                485                 490                 495

Ala Arg Ala Arg Asp Trp Glu Glu His Asp Glu
            500                 505

<210> SEQ ID NO 45
<211> LENGTH: 505
<212> TYPE: PRT
<213> ORGANISM: Pseudomonas aeruginosa

<400> SEQUENCE: 45

Met Thr Asp Lys His Asn Lys Lys Tyr Val Val Ala Leu Asp Gln Gly
1               5                   10                  15

Thr Thr Ser Ser Arg Ala Ile Val Phe Asp Arg Asp Ala Asn Val Val
                20                  25                  30

Ser Gln Ala Gln Arg Glu Phe Ala Gln Phe Tyr Pro Gln Ala Gly Trp
            35                  40                  45

Val Glu His Asp Pro Met Glu Ile Trp Ala Thr Gln Ser Ser Thr Leu
    50                  55                  60

Val Glu Ala Leu Ala Gln Ala Ser Ile Glu His Asp Gln Val Ala Ala
65                  70                  75                  80

Ile Gly Ile Thr Asn Gln Arg Glu Thr Thr Val Val Trp Asp Arg His
                85                  90                  95

Ser Gly Arg Pro Ile His Asn Ala Ile Val Trp Gln Cys Arg Arg Ser
            100                 105                 110

Ala Ala Ile Cys Ala Gln Leu Lys Arg Asp Gly Leu Glu Asp Tyr Ile
    115                 120                 125

Arg Glu Thr Thr Gly Leu Val Thr Asp Pro Tyr Phe Ser Gly Thr Lys
130                 135                 140

Leu Lys Trp Ile Leu Asp Asn Val Glu Gly Ala Arg Glu Arg Ala Arg
145                 150                 155                 160
```

```
Asn Gly Asp Leu Leu Phe Gly Thr Ile Asp Thr Trp Leu Ile Trp Lys
            165                 170                 175
Leu Thr Glu Gly Lys Val His Val Thr Asp Tyr Thr Asn Ala Ser Arg
        180                 185                 190
Thr Met Leu Phe Asn Ile His Ser Arg Asp Trp Asp Ala Arg Met Leu
    195                 200                 205
Glu Val Leu Asp Ile Pro Arg Ser Met Leu Pro Glu Val Arg Asn Ser
210                 215                 220
Ser Glu Val Tyr Gly Asn Ala Arg Ile Gly Gly Val Gly Gly Gly Glu
225                 230                 235                 240
Leu Pro Ile Ala Gly Ile Ala Gly Asp Gln Gln Ala Ala Leu Phe Gly
                245                 250                 255
Gln Met Cys Val Glu Pro Gly Gln Ala Lys Asn Thr Tyr Gly Thr Gly
            260                 265                 270
Cys Phe Leu Leu Met His Thr Gly Asp Lys Ala Val Lys Ser Thr His
        275                 280                 285
Gly Leu Leu Thr Thr Ile Ala Cys Gly Pro Arg Gly Glu Val Gly Tyr
    290                 295                 300
Ala Leu Glu Gly Ala Val Phe Asn Gly Gly Ser Thr Val Gln Trp Leu
305                 310                 315                 320
Arg Asp Glu Leu Lys Val Ile Asn Asp Ser Phe Asp Ser Glu Tyr Phe
                325                 330                 335
Ala Thr Lys Val Lys Asp Ser Asn Gly Val Tyr Leu Val Pro Ala Phe
            340                 345                 350
Thr Gly Leu Gly Ala Pro Tyr Trp Asp Pro Tyr Ala Arg Gly Ala Val
        355                 360                 365
Phe Gly Leu Thr Arg Gly Val Lys Ala Asp His Leu Ile Arg Ala Thr
    370                 375                 380
Leu Glu Ser Ile Ala Tyr Gln Thr Arg Asp Val Leu Asp Ala Met Gln
385                 390                 395                 400
Arg Asp Ala Gly Glu Arg Leu Arg Ala Leu Arg Val Asp Gly Gly Ala
                405                 410                 415
Val Ala Asn Asn Phe Leu Met Gln Phe Gln Ala Asp Ile Leu Gly Thr
            420                 425                 430
Arg Val Glu Arg Pro Val Met Arg Glu Thr Thr Ala Leu Gly Ala Ala
        435                 440                 445
Tyr Leu Ala Gly Leu Ala Cys Gly Phe Trp Ser Ser Leu Asp Glu Leu
    450                 455                 460
Lys Ser Lys Ala Val Ile Glu Arg Val Phe Glu Pro Glu Cys Asp Glu
465                 470                 475                 480
Pro Arg Arg Glu Lys Leu Tyr Ala Gly Trp Lys Lys Ala Val Glu Arg
                485                 490                 495
Thr Arg Gly Trp Asp Asp Gly Glu Leu
            500                 505

<210> SEQ ID NO 46
<211> LENGTH: 496
<212> TYPE: PRT
<213> ORGANISM: Bacillus subtilis

<400> SEQUENCE: 46

Met Glu Thr Tyr Ile Leu Ser Leu Asp Gln Gly Thr Thr Ser Ser Arg
1               5                   10                  15
Ala Ile Leu Phe Asn Lys Glu Gly Lys Ile Val His Ser Ala Gln Lys
            20                  25                  30
```

-continued

```
Glu Phe Thr Gln Tyr Phe Pro His Pro Gly Trp Val Glu His Asn Ala
             35                  40                  45

Asn Glu Ile Trp Gly Ser Val Leu Ala Val Ile Ala Ser Val Ile Ser
 50                  55                  60

Glu Ser Gly Ile Ser Ala Ser Gln Ile Ala Gly Ile Gly Ile Thr Asn
 65                  70                  75                  80

Gln Arg Glu Thr Thr Val Val Trp Asp Lys Asp Thr Gly Ser Pro Val
                 85                  90                  95

Tyr Asn Ala Ile Val Trp Gln Ser Arg Gln Thr Ser Gly Ile Cys Glu
                100                 105                 110

Glu Leu Arg Glu Lys Gly Tyr Asn Asp Lys Phe Arg Glu Lys Thr Gly
            115                 120                 125

Leu Leu Ile Asp Pro Tyr Phe Ser Gly Thr Lys Val Lys Trp Ile Leu
        130                 135                 140

Asp Asn Val Glu Gly Ala Arg Glu Lys Ala Glu Lys Gly Glu Leu Leu
145                 150                 155                 160

Phe Gly Thr Ile Asp Thr Trp Leu Ile Trp Lys Met Ser Gly Gly Lys
                165                 170                 175

Ala His Val Thr Asp Tyr Ser Asn Ala Ser Arg Thr Leu Met Phe Asn
            180                 185                 190

Ile Tyr Asp Leu Lys Trp Asp Asp Gln Leu Leu Asp Ile Leu Gly Val
        195                 200                 205

Pro Lys Ser Met Leu Pro Glu Val Lys Pro Ser Ser His Val Tyr Ala
    210                 215                 220

Glu Thr Val Asp Tyr His Phe Phe Gly Lys Asn Ile Pro Ile Ala Gly
225                 230                 235                 240

Ala Ala Gly Asp Gln Gln Ser Ala Leu Phe Gly Gln Ala Cys Phe Glu
                245                 250                 255

Glu Gly Met Gly Lys Asn Thr Tyr Gly Thr Gly Cys Phe Met Leu Met
            260                 265                 270

Asn Thr Gly Glu Lys Ala Ile Lys Ser Glu His Gly Leu Leu Thr Thr
        275                 280                 285

Ile Ala Trp Gly Ile Asp Gly Lys Val Asn Tyr Ala Leu Glu Gly Ser
    290                 295                 300

Ile Phe Val Ala Gly Ser Ala Ile Gln Trp Leu Arg Asp Gly Leu Arg
305                 310                 315                 320

Met Phe Gln Asp Ser Ser Leu Ser Glu Ser Tyr Ala Glu Lys Val Asp
                325                 330                 335

Ser Thr Asp Gly Val Tyr Val Val Pro Ala Phe Val Gly Leu Gly Thr
            340                 345                 350

Pro Tyr Trp Asp Ser Asp Val Arg Gly Ser Val Phe Gly Leu Thr Arg
        355                 360                 365

Gly Thr Thr Lys Glu His Phe Ile Arg Ala Thr Leu Glu Ser Leu Ala
    370                 375                 380

Tyr Gln Thr Lys Asp Val Leu Asp Ala Met Glu Ala Asp Ser Asn Ile
385                 390                 395                 400

Ser Leu Lys Thr Leu Arg Val Asp Gly Ala Val Lys Asn Asn Phe
                405                 410                 415

Leu Met Gln Phe Gln Gly Asp Leu Leu Asn Val Pro Val Glu Arg Pro
            420                 425                 430

Glu Ile Asn Glu Thr Thr Ala Leu Gly Ala Ala Tyr Leu Ala Gly Ile
        435                 440                 445
```

```
Ala Val Gly Phe Trp Lys Asp Arg Ser Glu Ile Ala Asn Gln Trp Asn
    450                 455                 460

Leu Asp Lys Arg Phe Glu Pro Glu Leu Glu Glu Lys Arg Asn Glu
465                 470                 475                 480

Leu Tyr Lys Gly Trp Gln Lys Ala Val Lys Ala Met Ala Phe Lys
                485                 490                 495

<210> SEQ ID NO 47
<211> LENGTH: 15
<212> TYPE: DNA
<213> ORGANISM: Artificial
<220> FEATURE:
<223> OTHER INFORMATION: DNA fragment coding 231-235 region of GlpK

<400> SEQUENCE: 47
gacggcaaag gcggc                                                        15

<210> SEQ ID NO 48
<211> LENGTH: 5
<212> TYPE: PRT
<213> ORGANISM: Escherichia coli

<400> SEQUENCE: 48

Gly Gly Lys Gly Gly
                5

<210> SEQ ID NO 49
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 49

Gly Gly Lys Asp Gly
                5

<210> SEQ ID NO 50
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 50

Gly Gly Arg Ile Leu
                5

<210> SEQ ID NO 51
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 51

Gly Gly Arg Leu Glu
                5

<210> SEQ ID NO 52
<211> LENGTH: 5
<212> TYPE: PRT
<213> ORGANISM: Artificial
<220> FEATURE:
<223> OTHER INFORMATION: 231-235 region of mutant GlpK
```

```
<400> SEQUENCE: 52

Gly Gly Lys Thr Phe
                  5

<210> SEQ ID NO 53
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 53

Gly Gly Arg Ile Pro
                  5

<210> SEQ ID NO 54
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 54

Gly Gly Thr Leu Leu
                  5

<210> SEQ ID NO 55
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 55

Arg Glu Ala Arg Ala
                  5

<210> SEQ ID NO 56
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 56

Arg Ala His Leu Ala
                  5

<210> SEQ ID NO 57
<211> LENGTH: 5
<212> TYPE: PRT
<213> ORGANISM: Artificial
<220> FEATURE:
<223> OTHER INFORMATION: 231-235 region of mutant GlpK

<400> SEQUENCE: 57

Asp Gly Lys Gly Gly
                  5
```